(12) United States Patent
Liles et al.

(10) Patent No.: US 11,397,183 B2
(45) Date of Patent: Jul. 26, 2022

(54) BIOMARKERS AND USES THEREOF FOR SELECTING IMMUNOTHERAPY INTERVENTION

(71) Applicants: FRED HUTCHINSON CANCER CENTER, Seattle, WA (US); UNIVERSITY OF WASHINGTON, Seattle, WA (US); BLOODWORKS NORTHWEST, Seattle, WA (US)

(72) Inventors: W. Conrad Liles, Seattle, WA (US); Cameron J. Turtle, Seattle, WA (US); David G. Maloney, Issaquah, WA (US); Stanley R. Riddell, Sammamish, WA (US); Mark M. Wurfel, Seattle, WA (US); Jose Lopez, Seattle, WA (US); Dominic Chung, Bellevue, WA (US); Junmei Chen, Seattle, WA (US)

(73) Assignees: Fred Hutchinson Cancer Center, Seattle, WA (US); University of Washington, Seattle, WA (US); Bloodworks Northwest, Seattle, WA (US)

( * ) Notice: Subject to any disclaimer, the term of this patent is extended or adjusted under 35 U.S.C. 154(b) by 0 days.

(21) Appl. No.: 16/484,788

(22) PCT Filed: Feb. 9, 2018

(86) PCT No.: PCT/US2018/017655
§ 371 (c)(1),
(2) Date: Aug. 8, 2019

(87) PCT Pub. No.: WO2018/148567
PCT Pub. Date: Aug. 16, 2018

(65) Prior Publication Data
US 2019/0361026 A1    Nov. 28, 2019

Related U.S. Application Data

(60) Provisional application No. 62/544,709, filed on Aug. 11, 2017, provisional application No. 62/456,798, filed on Feb. 9, 2017.

(51) Int. Cl.
| | |
|---|---|
| *C07K 16/22* | (2006.01) |
| *G01N 33/574* | (2006.01) |
| *G16H 50/30* | (2018.01) |
| *G16B 40/10* | (2019.01) |
| *C07K 16/24* | (2006.01) |

(52) U.S. Cl.
CPC ....... *G01N 33/57484* (2013.01); *C07K 16/22* (2013.01); *C07K 16/248* (2013.01); *G16B 40/10* (2019.02); *G16H 50/30* (2018.01); *G01N 2333/515* (2013.01)

(58) Field of Classification Search
CPC ................................................ G01N 33/57484

USPC ........................................................ 435/7.23
See application file for complete search history.

(56) References Cited

U.S. PATENT DOCUMENTS

| 8,980,268 B2 | 3/2015 | Lowy et al. |
|---|---|---|
| 9,017,670 B2 | 4/2015 | Thurston |
| 2013/0095065 A1 | 4/2013 | Peters et al. |

FOREIGN PATENT DOCUMENTS

| WO | 97/09433 A1 | 3/1997 |
|---|---|---|
| WO | 2015/095895 A1 | 6/2015 |

OTHER PUBLICATIONS

Tockman et al (Cancer Res., 1992, 52:2711s-2718s).*
Lee et al (The Lancet, 2015, 385: 517-528).*
Doessegger et al (Clinical & Tanslational Immunology, 2015, 4(e39): 1-9).*
Teachey (Blood, 2015, 126(23): 1334) Abstract.*
Augustin et al., "Control of vascular morphogenesis and homeostasis through the angiopoietin-Tie system" *Nat Rev Mol Cell Biol* 10(3):165-177, 2009.
Davila et al., "Efficacy and Toxicity Management of 19-28z CAR T Cell Therapy in B Cell Acute Lymphoblastic Leukemia," *Sci Transl Med* 6(224):224ra25, 2014 (12 pages).
Fiedler et al., "Angiopoietin-2 sensitizes endothelial cells to TNF-α and has a crucial role in the induction of inflammation," *Nature Medicine* 12(2):235-239, 2006.
Fiedler et al., "The Tie-2 ligand Angiopoietin-2 is stored in and rapidly released upon stimulation from endothelial cell Weibel-Palade bodies," *Blood* 103(11):4150-4156, 2004 (8 pages).
Higgins et al., "Dysregulation of angiopoietin-1 plays a mechanistic role in the pathogenesis of cerebral malaria," *Science Translational Medicine* 8(358):358ra128, 2016 (12 pages).
Huang et al., "Angiopoietin-1/Tie-2 activation contributes to vascular survival and tumor growth during VEGF blockade," *International Journal of Oncology* 34:79-87, 2009.
Imhof et al., "Angiogenesis and inflammation face off," *Nature Medicine* 12(2):171-172, 2006.
Kim et al., "A designed angiopoietin-2 variant, pentameric COMP-Ang2, strongly activates Tie2 receptor and stimulates angiogenesis," *Biochimica et Biophysica Acta* 1793:772-780, 2009.

(Continued)

*Primary Examiner* — Sean E Aeder
(74) *Attorney, Agent, or Firm* — Seed IP Law Group LLP

(57) ABSTRACT

The instant disclosure provides biomarkers and methods for identifying subjects at risk of developing cytokine release syndrome (CRS), neurotoxicity, or both after adoptive immunotherapy to guide preemptive intervention, modified therapy, or the like. For example, adverse event biomarkers may be measured in a subject before pre-conditioning chemotherapy, before immunotherapy (e.g., adoptive immunotherapy infusion comprising a chimeric antigen receptor (CAR) modified T cell), or shortly after pre-conditioning chemotherapy and/or immunotherapy. Exemplary biomarkers include temperature, cytokine levels and endothelial activation biomarkers, such as angiopoietin 2, von Willebrand factor (vWF), ratio of angiopoietin 2 to angiopoietin 1, and ratio of ADAMTS13 to vWF. Also provided are methods of treating subjects identified as at risk of developing cytokine release syndrome (CRS), neurotoxicity, or both to minimize such potential adverse events.

21 Claims, 24 Drawing Sheets

(56) References Cited

OTHER PUBLICATIONS

Maliba et al., "Angiopoietin-mediated endothelial P-selectin translocation: cell signaling mechanisms," *Journal of Leukocyte Biology* 83:352-360, 2008.
Page et al., "Dysregulation of Angiopoietin 1 and 2 in *Escherichia coli* O157:H7 Infection and the Hemolytic-Uremic Syndrome," *JID* 208:929-933, 2013.
Ricciuto et al., "Angiopoietin-1 and angiopoietin-2 as clinically informative prognostic biomarkers of morbidity and mortality in severe sepsis," *Crit Care Med* 39(4):702-710, 2011.
Turtle et al., "Biomarkers of Cytokine Release Syndrome and Neurotoxicity after CD19 CAR-T Cells and Mitigation of Toxicity by Cell Dose," *Blood* 128(22):1852, 2016 (Abstract Only) (6 pages).
Turtle et al., "CD19-Targeted Chimeric Antigen Receptor-Modified T-Cell Immunotherapy for B-Cell Malignancies," *Clinical Pharmacology & Therapeutics* 100(3):252-258, 2016.
Turtle et al., "Rate of durable complete response in ALL, NHL, and CLL after immunotherapy with optimized lymphodepletion and defined composition CD19 CAR-T cells," *American Society of Clinical Oncology*: 102, 2016 (Abstract Only) (1 page).
Anargyrou et al., "Normalization of the serum angiopoietin-1 to angiopoietin-2 ratio reflects response in refractory/resistant multiple myeloma patients treated with bortezomib," *haematologica* 93(3):451-454, 2008.
Gallagher et al., "Angiopoietin 2 Is a Potential Mediator of High-Dose Interleukin 2-Induced Vascular Leak," *Clin Cancer Res* 13(7):2115-2120, 2007. (7 pages).
Gust et al., "Endothelial Activation and Blood-Brain Barrier Disruption in Neurotoxicity after Adoptive Immunotherapy with CD19 CAR-T Cells," *Cancer Discovery* 7(12): 1404-1419, 2017.
Hay et al., "Kinetics and biomarkers of severe cytokine release syndrome after CD19 chimeric antigen receptor-modified T-cell therapy," *Blood* 130(21):2295-2306, 2017. (13 pages).
International Search Report and Written Opinion for International Application No. PCT/US2018/017655, dated Jun. 25, 2018, 18 pages.
Thijs et al., "Activation of the complement system during immunotherapy with recombinant IL-2. Relation to the development of side effects," *The Journal of Immunology* 144:2419-2424, 1990. (7 pages).
Wu et al., "Angiopoietin-2 as a Biomarker and Target for Immune Checkpoint Therapy," *Cancer Immunol Res* 5(1):17-28, 2017. (13 pages).
Alfieri et al., "Angiopoietin-1 variant reduces LPS-induced microvascular dysfunction in a murine model of sepsis," *Critical Care* 16:R182, 2012. (12 pages).
Altschul et al., "Basic Local Alignment Search Tool," *J. Mol. Biol.* 215:403-410, 1990.
Altschul et al., "Gapped BLAST and PSI-BLAST: a new generation of protein database search programs," *Nucleic Acids Research* 25(17):3389-3402, 1997.
Armulik et al., "Pericytes regulate the blood-brain barrier," *Nature* 468:557-561, 2010. (6 pages).
Brentjens et al., "Safety and persistence of adoptively transferred autologous CD19-targeted T cells in patients with relapsed or chemotherapy refractory B-cell leukemias," *Blood* 118(18):4817-4828, 2011. (25 pages).
Brudno et al., "Toxicities of chimeric antigen receptor T cells: recognition and management," *Blood* 127(26):3321-3330, 2016. (24 pages).

Cho et al., "COMP-Ang1: A designed angiopoietin-1 variant with nonleaky angiogenic activity," *PNAS* 101(15):5547-5552, 2004.
Kochenderfer et al., "Chemotherapy-Refractory Diffuse Large B-Cell Lymphoma and Indolent B-Cell Malignancies Can Be Effectively Treated With Autologous T Cells Expressing an Anti-CD19 Chimeric Antigen Receptor," *J. Clin. Oncol.* 33(6):540-549, 2015. (11 pages).
Lee et al., "Current concepts in the diagnosis and management of cytokine release syndrome," *Blood* 124(2):188-195, 2014.
Locke et al., "A Possible Cure for Refractory DLBCL: CARs Are Headed in the Right Direction," *Molecular Therapy* 25(10):2241-2243, 2017.
Lovegrove et al., "Serum Angiopoeitin-1 and -2 Levels Discriminate Cerebral Malaria from Uncomplicated Malaria and Predict Clinical Outcome in African Children," *PLoS One* 4(3):e4912, 2009. (8 pages).
Maude et al., "Chimeric Antigen Receptor T Cells for Sustained Remissions in Leukemia," *N. Eng. J. Med.* 371:1507-1517, 2014. (16 pages).
Mikacenic et al., "Biomarkers of Endothelial Activation Are Associated with Poor Outcome in Critical Illness," *PLoS One* 10(10):e0141251, 2015. (13 pages).
Page et al., "Biomarkers of endothelial activation/dysfunction in infectious diseases," *Virulence* 4(6):507-516, 2013.
Page et al., "Systemic Dysregulation of Angiopoietin-1/2 in Streptococcal Toxic Shock Syndrome," *Clin. Infect. Dis.* 52:e157, 2011. (5 pages).
Porter et al., "Chimeric antigen receptor T cells persist and induce sustained remissions in relapsed refractory chronic lymphocytic leukemia," *Sci. Transl. Med.* 7(303):303ra139, 2015. (12 pages).
Porter et al., "Chimeric Antigen Receptor-Modified T Cells in Chronic Lymphoid Leukemia," *N. Engl. J. Med.* 365(8):725-733, 2011. (12 pages).
Rustenhoven et al., "Brain Pericytes as Mediators of Neuroinflammation," *Trends Pharmacol. Sci.* 38(3):291-304, 2017. (14 pages).
Schwameis et al., "Von Willebrand factor excess and ADAMTS13 deficiency: a unifying pathomechanism linking inflammation to thrombosis in DIC, malalaria, and TTP," *Thromb. Haemost.* 113(4):708-718, 2015. (22 pages).
Teachey et al., "Identification of Predictive Biomarkers for Cytokine Release Syndrome after Chimeric Antigen Receptor T-cell Therapy for Acute Lymphoblastic Leukemia," *Cancer Dis.* 6(6):664-679, 2016.
Turtle et al., "CD19 CAR-T cells of defined $CD4^+:CD8^+$ composition in adult B cell ALL patients," *J. Clin. Invent.* 126(6):2123-2138, 2016.
Turtle et al., "Immunotherapy of non-Hodgkin's lymphoma with a defined ratio $CD8^+$ and $CD4^+$ CD19-specific chimeric antigen receptor-modified T cells," *Sci. Transl. Med.* 8(355):355ra116, 2016. (13 pages).
U.S. National Laboratory of Medicine, "Laboratory Treated T Cells in Treating Patients With Relapsed or Refractory Chronic Lymphocytic Leukemia, Non-Hodgkin Lymphoma, or Acute Lymphoblastic Leukemia," URL: clinicaltrials.gov/ct2/show/NCT01865617, last updated: Dec. 13, 2019. (10 pages).
Wu et al., "A rapid enzyme-linked assay for ADAMTS-13," *J. Thromb. Haemost.* 4:129-136, 2006.
Yarlagadda et al., "The Blood Brain Barrier and the Role of Cytokines in Neuropsychiatry," *Psychiatry* 6(11):18-22, 2009.
Cheimarioti et al., "IL-8 and MCP-1 in children with acute lymphoblastic leukemia and potential correlation with neurotoxicity and thromboembolic phenomena," *International Journal of Diseases and Disorders* 1(6):055-058, Nov. 2013. (5 pages).
Chung et al., "High-density lipoprotein modulates thrombosis by preventing von Willebrand factor self-association and subsequent platelet adhesion," *Blood* 127(5):637-645, Feb. 4, 2016.

* cited by examiner

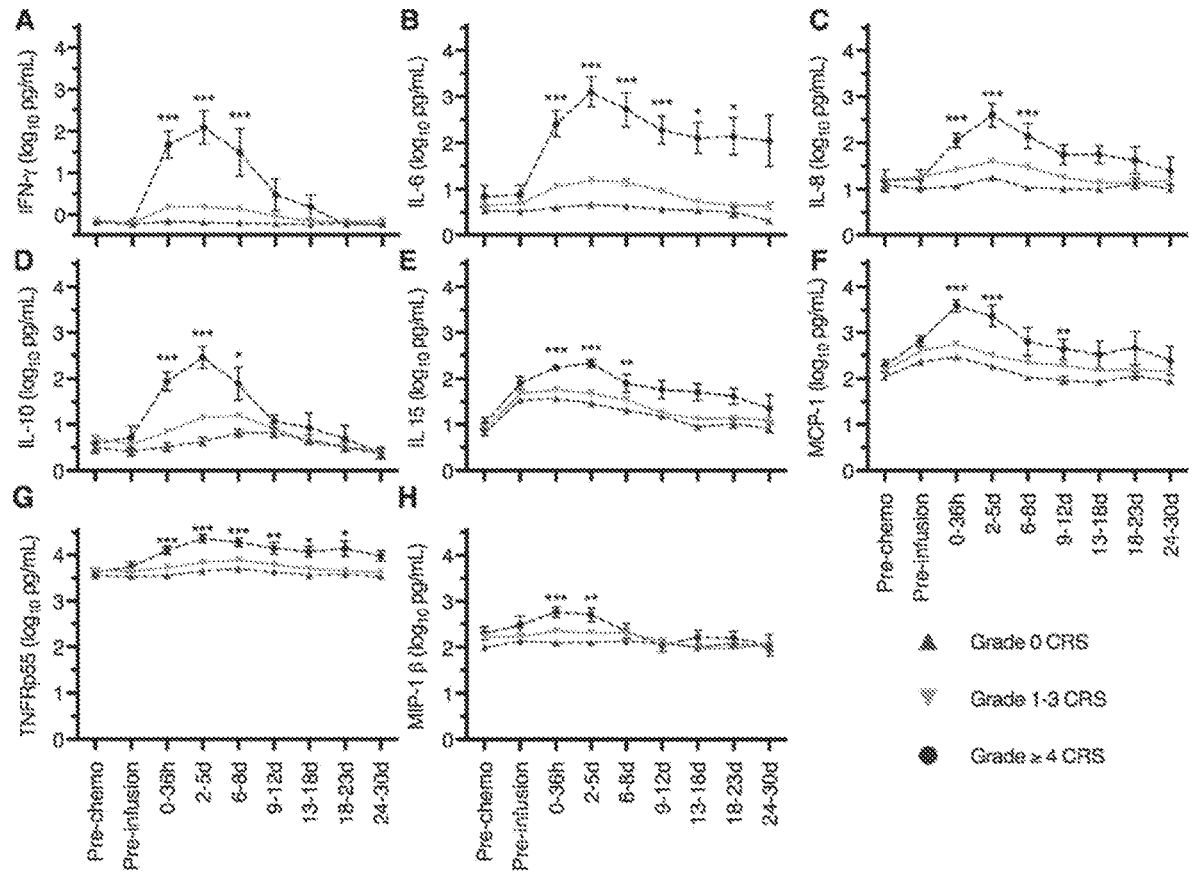
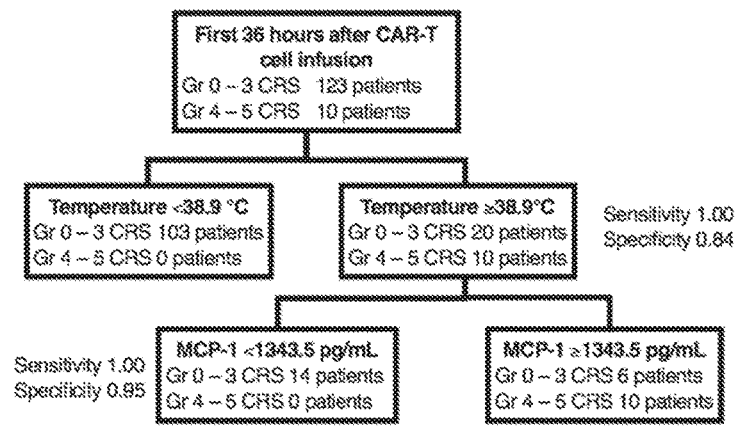
Figs. 13A – 13I

BIOMARKERS AND USES THEREOF FOR SELECTING IMMUNOTHERAPY INTERVENTION

STATEMENT OF GOVERNMENT INTEREST

This invention was made with government support under CA136551 awarded by the National Institutes of Health. The government has certain rights in the invention.

BACKGROUND

Lymphodepletion chemotherapy followed by infusion of T cells that are genetically modified to express a chimeric antigen receptor (i.e., CAR-modified T cells) has produced high response rates in clinical studies, such as in refractory B-cell acute lymphoblastic leukemia (B-ALL), chronic lymphocytic leukemia (CLL), and non-Hodgkin's lymphoma (NHL) (Davila et al., Sci. Transl. Med. 6:224ra25, 2014; Kochenderfer et al., J. Clin. Oncol. 33:540, 2015; Maude et al., N. Engl. J. Med. 371:1507, 2014; Porter et al., Sci. Transl. Med. 7:303ra139, 2015; Turtle et al. I, J. Clin. Invest. 126:2123, 2016; Turtle et al. II, Sci. Transl. Med. 8:355ra116, 2016). Durable complete responses (CRs) without subsequent anti-tumor therapy have been observed in a subset of patients who received CD19 CAR-T cell therapy, demonstrating the potential of this approach (Turtle et al. I and II, 2016; Porter et al., 2015).

For example, when infused antigen-specific CAR-modified T cells encounter an antigen positive target cell, in vivo signaling through the CAR induces CAR-T cell proliferation, cytokine secretion, and target cell lysis (Turtle et al., Clin. Pharmacol. Ther. 100:252, 2016). Within approximately 2 weeks after CAR-modified T cell infusion, some patients will develop cytokine release syndrome (CRS), a systemic inflammatory response initiated by T cell activation and characterized by fever and hypotension (Brudno and Kochenderfer, Blood 127:3321, 2016; Lee et al., Blood 124:188, 2014). Neurologic adverse events are frequently observed in association with CRS after CAR-modified T cell immunotherapy, and in rare instances can be fatal (Davila et al., 2014; Kochenderfer et al., 2015; Maude et al., 2014; Porter et al., 2015; Turtle et al. I, 2016; Turtle et al. II, 2016); however, a detailed clinical description of the syndrome has not been reported and the mechanisms of neurotoxicity have not been identified.

After adoptive transfer, activation of CAR-T cells by encounter with $CD19^+$ tumor or normal B cells results in proliferation of CAR-T cells, lysis of the target cell, and cytokine secretion, which can be associated with the clinical presentations of cytokine release syndrome (CRS) and neurotoxicity. CRS after CD19 CAR-T cell therapy occurs in 54-91% of patients, including severe CRS in 8.3-43% (Turtle II, 2016; Turtle I, 2016; Kochenderfer et al., 2015; Porter et al., 2015; Davila et al., 2014; Locke et al., Mol Ther. 25:285, 2017; Brentjens et al., Blood. 118:4817, 2011; Porter et al., N. Engl. J. Med. 365:725, 2011). CRS presents with fever, hypotension, coagulopathy and capillary leak, and, if severe, can be fatal; however, a comprehensive description of the kinetics of presentation and biomarkers of CRS in a large cohort of patients has not been reported (Brudno and Kochenderfer, Blood. 127:3321, 2016). The increased availability of CD19 CAR-T cell therapies in multicenter trials highlight the need to provide clinicians treating B-ALL, NHL and CLL patients with a detailed description of the clinical syndrome of CRS.

Hence, there remains a need in the art for biomarkers to identify a subject at risk of having an adverse event in response to immunotherapy. The present disclosure meets such needs, and further provides other related advantages.

BRIEF DESCRIPTION OF THE DRAWINGS

FIGS. 13A-13I. Biomarkers for early prediction of grade ≥4 CRS. (A-H) Concentrations of listed cytokines in serum obtained from patients at the indicated time points. Pre-chemo, prior to the start of lymphodepletion chemotherapy; Pre-infusion, before CAR-T cell infusion; h, hours; d, days after CAR-T cell infusion. P values were determined using the Kruskal-Wallis test, *P<0.0001, 0.0001<P<0.001, *0.001<P<0.005. (I) An algorithm for early identification of patients at high risk of grade ≥4 CRS using classification tree modeling. Early high fever (≥38.9° C.) within the first 36 hours after CAR-T cell infusion triggers evaluation of serum MCP-1 concentration. Patients with fever ≥38.9° C. and serum MCP-1≥1343.5 pg/mL are at high risk for subsequent development of grade ≥4 CRS. Gr, grade.

DETAILED DESCRIPTION

Figure 1A:
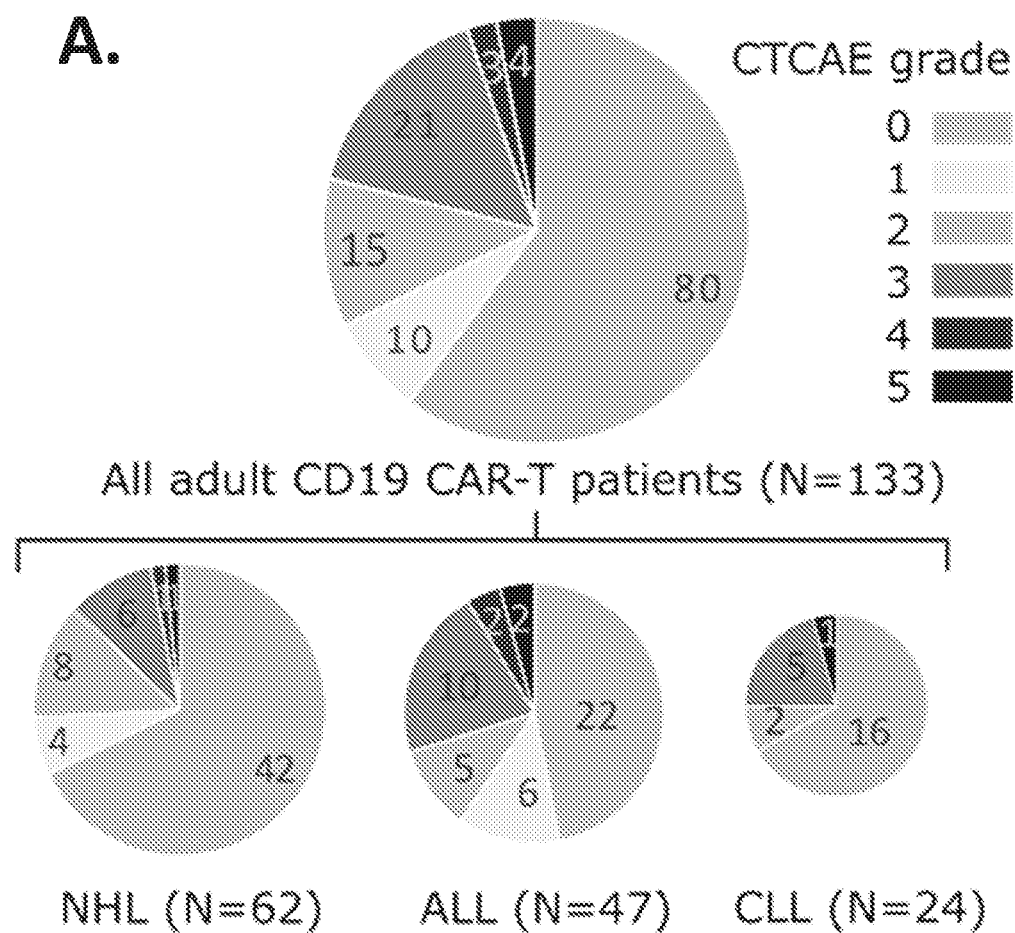
FIGS. 1A-1G. Frequency, kinetics, and treatment of neurotoxicity. (A) The numbers of patients with each overall neurotoxicity grade are shown for the entire cohort and each disease. The diameters of each pie chart indicate the relative size of each subgroup. (B) The swimmer plot (bottom) shows the kinetics of the severity of neurotoxicity in each patient who developed neurotoxicity through 28 days after CAR-modified T cell infusion (n=53). Each row represents one patient and the colors indicate the highest grade of neurotoxicity recorded on each day. The graph (top) shows the mean of the highest grade of neurotoxicity occurring in all patients on each day after CAR T cell infusion. (C) Numbers of patients with each grade of neurotoxicity and CRS. Cumulative incidences of (D) fever, (E) any grade of neurotoxicity, and (F) the peak grade of neurotoxicity, are shown for patients with grade 1-2 and grade ≥3 neurotoxicity. (G) The severity of neurotoxicity is shown in all patients with neurotoxicity who received treatment with tocilizumab (arrowheads) and/or corticosteroids (stars). The colors indicate the highest neurotoxicity grade for each day.

The instant disclosure provides methods for diagnosing or detecting the risk of an adverse event associated with immunotherapy, such as cytokine release syndrome (CRS), neurotoxicity or both. Risk factors that are associated with the incidence and severity of subsequent CRS were identified before and after CAR-T cell infusion, allowing identification of patients at high risk of severe toxicity and candidates for early intervention. In particular, various biomarkers examined individually and in various combinations indicate what therapies to apply, what therapeutic regimens to apply, what therapies to adjust, what therapies to avoid, or any combination thereof that will be the most beneficial to a subject at risk of having an adverse event associated with immunotherapy. Such biomarkers include the subject's temperature, levels of inflammatory cytokines and the presence of endothelial activation biomarkers. Exemplary endothelial activation biomarkers include angiopoietin-2 (encoded by ANGPT2), angiopoietin-1 (encoded by ANGPT1), vascular cell adhesion molecule 1 (VCAM-1, encoded by VCAM1, which can be the soluble form, sVCAM-1), a ratio of angiopoietin-2 to angiopoietin-1, a ratio of VCAM-1 to angiopoietin-1, von Willebrand factor (vWF), or a ratio of ADAMTS13 to vWF.

The instant disclosure further provides methods for treating hematologic malignancies in mammalian subjects, comprising obtaining the results from the methods comprising identifying the subject as at risk of developing an adverse event associated with cellular immunotherapy when the adverse event biomarker is altered as compared to a normal sample; and administering to the subject a pre-emptive treatment, an altered cellular immunotherapy regimen, or both to minimize the risk for the potential adverse event.

By way of background, lymphodepletion chemotherapy and targeted chimeric antigen receptor (CAR)-modified T (CAR-T) cell infusion for hematologic malignancies, including relapsed and refractory malignancies, can be complicated by various adverse events (AEs), including cytokine release syndrome (CRS), neurotoxicity, or both. For example, in CD19-specific CAR-T cell immunotherapy patients, the incidence of grade ≥3 neurotoxicity is similar to that described in previous reports (Davila et al., 2014; Kochenderfer et al., 2015; Maude et al., 2014; Porter et al., 2015). The instant disclosure provides an approach to reduce the risk of, for example, CD19 CAR-T cell therapy by early identification of patients who are at high risk of developing severe CRS at a time when intervention or modification of the treatment regimen could be instituted. Multivariable analysis identified baseline and treatment risk factors for CRS, including those associated with more robust CAR-T cell expansion, such as higher marrow tumor burden, Cy/Flu lymphodepletion, and higher CAR-T cell dose. Other factors that were associated with CRS (which may reflect the higher tumor burden in these patients) included thrombocytopenia and manufacturing of CAR-T cells from bulk CD8+ T cells.

This disclosure also provides detailed clinical, radiologic and pathologic characterization of neurotoxicity associated with CD19 CAR-T cell infusion that will facilitate management of patients undergoing CD19 CAR-T cell therapy. For example, the Examples herein show that cytokine-mediated endothelial activation causing coagulopathy, capillary leak, and blood-brain barrier (BBB) disruption, which allows transit of high concentrations of systemic cytokines into the cerebrospinal fluid (CSF). In autopsy studies of two patients who had fatal toxicity, endothelial activation was identified, resulting in loss of cerebral vascular integrity in one patient manifesting as multifocal hemorrhage. In certain embodiments, a predictive classification tree algorithm based on the presence of fever and high serum IL-6 and/or CCL2 (MCP-1) concentrations to identify patients within the first 12-48 hours of CAR-T cell infusion who are at high risk of subsequent severe neurotoxicity and are candidates for early intervention. Finally, the present disclosure provides that patients with evidence of endothelial activation before lymphodepletion, before CAR-T cell infusion, or both are at increased risk of neurotoxicity after immunotherapy, and are candidates for early intervention, modification of the treatment regimen, or both.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated.

As used herein, the terms "about" and "consisting essentially of" mean±20% of the indicated range, value, or structure, unless otherwise indicated. In particular embodiments, the term "about" means±2.5% of the indicated range or value for each of the following terms only: "sensitivity," "specificity," and "temperature."

It should be understood that the terms "a" and "an" as used herein refer to "one or more" of the enumerated components. The use of the alternative (e.g., "or") should be understood to mean either one, both, or any combination thereof of the alternatives or enumerated components. As used herein, the terms "include," "have" and "comprise" are used synonymously, which terms and variants thereof are intended to be construed as non-limiting.

As used herein, "hyperproliferative disorder" refers to excessive growth or proliferation as compared to a normal or undiseased cell. Representative hyperproliferative disorders include tumors, cancers, neoplastic tissue, carcinoma, sarcoma, malignant cells, pre-malignant cells, as well as non-neoplastic or non-malignant hyperproliferative disorders (e.g., adenoma, fibroma, lipoma, leiomyoma, hemangioma, fibrosis, restenosis, as well as autoimmune diseases such as rheumatoid arthritis, osteoarthritis, psoriasis, inflammatory bowel disease, or the like). In certain embodiments, a hyperproliferative disorder comprises a hematologic malignancy, such as a lymphoma, a leukemia or a myeloma.

As used herein, "cancer recurrence" or "cancer relapse" is defined as the return of cancer after treatment and after a period of time (e.g., days, weeks, months or years) during which the cancer cannot be detected. The cancer may come back in the same tissue or in other parts of the body.

As used herein, "prognosis" is the likelihood of the clinical outcome for a subject afflicted with a specific disease or disorder. With regard to cancer, the prognosis is a representation of the likelihood (probability) that the subject will survive (such as for 1, 2, 3, 4 or 5 years) and/or the likelihood that an adverse event (e.g., severe cytokine release syndrome, severe neurotoxicity, or both). A "poor prognosis" indicates a greater than 50% chance that the subject will not survive to a specified time point (such as 1, 2, 3, 4 or 5 years), and/or a greater than 50% chance that a severe adverse event will occur. In several examples, a poor prognosis indicates that there is a greater than 60%, 70%, 80%, or 90% chance that the subject will not survive and/or a greater than 60%, 70%, 80% or 90% chance that a severe adverse event will occur. Conversely, a "good prognosis" indicates a greater than 50% chance that the subject will survive to a specified time point (such as 1, 2, 3, 4, or 5 years), and/or a greater than 50% chance that a severe adverse event will not occur. In several examples, a good prognosis indicates that there is a greater than 60%, 70%, 80%, or 90% chance that the subject will survive and/or a greater than 60%, 70%, 80% or 90% chance that a severe adverse event will not occur.

The methods disclosed herein are used to detect biomarkers that indicate the risk, diagnosis, progression, prognosis, or monitoring of an adverse event associated with treatment of a hyperproliferative disorder, such as a hematologic malignancy. "Biomarker" refers to a cell, particle, molecule, compound, or other chemical entity or biologic structure that is an indicator of an abnormal biological condition (e.g., disease or disorder). Exemplary biomarkers include proteins (e.g., antigens or antibodies), carbohydrates, cells, microparticles, viruses, nucleic acids, or small organic molecules. For example, a biomarker may be a gene product that (a) is expressed at higher or lower levels, (b) has an altered ratio relative to another biomarker, (c) is present at higher or lower levels, (c) is a variant or mutant of the gene product, or (d) is simply present or absent, in a cell or tissue sample from a subject having or suspected of having a disease as compared to an undiseased tissue or cell sample from the subject having or suspected of having a disease, or as compared to a cell or tissue sample from a subject or a pool of subjects not having or suspected of having the disease. That is, one or more gene products are sufficiently specific to the test sample that one or more may be used to identify, predict, or detect the presence of disease, risk of disease, risk of an adverse event, or provide information for a proper or improved therapeutic regimen. A biomarker may refer to two or more components or a ratio thereof (e.g., proteins, nucleic acids, carbohydrates, or a combination thereof) that bind together, associate non-covalently to form a complex, disrupt the association of a complex or two or more molecules or proteins (e.g., angiopoietin-2 disrupts the complex of angiopoietin-1 and Tie2), or are affected by the presence of the other (e.g., ADAMTS13 is a protease that cleaves the von Willebrand factor (vWF) protein).

By "subject" is meant an organism having a hyperproliferative disease, such as a hematologic malignancy (e.g., lymphoma, leukemia, myeloma), or at risk of having an adverse event associated with immunotherapy against such a disease. A subject may benefit from a particular therapeutic regimen described herein, which can be based on, for example, a biomarker ratio selected from von Willebrand factor antigen (vWF Ag) to ADAMTS13 or angiopoietin-2 to angiopoietin-1 or VCAM-1 to angiopoietin-1, or a biomarker selected from fever, angiopoietin-2, angiopoietin-1, VCAM-1, vWF Ag, asymmetric dimethyl arginine (ADMA), IL-8, CCL26, endothelin-1, osteoprotegerin, CD142 tissue factor, C-reactive protein, E-selectin, P-selectin, P-selectin cofactor CD63/LAMP3, PAI-1, α-fucosyltransferase VI, circulating endothelial cells, endothelial microparticles, or any combination thereof. "Subject" also refers to an organism to which a small molecule, chemical entity, nucleic acid molecule, peptide, polypeptide or other therapy of this disclosure can be administered to treat, ameliorate or prevent recurrence of hyperproliferative disease, such as a hematologic malignancy (e.g., lymphoma, leukemia, myeloma) and to minimize the risk of an adverse event (e.g., CRS, neurotoxicity). In certain embodiments, a subject is an animal, such as a mammal or a primate. In other embodiments, a subject is a human or a non-human primate.

The term "biological sample" includes a blood sample, biopsy specimen, tissue explant, organ culture, biological fluid or specimen (e.g., blood, serum, plasma, ascites, mucosa, lung sputum, saliva, feces, cerebrospinal fluid (CSF)) or any other tissue or cell or other preparation from a subject or a biological source. A "biological source" may be, for example, a human or non-human animal subject, a primary cell or cell culture or culture adapted cell line including cell lines genetically engineered by human intervention to contain chromosomally integrated or episomal heterologous or recombinant nucleic acid molecules, somatic cell hybrid cell lines, immortalized or immortalizable cells or cell lines, differentiated or differentiatable cells or cell lines, transformed cells or cell lines, or the like. In a preferred embodiment, a biological sample is from a human, such as a serum sample. By "human patient" is intended a human subject who is afflicted with, at risk of developing or relapsing with, any disease or condition associated with a hyperproliferative disorder, or of having an adverse event associated with the treatment of such a hyperproliferative disorder.

A biological sample is referred to as a "test sample" when being tested or compared to a "control." A "control," as used herein, refers to an undiseased sample from the same patient and same tissue, a sample from a subject not having or suspected of having the disease of interest, a pool of samples from various subjects not having or suspected of having the disease of interest (e.g., including samples from two to about 100 subjects to about 1,000 subjects to about 10,000 subjects to about 100,000 subjects), or data from one or more subjects not having or suspected of having the disease of interest or having had an adverse event associated with the treatment of the disease (e.g., a database containing information on biomarker levels from one to about 100 to about 500 to about 1,000 to about 5,000 to about 10,000 to about 100,000 to about 1,000,000 or more subjects). In certain embodiments, a "test sample" is analyzed and the results (i.e., biomarker levels or activity) compared to a "control" comprising an average or certain identified baseline level calculated from a database having data derived from a plurality of analyzed undiseased or normal samples.

A "reference" or "standard" may optionally be included in an assay, which provides a measure of a standard or known baseline level of a target molecule, structure, or activity (e.g., "normal" level). In certain embodiments, a reference sample is a pool of samples (e.g., 2, 3, 4, 5, 6, 7, 8, 9, 10, or up to 100 or 1,000 or 10,000 samples combined) from healthy individuals (i.e., not having or suspected of having the disease of interest). In certain instances, a "test sample" and a "control sample" will be examined in an assay of the instant disclosure along with a reference sample. In these instances, the "test" and "control" samples may be collectively referred to as the "target samples" since they are being compared to a reference sample.

When referring to the level of the one or more biomarker in a test sample, "elevated" compared to a control, as used herein, means a statistically significant increase in level or activity. In certain embodiments, the level or activity of biomarker(s) in a test sample is elevated compared to a control in a statistically significant manner. In further embodiments, the level or activity of biomarker(s) in a test sample is increased in a statistically significant manner. For example, the difference between test and control levels or control may be about 2-fold, about 2.5-fold, about 3-fold, about 3.5-fold, about 4-fold, about 4.5-fold, about 5-fold, about 5.5-fold, about 6-fold, about 6.5-fold, about 7-fold, about 7.5-fold, about 8-fold, about 8.5-fold, about 9-fold, about 9.5-fold, about 10-fold, about 15-fold, about 20-fold, about 30-fold, or more. In certain instances, a statistically significant difference includes when a biomarker or related activity is present in a test sample but is absent or undetectable in the control.

In certain embodiments of this disclosure, a subject or biological source may be suspected of having or being at risk for developing an adverse event, such as CRS or neurotoxicity. In certain embodiments, a subject or biological source has a hematologic malignancy and may be suspected of or being at risk for developing an adverse event in association with a treatment of the hematologic malignancy (e.g., lymphoma, leukemia, myeloma), and in certain other embodiments of this disclosure; the subject or biological source may be known to be free of the presence of such disease, disorder, or condition, or free of any adverse event after treatment.

As used herein, "pre-diagnosis detection" refers to the detection of biomarkers after pre-treatment (e.g., lymphodepeletion), treatment (e.g., immunotherapy), both but prior to diagnosis of an adverse event. The phrase "pre-treatment detection" refers to the detection of biomarkers before pre-treatment (e.g., lymphodepeletion), treatment (e.g., immunotherapy), or both.

As used herein, "sensitivity" refers to a measure of the proportion of subjects having a disease (e.g., humans) who test positive for one or more biomarkers before or shortly after receiving treatment for the disease and who develop one or more adverse events shortly after the treatment over the total population of subjects who develop one or more adverse events (usually expressed as a percentage). For example, a human patient population having a hematologic cancer (e.g., leukemia, lymphoma, myeloma) and testing positive for one or more biomarkers before or shortly after (e.g., within 12 to 48 hours) immunotherapy (e.g., antibody, CAR-modified T cell), who develop one or more adverse events (e.g., high fever, cytokine release syndrome (CRS), neurotoxicity) will be a measure of the proportion of the patients identified as at risk for developing such one or more adverse events (e.g., the percentage of hematologic cancer patients who are correctly identified as at risk of developing and do develop the one or more adverse events based on detecting the one or more biomarkers before or shortly after treatment). In other words, "high sensitivity" (e.g., a sensitivity of at least 85%, 86%, 87%, 88%, 89%, 90%, 91%, 92%, 93%, 94%, 95%, 96%, 97%, 98%, 99% or 100%) means there are few or a low percentage of false negatives present and "low sensitivity" (e.g., a sensitivity below about 70%) means there are many or a high percentage of false negatives present.

As used herein, "specificity" refers to a measure of the proportion of subjects having a disease (e.g., humans) who test negative for the one or more biomarkers before or shortly after receiving treatment for the disease and who do not develop one or more adverse events over the total population of subjects who do not develop the one or more adverse events (usually expressed as a percentage). For example, a human patient population that has a hematopoietic cancer (e.g., leukemia, lymphoma) and tests negative for one or more biomarkers before or shortly after (e.g., within 12 to 48 hours) immunotherapy (e.g., antibody, CAR-modified T cell), who do not develop one or more adverse events (e.g., high fever, cytokine release syndrome (CRS), neurotoxicity) will be a measure of the proportion of patients properly identified as not at risk of developing such one or more adverse events (e.g., the percentage of hematopoietic cancer patients who are correctly identified as not at risk of developing and do not develop the one or more adverse events based on the absence of the one or more biomarkers before or shortly after treatment). In other words, "high specificity" (e.g., a sensitivity of at least 85%, 86%, 87%, 88%, 89%, 90%, 91%, 92%, 93%, 94%, 95%, 96%, 97%, 98%, 99% or 100%) means there are few or a low percentage of false positives present and "low specificity" (e.g., a sensitivity below about 70%) means there are many or a high percentage of false positives present.

In certain embodiments, any of the methods described herein have a sensitivity of at least about 85%, about 86%, about 87%, about 88%, about 89%, about 90%, about 91%, about 92%, about 93%, about 94%, about 95%, about 96%, about 97%, about 98%, about 99%, about 100%, or 100%. In some embodiments, the sensitivity for pre-diagnostic or pre-treatment detection of the risk for an adverse event associated with immunotherapy (e.g., CAR-T cell therapy), within about 36 hours of treatment, is about 100% or 100%.

In certain embodiments, any of the methods described herein have a specificity that is at least about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or about 100%. In some embodiments, the specificity for pre-diagnostic or pre-treatment detection of the risk for an adverse event associated with immunotherapy (e.g., CAR-T cell therapy), within about 36 hours of treatment, is about 80% to about 95%.

In further embodiments, any of the methods described herein for detecting the risk of an adverse event associated with immunotherapy, within about 36 hours of treatment, have a specificity that ranges from about 84% to about 92% and a sensitivity that is about 97.5%. In still further embodiments, any of the methods described herein for detecting the risk of an adverse event associated with immunotherapy, within about 36 hours of treatment, have a specificity that is at least about 94% and a sensitivity that is about 100%.

The "percent identity" or "sequence identity," as used herein, refers to the percentage of nucleic acid or amino acid residues in one sequence that are identical with the nucleic acid or amino acid residues in a reference polynucleotide or polypeptide sequence, respectively, (i.e., % identity=number of identical positions/total number of positions×100) after aligning the sequences and introducing gaps, if necessary, to achieve the maximum percent sequence identity of two or more sequences. For proteins, conservative substitutions are not considered as part of the sequence identity. The comparison of sequences and determination of percent identity between two or more sequences is accomplished using a mathematical algorithm, such as BLAST and Gapped BLAST programs at their default parameters (e.g., Altschul et al., *J. Mol. Biol.* 215:403, 1990; Altschul et al., *Nucleic Acids Res.* 25:3389, 1997; see also BLASTN or BLASTP at www.ncbi.nlm.nih.gov/BLAST).

A "conservative substitution" is recognized in the art as a substitution of one amino acid for another amino acid that has similar properties. Exemplary conservative substitutions are well known in the art (see, e.g., WO 97/09433, page 10, published Mar. 13, 1997; Lehninger, Biochemistry, Second Edition; Worth Publishers, Inc. NY:NY (1975), pp. 71-77; Lewin, Genes IV, Oxford University Press, NY and Cell Press, Cambridge, Mass. (1990), p. 8).

"Treatment," "treating" or "ameliorating" refers to either a therapeutic treatment or prophylactic/preventative treatment. A treatment is therapeutic if at least one symptom of disease (e.g., leukemia, lymphoma, myeloma) in an individual receiving treatment improves or a treatment may delay worsening of a progressive disease in an individual, or prevent onset of additional associated diseases or symptoms.

A "therapeutically effective amount (or dose)" or "effective amount (or dose)" refers to that amount of compound sufficient to result in amelioration of one or more symptoms of the disease being treated (e.g., leukemia, lymphoma, myeloma) in a statistically significant manner, or minimizing the risk of an adverse event. When referring to an individual active ingredient administered alone, a therapeutically effective dose refers to that ingredient alone. When referring to a combination, a therapeutically effective dose refers to combined amounts of the active ingredients that result in the therapeutic effect, whether administered serially or simultaneously (in the same formulation or in separate formulations).

The term "pharmaceutically acceptable" refers to molecular entities and compositions that do not produce allergic or other serious adverse reactions when administered using routes well known in the art.

A "patient in need" or "subject in need" refers to a patient or subject at risk of, or suffering from, an adverse event associated with immunotherapy of such a disease, disorder or condition (e.g., leukemia, lymphoma, myeloma) that is amenable to treatment or amelioration with an early intervention or altered therapy regimen as provided herein.

As used herein, the term "expression level" refers to the quantity of protein or gene expression by a cell or population of cells. Techniques for detecting and measuring protein expression are known to those of skill in the art and include, for example, immunostaining, immunoprecipitation, fluorescence-labeling, BCA, and Western blot. Techniques for detecting and measuring gene expression are known to those of skill in the art and include, for example, RT-PCR, in situ hybridization, fluorescence-labeled oligonucleotide probes, radioactively labeled oligonucleotide probes, and Northern blot.

As used herein, the terms "antibody" or "binding fragment," or "antibody fragment" refer to their standard meanings within the art; that is, an intact immunoglobulin molecule or a fragment thereof that is capable of binding an antigen.

As used herein, the term "nanobody" refers to an antibody fragment consisting of a single monomeric variable domain of a heavy-chain antibody. Nanobodies bind selectively to a specific antigen and, being smaller in size relative to antibodies, may bind smaller targets and may be favored over antibodies for cell transformation.

The term "T cell receptor," as used herein, refers to an heterodimeric antigen binding receptor derived from a T lymphocyte, comprising a an alpha/beta polypeptide dimer or a gamma/delta polypeptide dimer, each dimer comprising a variable region, a constant region, and an antigen binding site.

Diagnosing or Detecting Risk of Adverse Events Before Immunotherapy

In one aspect, the present disclosure provides methods for reducing the risk of an adverse event associated with cellular immunotherapy, comprising (i) measuring the level of a biomarker of endothelial activation in a biological sample from a mammalian subject having a hematologic malignancy and prior to cellular immunotherapy, wherein the biomarker of endothelial activation is selected from angiopoietin-2, angiopoietin-1, VCAM-1, von Willebrand factor antigen (vWF Ag), asymmetric dimethyl arginine (ADMA), IL-8, CCL26, endothelin-1, osteoprotegerin, CD142 tissue factor, C-reactive protein, E-selectin, P-selectin, P-selectin cofactor CD63/LAMP3, PAI-1, α-fucosyltransferase VI, circulating endothelial cells, endothelial microparticles, or any combination thereof; and (ii) identifying the subject as at risk of developing an adverse event associated with cellular immunotherapy when the biomarker of endothelial activation is increased as compared to a normal sample, wherein the at risk subject receives pre-emptive treatment for the adverse event, receives an altered cellular immunotherapy regimen, or both.

As used herein, "risk" is the likelihood (probability) of a subject developing an adverse event associated with the treatment of a hematologic malignancy. Risk is a representation of the likelihood that a subject will develop an adverse event within a period of time after treatment (such as minutes, hours, or days later). A "high risk" indicates a greater than 50% chance that the subject will develop an adverse event after a treatment. In certain embodiments, a high risk indicates that there is a greater than 60%, 70%, 80%, or 90% chance that a subject will develop an adverse event after a treatment. Conversely, a "low risk" indicates a less than 50% chance that the subject will develop an adverse event after a treatment. In certain embodiments, a low risk indicates that there is a less than 10%, 20%, 30%, or 40% chance of developing an adverse event after a treatment.

In some embodiments, a subject is at risk because the subject belongs to a subpopulation identified by specific characteristics, such as biomarkers of this disclosure, as well as age, gender, diet, ethnicity, or a combination thereof. A subject of a subpopulation is, for example, a human subject that is up to 6 years old, is from 6 years old to 17 years old, or is at least 17 years of age or older.

In certain embodiments, the present disclosure provides methods for reducing the risk of an adverse event associated with cellular immunotherapy wherein the biological sample is obtained before pre-conditioning, before cellular immunotherapy administration, or before both. In some embodiments, a subject having a hematologic malignancy and being treated with adoptive cellular immunotherapy (e.g., CAR-T cell therapy) will receive a "pre-conditioning" (or simply a "conditioning") regimen to reduce the tumor burden and to suppress the recipient's immune system to allow engraftment of the adoptive cellular immunotherapy. The conditioning may be myeloablative in which total body irradiation (TBI) or alkylating agents are administered, at doses that do not allow autologous hematologic recovery and, therefore, include stem cell therapy. For example, myeloablative conditioning may comprise TBI at 10 Gy, with cyclophosphamide (CY) at 200 mg/kg and busulfan (BU) at 16 mg/kg. Other agents that can be used in a myeloablative conditioning regimen at high doses, and in different combinations with CY or TBI, include melphalan (MEL), thiotepa (THIO), etoposide (VP16), and dimethylbusulfan. Alternatively, the conditioning may be non-myeloablative in which less toxic treatments are used and stem cell therapy is not needed. For example, non-myeloablative conditioning regimens include fludarabine and cyclophosphamide (Flu/CY), TBI at 2 Gy or 1 Gy, total lymphoid radiation (TLI), and anti-thymocyte globulin (ATG). In certain embodiments, conditioning for subjects with a hematologic malignancy (e.g., lymphoma, leukemia, myeloma) comprises administration daily for two to five days of cyclophosphamide (CY) at 30-60 mg/kg alone or CY at 30-60 mg/kg and fludarabine (Flu) at 25-30 mg/m$^2$.

Immunotherapy of this disclosure comprises cellular immunotherapy, including T cells modified to express on their cell surface a T cell receptor (TCR), chimeric antigen receptor (CAR), T-ChARM, an immunoreactive T cell, an immunoreactive Natural Killer cell, or the like. In certain embodiments, a T-ChARM comprises an extracellular component and an intracellular component connected by a hydrophobic portion, wherein the extracellular component comprises a binding domain that specifically binds a target, a tag cassette, and a connector region comprising a hinge, and wherein the intracellular component comprises an effector domain. In further embodiments, a CAR comprises an extracellular component and an intracellular component connected by a hydrophobic portion, wherein the extracellular component comprises a binding domain that specifically binds a target, and a connector region comprising a hinge, and wherein the intracellular component comprises an effector domain. In certain embodiments, a T-ChARM or CAR binding domain is a scFv, scTCR, receptor ectodomain, or ligand. T-ChARMs as disclosed in PCT Publication of WO 2015/095895 are incorporated herein by reference in their entirety. In certain embodiments, a T-ChARM or CAR binding domain is specific for CD19, CD20, CD22, CD37 or the like.

As used herein, the term "immunoreactive T cell" refers to a naturally occurring or engineered cytotoxic T lymphocyte (i.e., a CD8+ T cell) capable of killing a damaged or infected cell, and/or to a naturally occurring or engineered T helper cell (i.e., a CD4+ T cell) capable of effecting an immune response within the subject when presented with an antigen by an MHC1 marker. As used herein, the term "immunoreactive Natural Killer cell" refers to a naturally occurring or engineered cytotoxic lymphocyte of the innate immune system that is distinct from a cytotoxic T lymphocyte and which is capable of recognized and killing a damaged or infected cell without prior activation by MHCI markers.

In certain embodiments, the present disclosure provides methods for reducing the risk of an adverse event associated with cellular immunotherapy by measuring the level of one, two, three, four or five biomarkers of endothelial activation. Exemplary biomarkers of endothelial activation include one or more components from endothelial Weibel-Palade bodies, such as angiopoietin-2, vWF Ag, IL-8, CCL26, endothelin-1, osteoprotegerin, CD142 tissue factor, P-selectin, P-selectin cofactor CD63/LAMP3, PAI-1, α-fucosyltransferase VI, or any combination thereof. In particular embodiments, the biomarker of endothelial activation measured comprises vWF Ag, angiopoietin-2, angiopoietin-1, VCAM-1, or a combination thereof.

In further embodiments, the present disclosure provides methods for reducing the risk of an adverse event associated with cellular immunotherapy by measuring the level of at least one biomarker and at least one co-factor to the biomarker, and determining a ratio between the at least two markers. For example, an exemplary method of this disclosure comprises measuring the level of vWF Ag and measuring the activity co-factor ADAMTS13, wherein a ratio of ADAMTS13 to vWF Ag that is reduced as compared to a normal sample identifies the subject as at risk of developing an adverse event associated with cellular immunotherapy. In other embodiments, the method comprises measuring the level of angiopoietin-2, and the co-factor measured comprises measuring angiopoietin-1 level, wherein a ratio of angiopoietin-2 to angiopoietin-1 that is increased as compared to a normal sample identifies the subject as at risk of developing an adverse event associated with cellular immunotherapy. In further embodiments, the method comprises measuring the level of VCAM-1, and the co-factor measured comprises measuring angiopoietin-1 level, wherein a ratio of VCAM-1 to angiopoietin-1 that is increased as compared to a normal sample identifies the subject as at risk of developing an adverse event associated with cellular immunotherapy.

In still further embodiments, a subject identified in a method of this disclosure as at risk for an adverse event receives a pre-emptive treatment for the potential adverse event or an altered cellular immunotherapy regimen comprising administering the cellular immunotherapy at a reduced dose, a corticosteroid, an inflammatory cytokine antagonist, an endothelial cell stabilizing agent, or any combination thereof. In particular embodiments, a pre-emptive treatment comprises a corticosteroid selected from dexamethasone, prednisone, or both. In related embodiments, a pre-emptive treatment comprises an inflammatory cytokine antagonist comprising an anti-IL-6 antibody, an anti-IL-6R antibody, or both. In further embodiments, a pre-emptive treatment comprises administering a corticosteroid and an inflammatory cytokine antagonist, such as dexamethasone with tocilizumab or siltuximab, or prednisone with tocilizumab or siltuximab.

In any of the aforementioned embodiments, a pre-emptive treatment may comprise an angiopoietin-1 (Ang1) agonist, a Tie2 agonist or both. Exemplary Ang1 and Tie2 agonists are provided in, for example, Cho et al., *Proc. Nat'l. Acad. Sci. USA* 101:5547, 2004 (COMP-Ang1), Alfieri et al., *Crit. Care* 16:R182, 2012 (MAT-Ang1), Huang et al., *Int. J. Oncol.* 34:79, 2009 (Bow-Ang1), and Kim et al., *Biochim. Biophys. Acta* 1793:772, 2009 (COMP-Ang2). The Ang1 and Tie2 agonists of these publications are incorporated herein by reference in their entirety. In certain embodiments, an angiopoietin-1 agonist comprises hypertransfusion of platelets (e.g., to increase the amount of angiopoietin-1), COMP-Ang1, MAT-Ang1, Bow-Ang1, or a combination thereof. In other embodiments, a Tie2 agonist comprises COMP-Ang2. Furthermore, any one of the angiopoietin-1 agonists may be combined with the Tie2 agonist. In certain embodiments, an inflammatory cytokine antagonist treatment comprises plasma exchange (e.g., to reduce the amount of inflammatory cytokines).

In certain embodiments, provided herein are methods of monitoring progression of an adverse event in a subject, comprising measuring the level of a biomarker of endothelial activation in a biological sample from a mammalian subject having a hematologic malignancy and prior to cellular immunotherapy, wherein the biomarker of endothelial activation is selected from angiopoietin-2, angiopoietin-1, VCAM-1, von Willebrand factor antigen (vWF Ag), asymmetric dimethyl arginine (ADMA), IL-8, CCL26, endothelin-1, osteoprotegerin, CD142 tissue factor, C-reactive protein, E-selectin, P-selectin, P-selectin cofactor CD63/LAMP3, PAI-1, α-fucosyltransferase VI, circulating endothelial cells, endothelial microparticles, or any combination thereof, and monitoring the subject for a risk of developing an adverse event associated with cellular immunotherapy when the biomarker of endothelial activation is increased as compared to a normal sample.

In any of the aforementioned embodiments, provided herein are methods for reducing the risk of an adverse event associated with cellular immunotherapy or methods of monitoring progression of an adverse event in a subject, wherein the subject has a hematologic malignancy is selected from Hodgkin's lymphoma, non-Hodgkins lymphoma (NHL), primary central nervous system lymphomas, T cell lymphomas, small lymphocytic lymphoma (SLL), B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma (mucosa-associated lymphoid tissue (MALT) lymphoma), nodal marginal zone B-cell lymphoma, follicular lymphoma, mantle cell lymphoma, diffuse large B-cell lymphoma (DLBCL), mediastinal (thymic) large B-cell lymphoma, intravascular large B-cell lymphoma, primary effusion lymphoma, acute lymphoblastic leukemia (ALL), acute myeloid leukemia (AML), chronic lymphocytic leukemia (CLL), chronic myoblastic leukemia (CML), Hairy cell leukemia (HCL), chronic myelomonocytic leukemia (CMML), juvenile myelomonocytic leukemia (JMML), large granular lymphocytic leukemia (LGL), blastic plasmacytoid dendritic cell neoplasm (BPDCN), Burkitt lymphoma/leukemia, multiple myeloma, Bence-Jones myeloma, non-secretory myeloma, plasmacytoma, amyloidosis, monoclonal gammopathy of unknown significance (MGUS), or Waldenstrom's macroglobulinemia.

In any of the aforementioned embodiments, provided herein are methods for reducing the risk of an adverse event associated with cellular immunotherapy or methods of monitoring progression of an adverse event in a subject, wherein the adverse event is cytokine release syndrome (CRS), neurotoxicity, or both.

Methods of Identifying Subjects at Risk of Adverse Events after Immunotherapy

In certain aspects, the present disclosure provides methods for diagnosing or detecting the risk of an adverse event associated with cellular immunotherapy, which methods involve (i) measuring the level of an adverse event biomarker of endothelial activation in a biological sample from a mammalian subject having a hematologic malignancy within about 12 hours to about 48 hours after cellular immunotherapy, wherein the adverse event biomarker measured comprises the subject's temperature and a cytokine selected from IL-6, CCL2, IFN-γ, IL-10, IL-15, IL-2, or any combination thereof provided that at least IL-6, CCL2 or both cytokine levels are measured; and (ii) identifying the subject as at risk of developing an adverse event of cytokine release syndrome (CRS), neurotoxicity, or both after cellular immunotherapy when the subject's temperature is at least 38° C. and the level of IL-6 is increased at least 2- to 5-fold and/or the level of CCL2 is increased at least 5- to 20-fold as compared to a normal sample, wherein the at risk subject receives pre-emptive treatment for the adverse event, receives an altered cellular immunotherapy regimen, or both.

In certain embodiments, the present disclosure provides methods for diagnosing or detecting the risk of an adverse event associated with cellular immunotherapy wherein the biological sample is obtained after pre-conditioning, after cellular immunotherapy administration, or after both. In some embodiments, a subject having a hematologic malignancy is conditioned before treatment with an adoptive cellular immunotherapy (e.g., CAR-T cell therapy). The conditioning regimen may be myeloablative or non-myeloablative as described herein. In certain embodiments, conditioning for subjects with a hematologic malignancy (e.g., lymphoma, leukemia, myeloma) comprises administration daily for two to five days of cyclophosphamide (CY) at 30-60 mg/kg alone or CY at 30-60 mg/kg and fludarabine (Flu) at 25-30 mg/m².

In certain embodiments, a biological sample of the aforementioned methods is obtained from the subject within 12 hours, 24 hours, 36 hours, or 48 hours after cellular immunotherapy, preferably within 36 hours. In further embodiments, a classification tree model is used to diagnose or detect the risk of an adverse event associated with cellular immunotherapy. An exemplary classification tree model is described in Example 9 and illustrated in FIG. 7. In some embodiments, measured adverse event biomarker comprises the subject's temperature of at least about 38.5° C., at least about 39° C. or more, the level of IL-6 is at least 12 pg/mL to at least 16 pg/mL, and the level of CCL2 is at least 1,300 pg/mL to at least 1,350 pg/mL.

In further embodiments, the present disclosure provides methods for diagnosing or detecting the risk of an adverse event associated with cellular immunotherapy that further comprises measuring the level of a biomarker of endothelial activation. Exemplary biomarkers of endothelial activation for use this method can be selected from angiopoietin-2, angiopoietin-1, VCAM-1, von Willebrand factor antigen (vWF Ag), asymmetric dimethyl arginine (ADMA), IL-8, CCL26, endothelin-1, osteoprotegerin, CD142 tissue factor, C-reactive protein, E-selectin, P-selectin, P-selectin cofactor CD63/LAMP3, PAI-1, α-fucosyltransferase VI, circulating endothelial cells, endothelial microparticles, or any combination thereof. In particular, embodiments, the biomarker of endothelial activation comprises a component of endothelial Weibel-Palade bodies selected from angiopoietin-2, vWF Ag, IL-8, CCL26, endothelin-1, osteoprotegerin, CD142 tissue factor, P-selectin, P-selectin cofactor CD63/LAMP3, PAI-1, α-fucosyltransferase VI, or any combination thereof.

In certain embodiments, biomarkers of endothelial activation include one or more components from endothelial Weibel-Palade bodies, such as angiopoietin-2, vWF Ag, IL-8, CCL26, endothelin-1, osteoprotegerin, CD142 tissue factor, P-selectin, P-selectin cofactor CD63/LAMP3, PAI-1, α-fucosyltransferase VI, or any combination thereof. In particular embodiments, the biomarker of endothelial activation measured comprises vWF Ag, angiopoietin-2, angiopoietin-1, VCAM-1, or a combination thereof.

In still further embodiments, the present disclosure provides methods for diagnosing or detecting the risk of an adverse event associated with cellular immunotherapy by measuring the level of at least one biomarker and at least one co-factor to the biomarker, and determining a ratio between the at least two markers. For example, an exemplary method of this disclosure comprises measuring the level of vWF Ag and measuring the activity co-factor ADAMTS13, wherein a ratio of ADAMTS13 to vWF Ag that is reduced as compared to a normal sample identifies the subject as at risk of developing an adverse event associated with cellular immunotherapy. In other embodiments, the method comprises measuring the level of angiopoietin-2, and the co-factor measured comprises measuring angiopoietin-1 level, wherein a ratio of angiopoietin-2 to angiopoietin-1 that is increased as compared to a normal sample identifies the subject as at risk of developing an adverse event associated with cellular immunotherapy. In even more embodiments, the method comprises measuring the level of VCAM-1, and the co-factor measured comprises measuring angiopoietin-1 level, wherein a ratio of VCAM-1 to angiopoietin-1 that is increased as compared to a normal sample identifies the subject as at risk of developing an adverse event associated with cellular immunotherapy.

Any of the aforementioned pre-emptive treatments for the adverse event or altered cellular immunotherapy regimens comprises administering the cellular immunotherapy at a reduced dose, a corticosteroid, an inflammatory cytokine antagonist, an endothelial cell stabilizing agent, or any combination thereof, apply to this method as well.

In any of the aforementioned embodiments, provided herein are methods for diagnosing or detecting the risk of an adverse event associated with cellular immunotherapy, wherein the subject has a hematologic malignancy is selected from Hodgkin's lymphoma, non-Hodgkins lymphoma (NHL), primary central nervous system lymphomas, T cell lymphomas, small lymphocytic lymphoma (SLL), B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma (mucosa-associated lymphoid tissue (MALT) lymphoma), nodal marginal zone B-cell lymphoma, follicular lymphoma, mantle cell lymphoma, diffuse large B-cell lymphoma (DLBCL), mediastinal (thymic) large B-cell lymphoma, intravascular large B-cell lymphoma, primary effusion lymphoma, acute lymphoblastic leukemia (ALL), acute myeloid leukemia (AML), chronic lymphocytic leukemia (CLL), chronic myoblastic leukemia (CML), Hairy cell leukemia (HCL), chronic myelomonocytic leukemia (CMML), juvenile myelomonocytic leukemia (JMML), large granular lymphocytic leukemia (LGL), blastic plasmacytoid dendritic cell neoplasm (BPDCN), Burkitt lymphoma/leukemia, multiple myeloma, Bence-Jones myeloma, non-secretory myeloma, plasmacytoma, amyloidosis, monoclonal gammopathy of unknown significance (MGUS), or Waldenstrom's macroglobulinemia.

In any of the aforementioned embodiments, provided herein are methods for diagnosing or detecting the risk of an adverse event associated with cellular immunotherapy, wherein the adverse event is cytokine release syndrome (CRS), neurotoxicity, or both.

Methods of Treating Subjects at Risk of Adverse Events

In further aspects, the present disclosure provides methods for treating hematologic malignancy in a mammalian subject, the method comprising administering to the subject a pre-emptive treatment, an altered cellular immunotherapy regimen, or both to minimize the risk for a potential adverse event, wherein the subject was identified for pre-emptive treatment by any of the methods described herein to determine the risk of an adverse event associated with cellular immunotherapy in the subject having a hematologic malignancy. In some embodiments, the present disclosure provides methods for treating a hematologic malignancy in a mammalian subject, the method comprising (a) obtaining a result from any of the methods described herein to determine the risk of an adverse event associated with cellular immunotherapy in the subject; and (b) administering to the subject a pre-emptive treatment, an altered cellular immunotherapy regimen, or both to minimize the risk for the potential adverse event. In certain embodiments, the hematologic malignancy that is treated is relapsed, refractory, indolent, or a combination thereof.

In certain embodiments, provided herein are methods for treating a hematologic malignancy in a mammalian subject, wherein the subject has a hematologic malignancy is selected from Hodgkin's lymphoma, non-Hodgkins lymphoma (NHL), primary central nervous system lymphomas, T cell lymphomas, small lymphocytic lymphoma (SLL), B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma (mucosa-associated lymphoid tissue (MALT) lymphoma), nodal marginal zone B-cell lymphoma, follicular lymphoma, mantle cell lymphoma, diffuse large B-cell lymphoma (DLBCL), mediastinal (thymic) large B-cell lymphoma, intravascular large B-cell lymphoma, primary effusion lymphoma, acute lymphoblastic leukemia (ALL), acute myeloid leukemia (AML), chronic lymphocytic leukemia (CLL), chronic myoblastic leukemia (CML), Hairy cell leukemia (HCL), chronic myelomonocytic leukemia (CMML), juvenile myelomonocytic leukemia (JMML), large granular lymphocytic leukemia (LGL), blastic plasmacytoid dendritic cell neoplasm (BPDCN), Burkitt lymphoma/leukemia, multiple myeloma, Bence-Jones myeloma, non-secretory myeloma, plasmacytoma, amyloidosis, monoclonal gammopathy of unknown significance (MGUS), or Waldenstrom's macroglobulinemia.

Therapeutic regimens disclosed herein can comprise a cellular immunotherapy in combination with one or more additional combination or adjunctive therapies. Exemplary additional or adjunctive chemotherapeutic agents include alkylating agents (e.g., cisplatin, oxaliplatin, carboplatin, busulfan, nitrosoureas, nitrogen mustards such as bendamustine, uramustine, temozolomide), antimetabolites (e.g., aminopterin, methotrexate, mercaptopurine, fluorouracil, cytarabine, gemcitabine), taxanes (e.g., paclitaxel, nab-paclitaxel, docetaxel), anthracyclines (e.g., doxorubicin, daunorubicin, epirubicin, idaruicin, mitoxantrone, valrubicin), bleomycin, mytomycin, actinomycin, hydroxyurea, topoisomerase inhibitors (e.g., camptothecin, topotecan, irinotecan, etoposide, teniposide), monoclonal antibodies (e.g., ipilimumab, pembrolizumab, nivolumab, avelumab, alemtuzumab, bevacizumab, cetuximab, gemtuzumab, panitumumab, rituximab, tositumomab, trastuzumab), *vinca* alkaloids (e.g., vincristine, vinblastine, vindesine, vinorelbine), cyclophosphamide, prednisone, leucovorin, oxaliplatin, hyalurodinases, or any combination thereof.

Cytokines and growth factors are further therapeutic agents contemplated by this disclosure and include one or more of TNF, IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IFN, G-CSF, Meg-CSF, GM-CSF, thrombopoietin, stem cell factor, and erythropoietin. Pharmaceutical compositions or combinations in accordance with the disclosure may also include other known angiopoietins, for example Ang-1, Ang-2, Ang-4, Ang-Y, or the human angiopoietin-like polypeptide, or vascular endothelial growth factor (VEGF). Growth factors for use in pharmaceutical compositions of this disclosure include angiogenin, bone morphogenic protein-1, bone morphogenic protein-2, bone morphogenic protein-3, bone morphogenic protein-4, bone morphogenic protein-5, bone morphogenic protein-6, bone morphogenic protein-7, bone morphogenic protein-8, bone morphogenic protein-9, bone morphogenic protein-10, bone morphogenic protein-11, bone morphogenic protein-12, bone morphogenic protein-13, bone morphogenic protein-14, bone morphogenic protein-15, bone morphogenic protein receptor IA, bone morphogenic protein receptor IB, brain derived neurotrophic factor, ciliary neutrophic factor, ciliary neutrophic factor receptor α, cytokine-induced neutrophil chemotactic factor 1, cytokine-induced neutrophil chemotactic factor 2α, cytokine-induced neutrophil chemotactic factor 2β, β endothelial cell growth factor, endothelin 1, epidermal growth factor, epithelial-derived neutrophil attractant, fibroblast growth factor (FGF) 4, FGF 5, FGF 6, FGF 7, FGF 8, FGF 8b, FGF 8c, FGF 9, FGF 10, FGF acidic, FGF basic, glial cell line-derived neutrophic factor receptor α1, glial cell line-derived neutrophic factor receptor α2, growth related protein, growth related protein α, growth related protein β, growth related protein γ, heparin binding epidermal growth factor, hepatocyte growth factor, hepatocyte growth factor receptor, insulin-like growth factor I, insulin-like growth factor receptor, insulin-like growth factor II, insulin-like growth factor binding protein, keratinocyte growth factor, leukemia inhibitory factor, leukemia inhibitory factor receptor α, nerve growth factor, nerve growth factor receptor, neurotrophin-3, neurotrophin-4, placenta growth factor, placenta growth factor 2, platelet derived endothelial cell growth factor, platelet derived growth factor, platelet derived growth factor A chain, platelet derived growth factor AA, platelet derived growth factor AB, platelet derived growth factor B chain, platelet derived growth factor BB, platelet derived growth factor receptor α, platelet derived growth factor receptor β, pre-B cell growth stimulating factor, stem cell factor, stem cell factor receptor, transforming growth factor α, transforming growth factor β, transforming growth factor β1, transforming growth factor β1.2, transforming growth factor β2, transforming growth factor β3, transforming growth factor β5, latent transforming growth factor β1, transforming growth factor β binding protein I, transforming growth factor β binding protein II, transforming growth factor β binding protein III, tumor necrosis factor receptor type I, tumor necrosis factor receptor type II, urokinase-type plasminogen activator receptor, vascular endothelial growth factor, and chimeric proteins and biologically or immunologically active fragments thereof.

In certain embodiments, a combination or adjunctive therapy further or alternatively comprises one or more of chemotherapy, a biologic therapy, a hormonal therapy, or any combination thereof.

In certain embodiments, a biologic therapy includes an antibody, an scFv, a nanobody, a fusion protein (e.g., chimeric antigen receptor (CAR), such as used in adoptive immunotherapy comprising a T cell expressing an antigen specific CAR on its cell surface), a tyrosine kinase inhibitor, an immunoreactive T cell, an immunoreactive Natural Killer cell (NKC), or any combination thereof. In certain further embodiments, an antibody comprises ipilimumab, pembrolizumab, nivolumab, avelumab, cetuximab, trastuzumab, bevacizumab, alemtuzumab, gemtuzumab, panitumumab, rituximab, tositumomab, or any combination thereof.

To practice coordinate administration of therapies of this disclosure, therapy regimens combine cellular immunotherapy (e.g., CAR-modified T cell) with an additional or adjunctive therapy simultaneously or sequentially in a coordinated treatment protocol. For example, a therapy regimen may combine a conditioning procedure with a cellular immunotherapy and an optional combination therapy comprising chemotherapy, radiation therapy or the like. In this example, an optional combination therapy may comprise one or more chemotherapeutic agents to be administered concurrently or sequentially, in a given order or otherwise with a conditioning regimen, a cellular immunotherapy, or both.

A coordinate administration of one or more therapies or agents may be done in any order, and there may be a time period while only one or both (or all) therapies, individually or collectively, exert their biological activities. A distinguishing aspect of all such coordinate treatment methods is that a treatment regimen elicits some favorable clinical response, which may or may not be in conjunction with a secondary clinical response provided by an additional therapeutic agent or process. For example, the coordinate administration of a cellular immunotherapy with a combination therapy as contemplated herein can yield an enhanced (e.g., synergistic) therapeutic response beyond the therapeutic response elicited by any of the therapies alone.

For the purposes of administration, the compounds of the present disclosure may be administered as a raw chemical or may be formulated as pharmaceutical compositions. Pharmaceutical compositions of the present disclosure may comprise a small molecule, chemical entity, nucleic acid molecule, peptide or polypeptide (e.g., antibody), and a pharmaceutically acceptable carrier, diluent or excipient.

The small molecule, chemical entity, nucleic acid molecule, peptide or polypeptide composition will be in an amount that is effective to treat a particular disease or condition of interest—that is, in an amount sufficient for reducing the risk of or treating a hyperproliferative disease, such as hematologic malignancies or any of the other associated indications described herein, and preferably with acceptable toxicity to a patient. Compounds for use in the methods described herein can be determined by one skilled in the art, for example, as described in the Examples below. Appropriate concentrations and dosages can be readily determined by one skilled in the art.

Administration of the cells and compounds, or their pharmaceutically acceptable salts, in pure form or in an appropriate pharmaceutical composition, of this disclosure can be carried out using any mode of administration for agents serving similar utilities. The pharmaceutical compositions of this disclosure can be prepared by combining a cell or compound of this disclosure with an appropriate pharmaceutically acceptable carrier, diluent or excipient, and compounds may be formulated into preparations in solid, semi-solid, liquid or gaseous forms, such as tablets, capsules, powders, granules, ointments, solutions, suppositories, injections, inhalants, gels, microspheres, and aerosols. Exemplary routes of administering such pharmaceutical compositions include oral, topical, transdermal, inhalation, parenteral, sublingual, buccal, rectal, vaginal, and intranasal.

The term "parenteral" as used herein includes subcutaneous injections, intravenous, intramuscular, intrasternal injection or infusion techniques. Pharmaceutical compositions of this disclosure are formulated to allow the active ingredients contained therein to be bioavailable upon administration of the composition to a patient. Compositions that will be administered to a subject or patient take the form of one or more dosage units, where for example, a tablet may be a single dosage unit, and a container of a compound of this disclosure in aerosol form may hold a plurality of dosage units. Actual methods of preparing such dosage forms are known, or will be apparent, to those skilled in this art (see, e.g., *Remington: The Science and Practice of Pharmacy,* $22^{nd}$ Edition (Pharmaceutical Press, 2012). The composition to be administered will, in any event, contain a therapeutically effective amount of a compound of this disclosure, or a pharmaceutically acceptable salt thereof, for reducing the risk of or treating pancreatic cancer, metastases arising from the pancreatic cancer, a pancreatic cancer precursor lesion, a metastatic niche associated with pancreatic cancer or other condition of interest in accordance with the teachings of this disclosure.

As a solid composition for oral administration, the pharmaceutical composition may be formulated into a powder, granule, compressed tablet, pill, capsule, chewing gum, wafer or the like form. Exemplary solid compositions can contain one or more inert diluents or edible carriers. In addition, one or more additives may be present, including binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; or a coloring agent. When a pharmaceutical composition is in the form of a capsule, such as a gelatin capsule, it may contain, in addition to materials of the above type, a liquid carrier such as polyethylene glycol or oil or combinations thereof.

The pharmaceutical composition may be in the form of a liquid, such as an elixir, syrup, solution, emulsion, or suspension. In certain embodiments, a liquid composition may be formulated for oral administration or for delivery by injection, as two examples. When intended for oral administration, exemplary compositions may further contain, in addition to one or more compounds of this disclosure, a sweetening agent, preservative, dye/colorant, flavor enhancer, or any combination thereof. Exemplary compositions intended for administration by injection may further contain a surfactant, preservative, wetting agent, dispersing agent, suspending agent, buffer, stabilizer, isotonic agent, or any combination thereof.

Liquid pharmaceutical compositions of this disclosure, whether they are solutions, suspensions or other like forms, may further comprise adjuvants, including sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid (EDTA); buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A pharmaceutical composition of this disclosure may be intended for topical administration, in which case the carrier may comprise a suitable solution, emulsion, ointment, gel base, or any combination thereof. The base, for example, may comprise petrolatum, lanolin, polyethylene glycols, bee wax, mineral oil, diluents such as water and alcohol, emulsifiers, stabilizers, or any combination thereof. Thickening agents may be present in a pharmaceutical composition of this disclosure for topical administration. If intended for transdermal administration, the composition may include a transdermal patch or iontophoresis device.

A pharmaceutical composition of this disclosure may be intended for rectal administration, in the form, for example, of a suppository, which will melt in the rectum and release the active compound(s). A composition for rectal administration may contain an oleaginous base as a suitable nonirritating excipient. Exemplary bases include lanolin, cocoa butter, polyethylene glycol, or any combination thereof.

A pharmaceutical composition of this disclosure may include various materials that modify the physical form of a solid or liquid dosage unit. For example, a composition may include materials that form a coating shell around the active ingredient(s). Exemplary materials for forming a coating shell may be inert, such as sugar, shellac, or other enteric coating agents. Alternatively, active ingredient(s) may be encased in a gelatin capsule.

In certain embodiments, compounds and compositions of this disclosure may be in the form of a solid or liquid. Exemplary solid or liquid formulations include semi-solid, semi-liquid, suspension, and gel forms. A pharmaceutical composition of this disclosure in solid or liquid form may further include an agent that binds to the compound of this disclosure and thereby assists in the delivery of the compound. Suitable agents that may act in this capacity include a monoclonal or polyclonal antibody, a protein, or a liposome.

A pharmaceutical composition of this disclosure may consist of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols of compounds of this disclosure may be delivered in single phase, bi-phasic, or tri-phasic systems in order to deliver the active ingredient(s). Delivery of the aerosol includes the necessary container, activators, valves, subcontainers, and the like, which together may form a kit.

Pharmaceutical compositions of this disclosure may be prepared by methodology well known in the pharmaceutical art. For example, a pharmaceutical composition intended to be administered by injection can be prepared by combining a compound of this disclosure with sterile, distilled water to form a solution. A surfactant may be added to facilitate the formation of a homogeneous solution or suspension. Surfactants are compounds that non-covalently interact with the compound of this disclosure to facilitate dissolution or homogeneous suspension of a compound in an aqueous delivery system.

Cells and compounds, or their pharmaceutically acceptable salts, of this disclosure are administered in a therapeutically effective amount, which will vary depending upon a variety of factors including the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy. Following administration of therapies according to the formulations and methods of this disclosure, test subjects will exhibit about a 10% up to about a 99% reduction in one or more symptoms associated with the disease or disorder being treated (e.g., pancreas cancer), as compared to placebo-treated or other suitable control subjects.

Cells and compounds, or pharmaceutically acceptable derivatives thereof, of this disclosure may also be administered simultaneously with, prior to, or after administration of one or more other therapeutic agents. Such combination therapy includes administration of a single pharmaceutical dosage formulation which contains a compound of this disclosure and one or more additional active agents, as well as administration of the compound of this disclosure and each active agent in its own separate pharmaceutical dosage formulation. For example, a cellular immunotherapy of this disclosure and another active agent can be administered to the patient together in a single dosage composition, or each agent administered in separate dosage formulations. Where separate dosage formulations are used, the cells and compounds of this disclosure and one or more additional active agents can be administered at essentially the same time, i.e., concurrently, or at separately staggered times, i.e., sequentially; combination therapy is understood to include all these regimens.

In any of the aforementioned embodiments, a biological sample comprises a blood or serum sample.

In any of the aforementioned embodiments, a mammalian subject is a human.

Kits

In another aspect, the present invention provides kits comprising materials useful for carrying out diagnostic methods according to the present disclosure. The diagnosis procedures described herein may be performed by diagnostic laboratories, experimental laboratories, or practitioners. The invention provides kits, which can be used in these different settings. Materials and reagents for characterizing biological samples and diagnosing the risk of an adverse event in a hyperproliferative disease in a subject treated by immunotherapy according to the methods herein may be assembled together in a kit. In certain aspects, a kit comprises at least one reagent that specifically detects levels of one or more biomarkers disclosed herein, and instructions for using the kit according to a method of this disclosure.

Each kit may preferably include the reagent (e.g., primary antibody specific for a biomarker, labeled anti-human immunoglobulin) that renders the procedure specific. Thus, for detecting/quantifying a biomarker, the reagent that specifically detects levels of the biomarker may be an antibody that specifically binds to the antigen of interest. A kit of the present disclosure may further comprise one or more substrates to anchor the antigen binding molecules, including microarray slides, beads, plastic tubes, or other surfaces, one or more antibodies to biomarker, labeling buffer or reagents, wash buffers or reagents, immunodetection buffer or reagents, and detection means. Protocols for using these buffers and reagents for performing different steps of the procedure may be included in the kit. The reagents may be supplied in a solid (e.g., lyophilized) or liquid form. The kits of the present disclosure may optionally comprise different containers (e.g., slide, vial, ampoule, test tube, flask or bottle) for each individual buffer or reagent. Each component will generally be suitable as aliquoted in its respective container or provided in a concentrated form. Other containers suitable for conducting certain steps of the disclosed methods may also be provided. The individual containers of the kit are preferably maintained in close confinement for commercial sale.

In certain embodiments, kits of the present disclosure further include control samples, control slides, or both. Instructions for using the kit, according to one or more methods of this disclosure, may comprise instructions for processing the biological sample obtained from a subject, or for performing the test, instructions for interpreting the results. As well as a notice in the form prescribed by a governmental agency (e.g., FDA) regulating the manufacture, use or sale of pharmaceuticals or biological products.

In another aspect, kits are provided for diagnosing or detecting the risk of an adverse event associated with cellular immunotherapy in a mammalian subject having a hematologic malignancy, comprising:

a binding reagent and detectable agent for measuring the level of a plurality of cytokines selected from IL-6, CCL2, IFN-γ, IL-10, IL-15, IL-2, or any combination thereof, provided that reagents for detecting at least IL-6, CCL2 or both are provided;

optionally a device for measuring the subject's temperature;

an optional binding reagent and detectable agent for measuring the level or activity of a biomarker of endothelial activation selected from angiopoietin-2, VCAM-1, vWF Ag, IL-8, CCL26, endothelin-1, osteoprotegerin, CD142 tissue factor, P-selectin, P-selectin cofactor CD63/LAMP3, PAI-1, α-fucosyltransferase VI, ADAMTS13, angiopoietin-1, or any combination thereof, provided that when the binding reagent for angiopoietin-2 or vWF Ag is present, the kit also contains a reagent for detecting activity of ADAMTS13 or detecting angiopoietin-1, respectively; and optional reagents for performing a binding reaction using the detectable agent, optional instructions for using the binding reagent and the detectable agent;

wherein the subject is identified as at risk of developing an adverse event associated with cellular immunotherapy when the biomarker of endothelial activation is increased as compared to a normal sample; or wherein the subject is identified as at risk of developing an adverse event of cytokine release syndrome (CRS), neurotoxicity, or both after cellular immunotherapy when the subject's temperature is at least 38° C. and the level of IL-6 is increased at least 2- to 5-fold and/or the level of CCL2 is increased at least 5- to 20-fold as compared to a normal sample.

In certain embodiments, the binding reagent comprises a nanobody or a binding fragment thereof, an antibody or a binding fragment thereof, or a T-cell receptor molecule or a binding fragment thereof.

In certain further embodiments, the binding reagent is conjugated to a detectable agent. In certain further embodiments, the binding agent is detectable by one or more of: a colorimetric assay, fluorescence imaging, an enzymatic assay, spectrophotometry, mass spectroscopy, or radiation imaging.

EXAMPLES

Example 1

Experimental Procedures

Patient Characteristics, Lymphodepletion Chemotherapy and CAR-T Cell Infusion

A single center study of neurologic adverse events (AEs) was conducted in 133 patients with relapsed and/or refractory CD19$^+$ B-ALL, NHL and CLL who received lymphodepletion chemotherapy and CD19-specific chimeric antigen receptor (CAR)-modified T cells (CAR-T cell) in a phase 1/2 CAR-T cell dose escalation/de-escalation clinical trial (Turtle et al. I, 2016; Turtle et al. II, 2016). The study was conducted with approval of the Fred Hutchinson Cancer Research Center (FHCRC) institutional review board, and is available at clinicaltrials.gov/ct2/show/NCT01865617. Informed consent was obtained from all patients.

CD19-specific CAR-modified T cells were manufactured as described in Turtle et al. I, 2016; and Turtle et al. II, 2016. In brief, patients underwent leukapheresis to obtain PBMC, from which CD4$^+$ and CD8$^+$ central memory T cell subsets were enriched. Enriched CD4$^+$ and CD8$^+$ central memory T cells were stimulated with anti-CD3/anti-CD28 coated paramagnetic beads and transduced with a lentivirus encoding a CAR comprising a FMC63-derived CD19-specific scFv, a modified IgG4-hinge spacer, a CD28 transmembrane domain, a 4-1BB costimulatory domain, and a CD3ζ signaling domain. A cell surface human EGFRt was also encoded in the lentiviral vector separated from the CAR coding sequence cassette by a T2A ribosomal skip sequence to allow precise enumeration of transduced CD4$^+$ and CD8$^+$ CAR-T cells by flow cytometry. The modified T cells were formulated in a 1:1 ratio of CD3$^+$/CD4$^+$/EGFRt$^+$ T cells to CD3$^+$/CD8$^+$/EGFRt$^+$ T cells for infusion at one of three dose levels (DL) as follows: DL1=2×10$^5$EGFRt$^+$ cells/kg; DL2=2×10$^6$EGFRt$^+$ cells/kg; and DL3=2×10$^7$EGFRt$^+$ cells/ kg. In patients with high circulating tumor burden or severe lymphopenia, selection of bulk CD8+ T cells rather than CD8+ central memory T cells could be performed. Patients received lymphodepletion chemotherapy with a cyclophosphamide-based regimen with or without fludarabine (Table 1), followed 2-4 days later by infusion of the CD19-specific CAR-modified T cells. Delay of CAR-T cell infusion was permitted for patients with clinical conditions (e.g. active and uncontrolled infection) that precluded CAR-T cell infusion at the scheduled time. Examination for neurologic adverse events (AEs) presenting within 28 days after the first CAR-T cell infusion.

TABLE 1

Lymphodepletion Regimens prior to CAR-T Cell Infusion

| Lymphodepletion Regimen | Number of Patients |
| --- | --- |
| Cyclophosphamide 2 g/m² Day 1; Etoposide 200 mg/m² Days 2-4 | 2 |
| Cyclophosphamide 4 g/m² Day 1; Etoposide 200 mg/m² Days 2-4 | 3 |
| Cyclophosphamide 3 g/m² Day 1; Etoposide 200 mg/m² Days 2-4 | 2 |
| Cyclophosphamide 2 g/m² Day 1; Etoposide 200 mg/m² Days 2-4 | 2 |
| Cyclophosphamide 2 g/m² Day 1 | 14 |
| Cyclophosphamide 3 g/m² Day 1 | 2 |
| Cyclophosphamide 4 g/m² Day 1 | 1 |
| Bendamustine 90 mg/m² Day 1-2 | 1 |
| Fludarabine 25 mg/m² Day 1-3 | 2 |
| Cyclophosphamide 30 mg/kg Day 1; Fludarabine 25 mg/m² Day 2-4 | 11 |
| Cyclophosphamide 60 mg/kg Day 1; Fludarabine 25 mg/m² Day 2-4 | 78 |
| Cyclophosphamide 1 g/m² Day 1; Fludarabine 25 mg/m² Day 2-4 | 1 |
| Cyclophosphamide 60 mg/kg Day 1; Fludarabine 25 mg/m² Day 2-6 | 11 |
| Cyclophosphamide 300 mg/m² and Fludarabine 30 mg/m² Day 1-3 | 1 |
| Cyclophosphamide 500 mg/m² and Fludarabine 30 mg/m² Day 1-3 | 2 |
| Total | 133 |

Grading of CRS and Neurotoxicity

The severity of CRS was graded according to consensus criteria (Lee et al., *Blood* 124:188, 2014). Neurologic adverse events (AEs) were graded according to the Common Terminology Criteria of Adverse Events (CTCAE) v4.0.3 and did not contribute to organ toxicity criteria for CRS grading.

Assessment of Neurologic Adverse Events (AEs)

Data were collected by review of the study database and electronic medical record (EMR). Neurologic AEs were prospectively assigned an AE term and severity score according to the NCI Common Terminology Criteria for Adverse Events (CTCAE; v4.03) for each day the neurologic AE was present. Due to the heterogeneous presentation of neurotoxicity, AEs were retrospectively grouped into term subsets (Table 2).

"Delirium" encompassed acute cognitive impairment manifesting as confusion, agitation or difficulty with attention or short-term memory, and was distinguished by preserved alertness from "decreased level of consciousness." Additional AE subsets included "ataxia," "focal weakness," "generalized weakness," "hallucinations," "headache," "ICH," "language disturbance," "oculomotor disorder," "seizure," "stroke," "tremor," "other abnormal movements," and "visual changes." Neurologic AEs not captured in the preceding list were designated "other". The overall neurotoxicity grade assigned for a given patient was the highest grade of all neurologic AEs identified in that patient.

Neuroimaging

Head computed tomography (CT) and brain magnetic resonance imaging (MRI) scans were performed when clinically appropriate using standard clinical sequences. All available imaging was reviewed for this study and retrospectively classified as normal, acutely abnormal or chronically abnormal. Abnormalities presenting within 28 days after CAR-T cell infusion were designated acute when findings were consistent with an acute event (edema, blood, enhancement, or diffusion restriction) and were either new compared to prior imaging or evolved on follow-up. Abnormalities were designated chronic when there were nonspecific white matter changes that are typical sequelae of chemotherapy or age-related microvascular disease, when abnormalities were due to an unrelated prior process, and when findings were stable in baseline or follow-up scans.

Evaluation of Clinical Laboratory Parameters, CAR-T Cell Counts, and Biomarker Concentrations Blood was collected before lymphodepletion, on day 0 before CAR-T cell infusion, and at approximately 1, 3, 7, 10, 14, 21, and 28 days after CAR-T cell infusion. Complete blood counts and laboratory analyses of renal and hepatic function, and coagulation were performed using Clinical Laboratory Improvement Amendments (CLIA)-certified assays in clinical laboratories. The concentrations of cytokines in serum were determined by Luminex assay, according to the manufacturer's instructions, with the exception of angiopoietin (Ang)-1 and Ang-2 concentrations, which were evaluated by an immunoassay-based method (Meso Scale Discovery, Rockville, Md.).[5] The von Willebrand Factor (VWF) concentration in patient serum was measured by sandwich ELISA, as described previously.[6] $CD4^+$ and $CD8^+$ CAR-T cells were identified by flow cytometry as viable $CD45^+/CD3^+/CD4^+/CD8^-/EGFRt^+$ and $CD45^+/CD3^+/CD4^-/CD8^+/EGFRt^+$ events in a lymphocyte forward/side scatter (FS/SS) gate. The absolute $CD4^+$ and $CD8^+$ CAR-T cell counts in blood were determined by multiplying the percentage of $CD4^+$ and $CD8^+$ CAR-T cells, respectively, in a viable $CD45^+$ lymphocyte FS/SS gate by the absolute lymphocyte count established by a complete blood count (CBC) performed on the same day (Turtle et al. I and II, 2016).

Cerebrospinal Fluid (CSF) and Blood Samples

CSF was collected from patients when appropriate for clinical care: before lymphodepletion (Pre), during the presence of acute neurotoxicity (Acute), or when patients had recovered from the acute toxicities associated with CAR-T cell immunotherapy (Recovery, approximately 3 weeks or more after CAR-T cell infusion). $CD4^+$ and $CD8^+$ CAR-modified T cell counts in blood and CSF were evaluated by flow cytometry, as previously described (Turtle et al. I, 2016; and Turtle et al. II, 2016). The absolute CAR-T cell count was determined by multiplying the percentage of CAR-T cells identified by flow cytometry in a lymphocyte FS-SS gate by the absolute lymphocyte count established by automated hemocytometer. Patients with progressive CNS malignancy detected by flow cytometry analysis of CSF were not included in the CSF analyses. Concentrations of all cytokines except Ang-1 and Ang-2 in serum and CSF were evaluated by Luminex assay (Riverside, Calif.), as previously described (Turtle et al. I, 2016; and Turtle et al. II, 2016). Serum Ang-1 and Ang-2 concentrations were evaluated using an immunoassay-based method (Meso Scale Discovery, Rockville, Md.), according to the manufacturer's instructions.

vWF Ag and ADAMTS13 Assays

The vWF antigen (vWF Ag) concentration in patient sera was measured by sandwich ELISA, as previously described (Chung et al., *Blood* 127:637-45, 2016), using polyclonal rabbit anti-human vWF as a capture antibody and horseradish peroxidase (HRP)-conjugated polyclonal rabbit anti-human vWF as a detection antibody (Dako, Troy, Mich.).

The ADAMTS13 protease activity in patient sera was measured using an enzyme-linked assay to evaluate cleavage of a HRP-conjugated peptide from the vWF A2 domain, as previously described (Wu et al., *J. Thromb. Haemost.* 4:129, 2006).

Serum-Induced Activation of Endothelial Cells

Human vascular endothelial cells (HUVECs) (Lonza, Portsmouth, N.H.) were cultured for 7 days in parallel-plate flow chambers coated with rat tail type I collagen. Serum, either from patients or healthy donors, was incubated with HUVECs at 37° C. for 30 minutes under static conditions. The chambers were perfused with PBS to remove serum and then perfused with a suspension of fixed platelets (Dade Behring, Siemens Medical Solutions, Deerfield, Ill.) to decorate vWF strings attached to the surface of the HUVECs. The number and length of the vWF-platelet strings were quantified as string units on 16 random non-overlapping bright field images per chamber, as described in Chung et al., 2016. The values for string units obtained from HUVECs incubated with serum were normalized to those from HUVECs stimulated with phorbol myristate acetate (PMA), which was designated as 100%.

Cytokine Stimulation of Primary Human Brain Pericytes

Primary human brain vascular pericytes were cultured in Specialty Medium (ScienCell Research Laboratories, Carlsbad, Calif.) alone or supplemented with 30 ng/mL IFN-γ (Peprotech, Rocky Hill, N.J.) after 24 and 72 hours. After 96 hours, IL-6 and VEGF concentrations were analyzed in the culture supernatant by Luminex, and PDGFRβ expression (Biolegend, San Diego, Calif.) and cleaved caspase-3 (Cell Signaling, Danvers, Mass.) on pericytes was determined by flow cytometry.

Histology and Immunohistochemistry

Formalin-fixed paraffin-embedded (FFPE) brain tissue blocks were sectioned at 4 μm and mounted on positively charged slides. A hematopathologist, an anatomic transplant pathologist, and a neuropathologist examined hematoxylin and eosin stained slides of available autopsy tissues. Histologic features were identified and graded by consensus.

Immunohistochemistry was performed on brainstem sections of pons at the level of the locus coeruleus using a standard automated immunodetection system with the following antibodies: anti-CD3 (Ventana, Tucson, Ariz.), anti-CD8 (Ventana), CD31 (Dako), CD61 (Ventana), CD68 (Dako), CD79a (Dako), and vWF Ag (Dako). Appropriate positive and negative controls were included with each antibody run.

Statistical Methods of Neurotoxicity

Descriptive statistics are reported for key variables. Kruskal-Wallis test, Wilcoxon signed-rank test and Fisher's Exact test were used to compare variables among categories of neurotoxicity. All p-values reported were two-sided without adjustments for multiple comparisons. Tests were generally performed at a significance level of 0.05. For comparisons at distinct time points in longitudinal analyses of laboratory parameters, vital signs and cytokines, the significance level was set at 0.005, given the number of comparisons. The visit windows in the kinetic plots were chosen based on the schedule of visits according to the clinical trial protocol. If multiple values existed in a visit window, the minimum or maximum value in the window was used. Furthermore, stepwise multivariable proportional odds models were performed to assess impact of baseline variables on occurrence of neurotoxicity. Cumulative incidence curves were created for grade 1-5 and for grade 3-5 neurological AEs. Statistical analyses were performed using SAS (version 9.4; SAS Institute Inc.) and classification tree models were performed using AV (version 13.0; SAS Institute Inc.).

Statistical Analysis of CRS

Descriptive statistics are reported for key variables. Fisher's exact test, Kruskal-Wallis test, and Wilcoxon test were used to compare categorical and continuous variables among grades of CRS. Stepwise multivariable proportional odds models were performed to assess the impact of baseline factors on the occurrence of CRS (grade 0 vs 1-3 vs 4-5). Logistic regression was used to evaluate the association between peak CAR-T cell counts after infusion and the probability of CRS, neurotoxicity, and disease response. Data was censored at the time of a second CAR-T cell infusion in 15 of 133 patients who received a second CAR-T cell infusion without additional lymphodepletion chemotherapy approximately 14 days after the first CAR-T cell infusion.

Statistical Analyses of Key Variables

Descriptive statistics are reported for key variables. Cumulative incidence curves for onset of the first fever (temperature ≥38° C.), and the first neurotoxicity event were constructed. Fisher's exact test, Kruskal-Wallis test, and Wilcoxon test was used to compare categorical and continuous variables among categories of CRS. Stepwise multivariable proportional odds models were performed to assess impact of baseline factors on the occurrence of CRS (grade 0 vs 1-3 vs 4-5). Logistic regression was used to estimate the probability of the occurrence of CRS or neurotoxicity, and disease response with peak CAR-T cell counts within the first 30 days. Log10 values were used to transform data as appropriate, with 0.001 substituting for values of 0. Tests were generally performed at a significance level of 0.05. All p-values reported were two-sided without adjustments for multiple comparisons.

The mean±standard error of mean (SEM) of the observed values for each laboratory parameter were plotted over time. The time points in the plots were chosen based on the schedule of visits according to the clinical trial protocol. If multiple values existed in a visit window, the minimum or maximum value in the window was used. For comparisons at distinct time points, the significance level was set at 0.005, given the number of comparisons.

Statistical analyses were performed using SAS (version 9.4; SAS Institute Inc.) and classification tree models were performed using JMP (version 13.0; SAS Institute Inc.).

Example 2

Figure 1B:
Figure 1C:
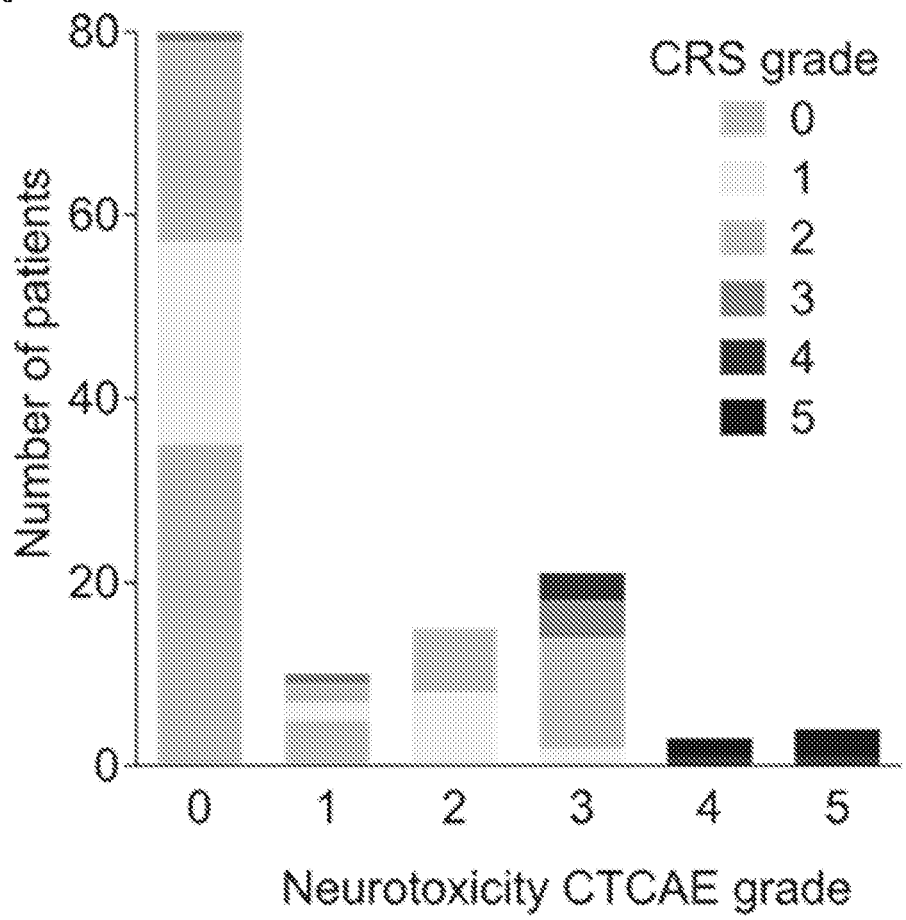

Neurologic Adverse Events (AES) after Immunotherapy with CD19-Specific CAR-Modified T Cells Neurologic adverse events (AEs) were studied in a cohort of 133 adults who received lymphodepletion chemotherapy and CD19-specific CAR-T cells to treat refractory B-ALL, NHL or CLL. Within 28 days of CD19-specific CAR-T cell infusion, 40% of patients (53/133) had one or more grade ≥1 neurologic AEs (40%; 19% grade 1-2; 16% grade 3; 2% grade 4; 3% grade 5), presenting a median of 4 days after CAR-T cell infusion (FIGS. 1A and 1B). The median time from onset to the highest neurotoxicity grade was 1 day (range 0-19) and the median duration of reversible neurologic AEs was 5 days (range 1-70 days). Forty-eight of 53 patients with any neurologic AE (91%) also had cytokine release syndrome (CRS) (FIG. 1C). Five patients with neurologic AEs (13%) did not develop CRS; however, all neurologic AEs in patients without CRS were mild (grade 1), subjective, and transient. CRS with fever (≥38° C.) preceded the onset of neurotoxicity in all patients who developed grade ≥3 neurotoxicity (n=28). In patients who also develetiology of language disturbance. Focal neurologic deficits, ataxia, and other abnormal movements were infrequent. Seizures occurred in 4 of 53 patients (8%). Seizures in 2 patients with grade 5 neurotoxicity occurred in the absence of a prior seizure history. The other two patients were among 6 in the study with an antecedent seizure history. Intracranial hemorrhage (ICH) was rare (1 of 53; 2%) and ischemic stroke was not observed.

TABLE 2

Neurologic Adverse Event Terms[a,b]

| | CTCAE Grade | | | | | |
|---|---|---|---|---|---|---|
| Term | 1 (Mild) N = | 2 (Moderate) N = | 3 (Severe) N = | 4 (Life Threatening) N = | 5 (Death) | TOTAL[B] |
| Delirium | 9 | 4 | 20 | 2 | — | 35 (66%) |
| Headache | 13 | 13 | 3 | — | — | 29 (55%) |
| Language Disturbance | 3 | 6 | 9 | — | — | 18 (34%) |
| Decreased Level of Consciousness | 2 | 2 | 3 | 6 | — | 13 (25%) |
| Tremor | 7 | 3 | 0 | — | — | 10 (19%) |
| Focal Weakness | 2 | 2 | 1 | 1 | — | 6 (11%) |
| Hallucinations | 2 | 1 | 1 | — | — | 4 (8%) |
| Seizure | — | 2 | 2 | 0 | — | 4 (8%) |
| Other Abnormal Movements | 2 | 1 | 0 | — | — | 3 (6%) |
| Visual Changes | 1 | 2 | 0 | — | — | 3 (6%) |
| Ataxia | 0 | 0 | 2 | — | — | 2 (4%) |
| Generalized Weakness | 0 | 1 | 1 | 0 | — | 2 (4%) |
| Cerebral Edema | — | — | — | 0 | 2 | 2 (4%) |
| Oculomotor Disorder | 1 | 0 | 0 | — | — | 1 (2%) |
| Intracranial Hemorrhage | 0 | 0 | 0 | 0 | 1 | 1 (2%) |
| Cortical Laminar Necrosis[c] | 0 | 0 | 0 | 0 | 1 | 1 (2%) |

Figures 1D, 1E, 1F:
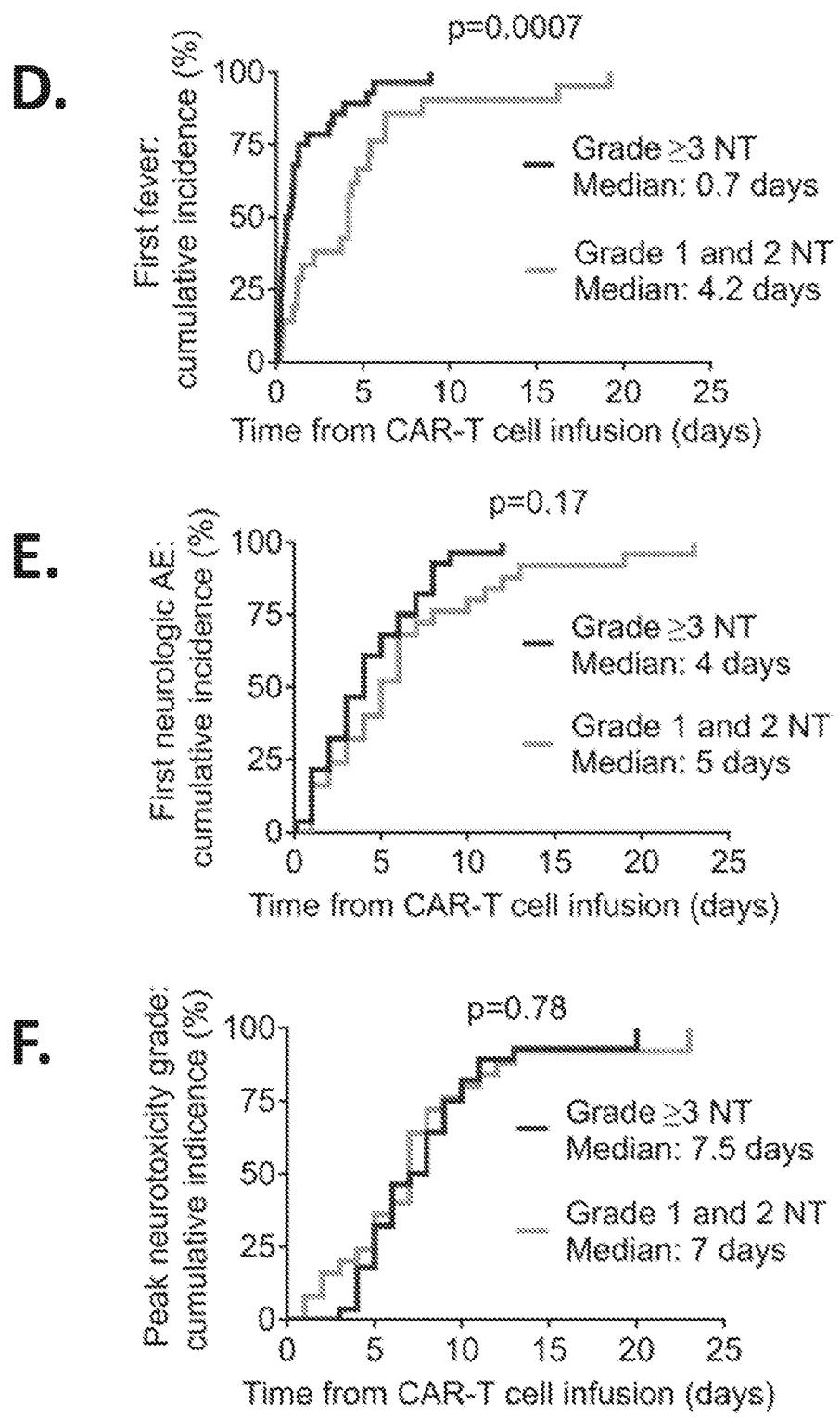
Figure 1G:
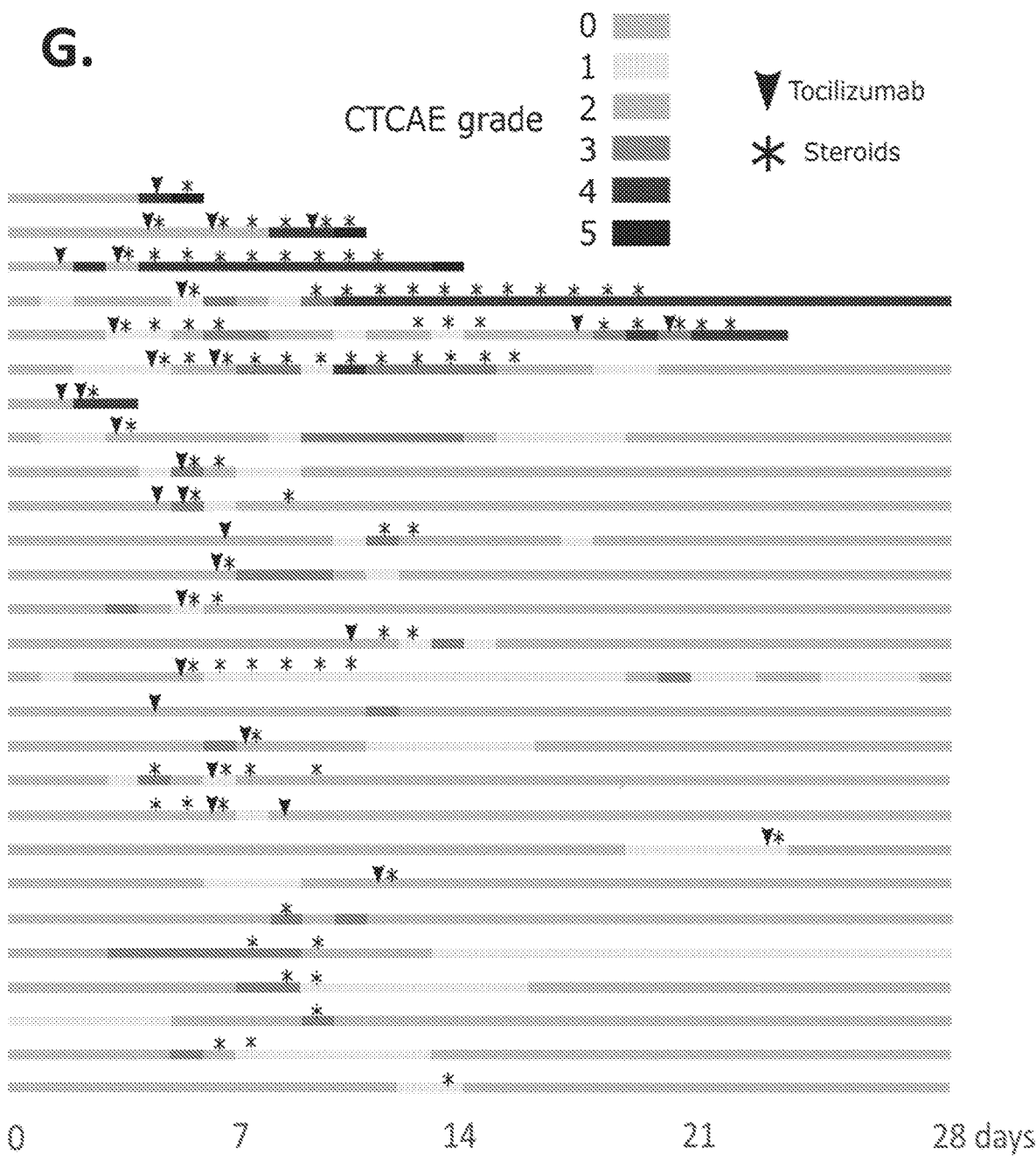
Figures 2A, 2B, 2C, 2D, 2E, 2F, 2G, 2H, 2I:
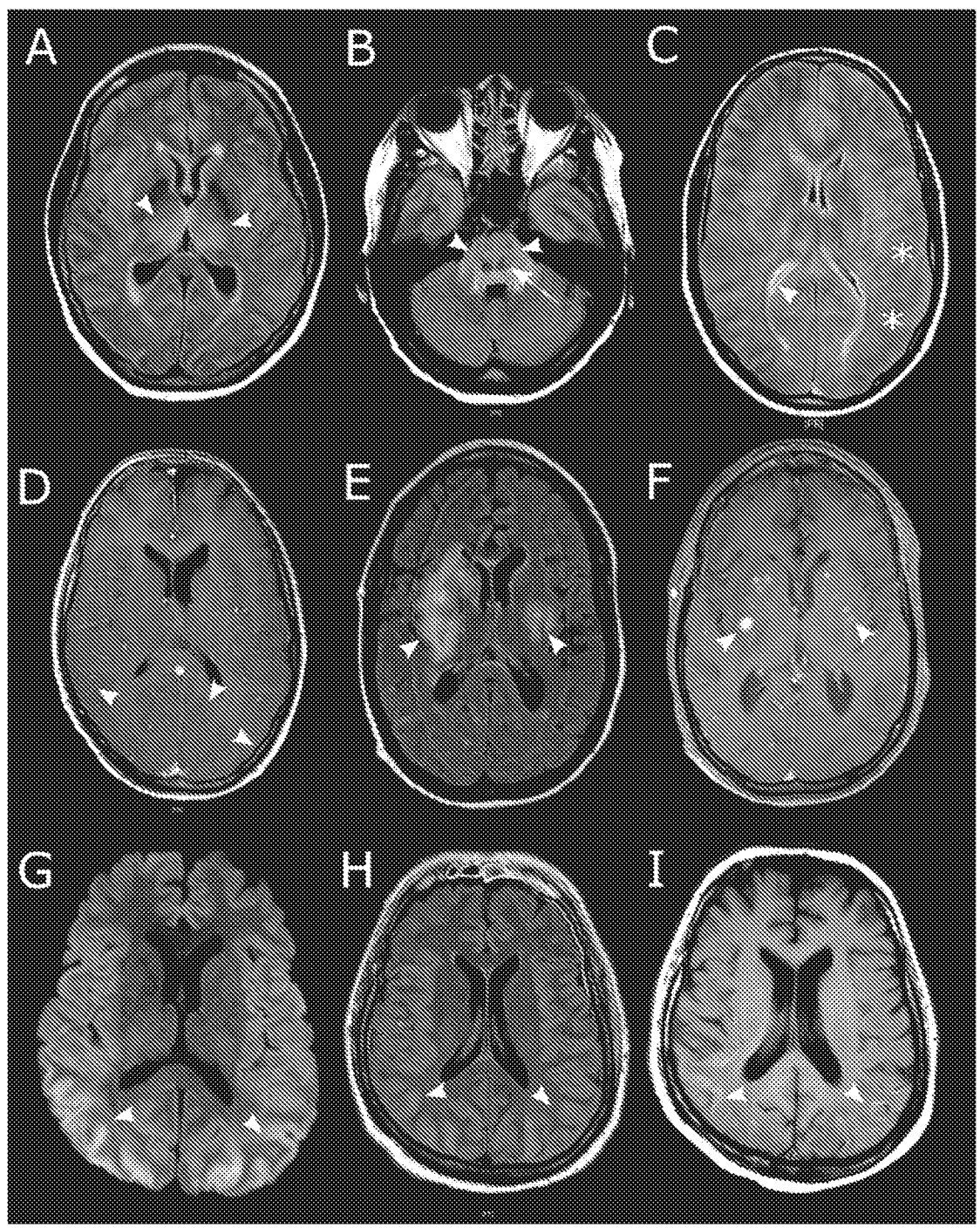
FIGS. 2A-2I. Brain magnetic resonance imaging (MRI) findings in patients with severe neurotoxicity after CD19 CAR-T cell immunotherapy. Symmetric edema of deep structures in a patient with grade 5 neurotoxicity has FLAIR hyperintensities that were seen in the bilateral thalami (A) and the pons (B, arrowheads), consistent with vasogenic edema. Punctate hemorrhages in the most affected areas are seen as T2 dark lesions (B, arrow). (C) Global edema with blurring of the gray-white junction (stars) and slit-like ventricles on FLAIR imaging in a patient with grade 5 neurotoxicity. (D) Diffuse leptomeningeal enhancement in a patient with grade 5 neurotoxicity. White matter FLAIR hyperintensities (E) that in some cases were contrast enhancing (F; T1+gadolinium) in a patient with grade 3 neurotoxicity without focal neurologic deficits on exam. Cytotoxic edema of the cortical ribbon is seen on diffusion weighted imaging (G) and concomitant cortical swelling on FLAIR (H). In the same patient, injury progressed to irreversible cortical laminar necrosis indicated by T1 hyperintensities within the cortical ribbon 10 days later (I).

[a]Dashes indicate absence of a grade in the CTCAE.
[b]Number and percentage with each AE term among 53 patients with neurotoxicity.
[c]Cortical laminar necrosis is not included in the CTCAE.

oped CRS, neurotoxicity presented a median of 4.5 days (range 2-17) after the first fever. Fever occurred earlier after CAR-T cell infusion in patients who subsequently developed grade ≥3 neurotoxicity compared to those who developed grade 1-2 neurotoxicity (p=0.0007). However, the time from CAR-T cell infusion to the onset of neurotoxicity (p=0.17) as well as the time to the maximum grade of neurotoxicity (p=0.78) were similar (FIGS. 1D-1F). Together, these data show that early onset of CRS is associated with subsequent development of more severe neurotoxicity.

Among the 53 patients with neurotoxicity the most common finding was delirium with preserved alertness (35 of 53, 66%; Table 2), which was grade ≤2 in 13 of 35 patients (37%), and present for a median of 4 days (range 1-24). Headache was observed in 29 of 53 patients (55%) and was grade ≤2 in 26 of 29 patients (90%), persisting for a median of 3 days (range 1-12). Grade 1-2 headache was the only neurologic AE in 9 patients. A decreased level of consciousness occurred in 13 of 53 patients (25%), and in 6 cases was associated with coma requiring invasive ventilatory support. In those who recovered, the median duration of the decreased level of consciousness was 2 days (range 1-12 days). Language disturbance was observed in 18 of 53 patients (34%) for a median of 4 days (range 1-9) and was accompanied in 15 of 18 patients (83%) by decreased level of consciousness and/or delirium, which complicated the distinction between impaired attention and aphasia as the Among 133 patients treated with lymphodepletion chemotherapy and CD19-specific CAR-modified T cells (CAR-T cells), 7 (5%) developed grade ≥4 neurotoxicity, of whom 6 were treated with CAR-T cell doses that were subsequently determined to be above the maximum tolerated dose for each disease and tumor burden (B-ALL with ≤5% marrow blasts, $2\times10^6$ CAR-T cells/kg; B-ALL with >5% marrow blasts, $2\times10^5$ CAR-T cells/kg; NHL, $2\times10^6$ CAR-T cells/kg; and CLL, $2\times10^6$ CAR-T cells/kg). Four of 133 patients (3%) died due to neurotoxicity: one died from multifocal brainstem hemorrhage and edema associated with DIC, 2 died due to acute cerebral edema, and one developed cortical laminar necrosis with a persistent minimally conscious state until death 4 months after CAR-T cell infusion. With the exception of those with fatal neurotoxicity and one patient in whom a grade 1 neurologic AE resolved 2 months after CAR-T cell infusion, neurotoxicity completely resolved in all patients by day 28 after CAR-T cell infusion (FIG. 1B).

Of the 53 patients with neurotoxicity, 23 underwent brain MRI within 28 days of CAR-T cell infusion. Acute abnormalities on MM were evident in 7 of 23 patients (30%), 4 of whom had fatal neurotoxicity, indicating that an abnormal MM scan during acute neurotoxicity is associated with a high risk of a poor outcome. FLAIR/T2 changes indicative of vasogenic edema, leptomeningeal enhancement, and/or multifocal microhemorrhages were present in a majority of patients with severe neurotoxicity and abnormal MRI scans.

Contrast enhancement, consistent with breakdown of the blood-brain barrier (BBB), was also seen in some FLAIR/T2 lesions (FIGS. 2A-2F). One patient developed extensive cortical diffusion restriction indicative of cytotoxic edema (FIGS. 2G-2I), which appeared distinct from vasogenic edema observed in other patients. None of the other patients had lesions that were diffusion restricting. Electroencephalography (EEG) was performed in 17 of 53 patients during acute neurotoxicity. Diffuse slowing was present in 13 of 17 patients (76%). Focal slowing was noted in one patient (6%) with known epilepsy, and clinical and subclinical seizures were observed in one patient. EEG was normal in 2 of 17 patients (12%).

Example 3

Treatment of Neurotoxicity after Infusion of CD19-Specific CAR-Modified T Cells

Tocilizumab, an antagonistic IL-6R monoclonal antibody, effectively ameliorates fever and hypotension in most patients with severe cytokine release syndrome (CRS) after CD19-specific CAR-T cell (CAR-T cell) therapy, and is frequently administered with or without corticosteroids to patients with neurotoxicity (Turtle et al. I, 2016; Turtle et al. II, 2016). Twenty of 53 patients with neurotoxicity (38%) received tocilizumab (4-8 mg/kg, intravenous (IV)) and dexamethasone (10 mg IV, twice a day (b.i.d.)), one (2%) received tocilizumab alone, and 6 (11%) received dexamethasone alone (FIG. 1E). Fourteen patients received a single dose of tocilizumab, five received two doses, and two received three doses. A median of two doses (range 1-31) of dexamethasone 10 mg IV b.i.d. were administered and one patient received methylprednisolone (1,000 mg IV×9). In 14 of 21 patients (67%), the peak grade of neurotoxicity occurred after the first dose of tocilizumab, and in 8 of those patients neurotoxicity first presented after tocilizumab had been administered for CRS. In patients with reversible neurotoxicity, the time from the first tocilizumab and/or dexamethasone dose to resolution of neurotoxicity (median 4 days, range 1-64 days) was longer than the time to resolution of fever (temperature <38° C. for at least 48 hours, median 0.4 days, range 0-3.8 days, p<0.0001).

These data indicate that established neurotoxicity is less responsive than CRS to interventions that suppress IL-6 activity or CAR-T cell function.

Example 4

Baseline Characteristics Associated with Risk of Neurotoxicity after Infusion of CD19-Specific CAR-Modified T Cells Baseline characteristics of patients receiving CAR-T cell immunotherapy were analyzed to identify factors associated with an increased risk of subsequent neurotoxicity. In univariate analyses (Table 3), neurotoxicity was more frequent in younger patients (p=0.094), those with B-ALL (p=0.084), a high fraction of tumor (p=0.072) and CD19+ cells (p=0.062) in bone marrow, and a high CAR-modified T cell dose (p<0.0001). The presence of any pre-existing neurologic comorbidity was also associated with neurotoxicity (p=0.0059). Only the infused CAR-T cell dose was associated with the occurrence of more severe neurotoxicity (grade ≥3 versus grade 1-2, p=0.014). The selection of CD8+ T cell subset in CAR-T cell manufacturing, the patient's sex and race, the number of prior chemotherapy regimens, previous hematopoietic stem cell transplantation, and pretreatment performance score were not associated with neurotoxicity in univariate analyses.

TABLE 3

| Factors Associated with Neurotoxicity | | | | | | | |
|---|---|---|---|---|---|---|---|
| Neurotoxicity CTCAE Grade | | Grade[a] | | | Total | Univariate[b] | Multi-variable[c] |
| | | 0 | 1-2 | 3-5 | | | |
| Overall, n (%) | | 80 (60) | 25 (19) | 28 (21) | 133 (100) | | |
| Age, n (%) | <40 years | 11 (41) | 10 (37) | 6 (22) | 27 | 0.094 | |
| | 40-60 years | 42 (66) | 8 (13) | 14 (22) | 64 | | |
| | >60 years | 27 (64) | 7 (17) | 8 (19) | 42 | | |
| Sex, n (%) | Male | 59 (63) | 17 (18) | 17 (18) | 93 | 0.4 | |
| | Female | 21 (53) | 8 (20) | 11 (28) | 40 | | |
| Diagnosis, n (%) | ALL | 22 (47) | 11 (23) | 14 (30) | 47 | 0.084 | |
| | CLL | 16 (67) | 2 (8) | 6 (25) | 24 | | |
| | NHL | 42 (68) | 12 (19) | 8 (13) | 62 | | |
| Race, n (%) | White | 62 (57) | 21 (19) | 26 (24) | 109 | 0.17[d] | |
| | Asian | 7 (88) | 1 (13) | 0 | 8 | | |
| | American Indian or Alaska Native | 3 (60) | 1 (20) | 1 (20) | 5 | | |
| | Black or African American | 3 (100) | 0 | 0 | 3 | | |
| | Other | 5 (64) | 2 (25) | 1 (13) | 8 | | |
| Prior Therapies | Median (range) | 4 (1, 11) | 4 (1, 10) | 4 (1, 11) | 4 (1, 11) | 0.5 | |
| Transplant History, n (%) | Auto | 17 (68) | 5 (20) | 3 (12) | 25 | 0.5 | |
| | Allo | 14 (50) | 8 (29) | 6 (21) | 28 | | |

TABLE 3-continued

Factors Associated with Neurotoxicity

| Neurotoxicity CTCAE Grade | | Grade[a] | | | Total | Univariate[b] | Multi-variable[c] |
|---|---|---|---|---|---|---|---|
| | | 0 | 1-2 | 3-5 | | | |
| Karnofsky Score[e], n (%) | 60-70 | 7 (50) | 3 (21) | 4 (29) | 14 | 0.5 | |
| | 80-90 | 65 (61) | 18 (17) | 23 (22) | 106 | | |
| | 100 | 8 (62) | 4 (31) | 1 (8) | 13 | | |
| Pre-Existing Neurologic Comorbidities, n (%) | Any | 26 (45) | 16 (28) | 16 (28) | 58 | 0.0059[g] | 0.0023[g] |
| | PN[f] | 14 (47) | 7 (23) | 9 (30) | 30 | 0.2 | |
| | CNS involvement | 6 (43) | 5 (36) | 3 (21) | 14 | 0.2 | |
| | Headache disorder | 6 (43) | 5 (36) | 3 (21) | 14 | 0.2 | |
| | Other | 5 (50) | 2 (20) | 3 (30) | 10 | 0.7 | |
| | ICH[h] | 4 (67) | 1 (17) | 1 (17) | 6 | 1 | |
| | Seizures | 2 (33) | 2 (33) | 2 (33) | 6 | 0.3 | |
| | Cog impairment[i] | 1 (25) | 2 (50) | 1 (50) | 4 | 0.1 | |
| | MTX CNS toxicity[j] | 1 (50) | 1 (50) | 0 | 2 | 0.4 | |
| Marrow Disease, % | Median (range) | 0.6 (0, 97) | 0.4 (0, 93) | 25.8 (0, 97) | 1.3 (0, 97) | 0.072 | 0.0165 |
| Total CD19+ T Cells In Marrow, % | Median (range) | 5.3 (0, 99) | 12.4 (0, 93) | 29.1 (0, 97) | 8.8 (0, 99) | 0.062 | |
| CD8+ Central Memory Enriched Car-T Cells[k], n (%) | Selected | 48 (67) | 11 (15) | 13 (18) | 72 (54) | 0.242 | |
| Lymphodepletion Regimen[l], n (%) | Cy/Flu | 58 (56) | 23 (22) | 23 (22) | 104 | 0.11 | 0.0259 |
| | Non-Cy/Flu | 22 (76) | 2 (7) | 5 (17) | 29 | | |
| CAR-T Cell Dose, n (%) | $2 \times 10^5$ cells/kg | 20 (57) | 10 (29) | 5 (14) | 35 | <.0001 | 0.0009 |
| | $2 \times 10^6$ cells/kg | 55 (64) | 15 (17) | 16 (19) | 86 | | |
| | $2 \times 10^7$ cells/kg | 5 (42) | 0 | 7 (58) | 12 | | |
| Cytokine Release Syndrome, n (%) | None (G 0) | 35 (88) | 5 (13) | 0 | 40 | <0.0001 | n/a |
| | Mild (G 1-2) | 44 (57) | 19 (25) | 14 (18) | 77 | | |
| | Severe (G 3-5) | 1 (6) | 1 (6) | 14 (88) | 16 | | |

[a]Percentages are shown in parentheses.
[b]Two-sided p-values calculated based on Kruskal-Wallis test for continuous variables, and based on Fisher's Exact test for categorical variables.
[c]Stepwise multivariable proportional odds models were performed to assess the impact of baseline factors on the occurrence of neurotoxicity (grade 0 vs 1-2 vs 3-5), where log10 values were used to transform data as appropriate, with 0.001 substituting for marrow disease values of 0. CRS was not included in the stepwise multivariable model, because it is not a pre-treatment variable; the percentage of all CD19+ cells in bone marrow was not included in the stepwise multivariable model since it strongly correlates with the percentage of marrow CD19+ abnormal B cells (r = 0.99, p < 0.0001). Only variables with a p-value <0.05 were retained in the final model.
[d]White versus non-white
[e]Karnofsky performance score prior to lymphodepletion
[f]Peripheral neuropathy
[g]None versus any
[h]Intracranial hemorrhage
[i]Cognitive impairment
[j]CNS toxicity from prior intra-thecal methotrexate use
[k]CAR-modified T cells manufactured from CD4+ T cells and central memory enriched CD8+ T cells
[l]Cy/Flu regimens include both cyclophosphamide and fludarabine Multivariable analysis showed that preexisting neurologic comorbidities (p=0.0023), along with factors that increase in vivo CAR-T cell proliferation, such as Cy/Flu lymphodepletion (p=0.0259), higher infused CAR-T cell dose (p=0.0009), and higher burden of malignant CD19$^+$ B cells in marrow (p=0.0165) were associated with an increased risk of neurotoxicity (Table 3).

Example 5

Figures 3A, 3B, 3C, 3D:
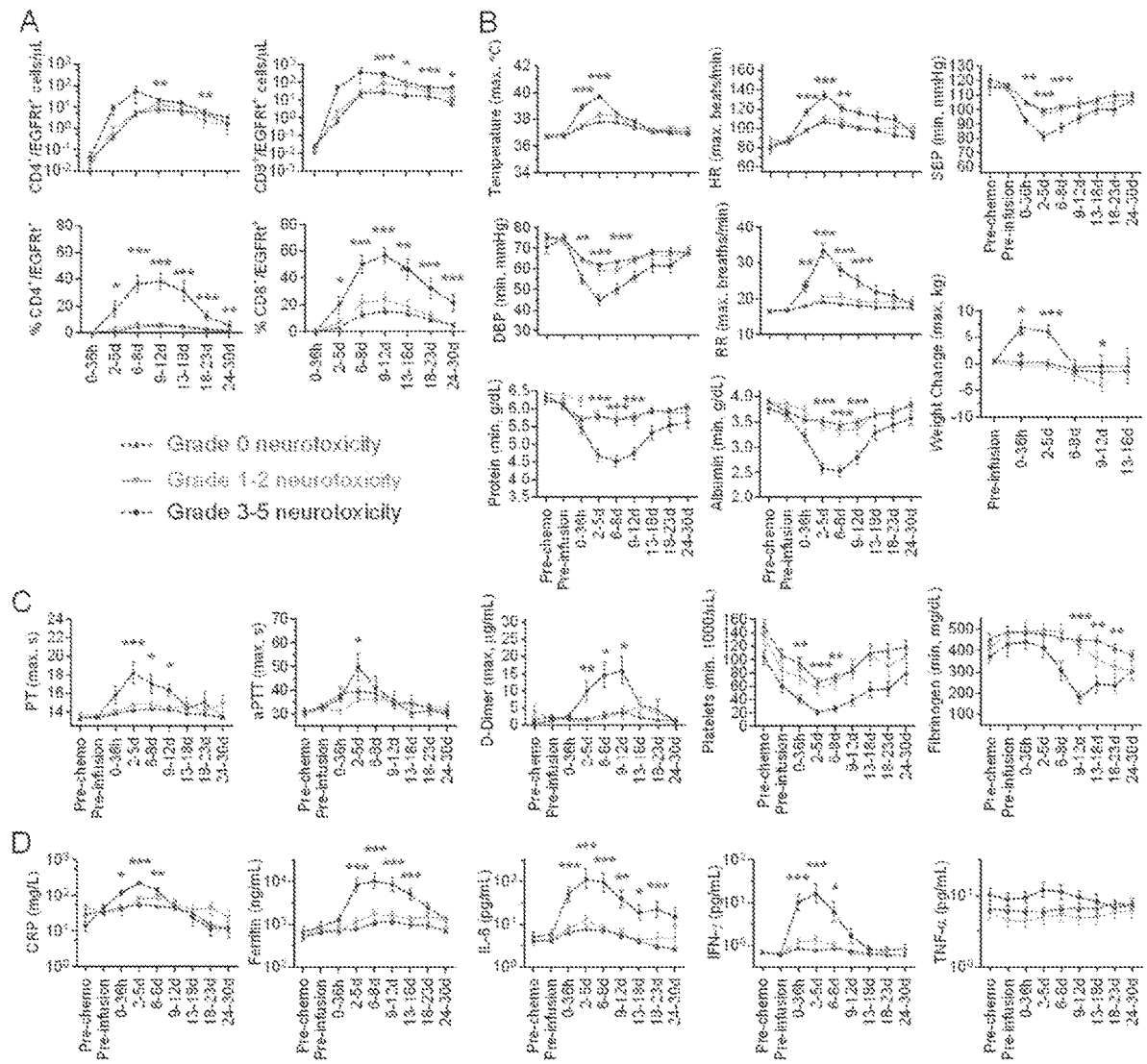
FIGS. 3A-3F. Severe neurotoxicity is associated with vascular dysfunction. (A) Absolute counts of $CD4^+/EGFRt^+$ and $CD8^+/EGFRt^+$ CAR-T cells in blood, and the percentages of $CD4^+/EGFRt^+$ cells within $CD4^+$ T cells and of $CD8^+/EGFRt^+$ cells within $CD8^+$ T cells in the indicated time windows after CAR-T cell infusion are shown in patients without neurotoxicity (grey) or with grade 1-2 (orange) or 3-5 (red) neurotoxicity. (B) Minimum (min) or maximum (max) values of vital signs, serum protein and albumin concentration, and body weight are shown within the indicated time periods. Pre-chemo, before lymphodepletion chemotherapy. Pre-infusion, before CAR-T cell infusion. SBP, systolic blood pressure. DBP, diastolic blood pressure. HR, heart rate. RR, respiratory rate. (C) Minimum (min) or maximum (max) values of coagulation parameters are shown within the indicated time periods. PT, prothrombin time. APTT, activated partial thromboplastin time. (D) Maximum serum CRP, ferritin, IFN-γ, IL-6, and TNF-α concentrations within indicated time periods are shown, according to severity of neurotoxicity. Within each time window in all figures, the y-axis shows the mean+/−standard error of the mean (SEM) of the values for all patients. $*0.001<p<0.005$, $0.0001<p<0.001$, $*p<0.0001$ for the indicated time points for the comparison of grade 0 vs 1-2 vs 3-5 neurotoxicity. P values for TNF-α at 0-36 hours and 2-5 days after CAR-modified T cell infusion were 0.038 and 0.022, respectively. (E) Maximum serum cytokine concentrations within the indicated time periods are shown according to severity of neurotoxicity. Data represent the mean+/−standard error of the mean (SEM). $*0.001<p<0.005$, $0.0001<p<0.001$, $*p<0.0001$ at the indicated time points for the comparison of grade 0 vs 1-2 vs 3-5 neurotoxicity. (F) The maximum serum IL-6 concentration and the day after CAR-T cell infusion at which the maximum IL-6 concentration was reached are shown for patients with grade 1-2 (yellow), 3 (orange) or 4-5 (red) neurotoxicity. All patients with a serum IL-6 concentration above 501 pg/mL (horizontal line) within the first 6 days after CAR-modified T cell infusion developed grade ≥4 neurotoxicity.
Figure 3E:
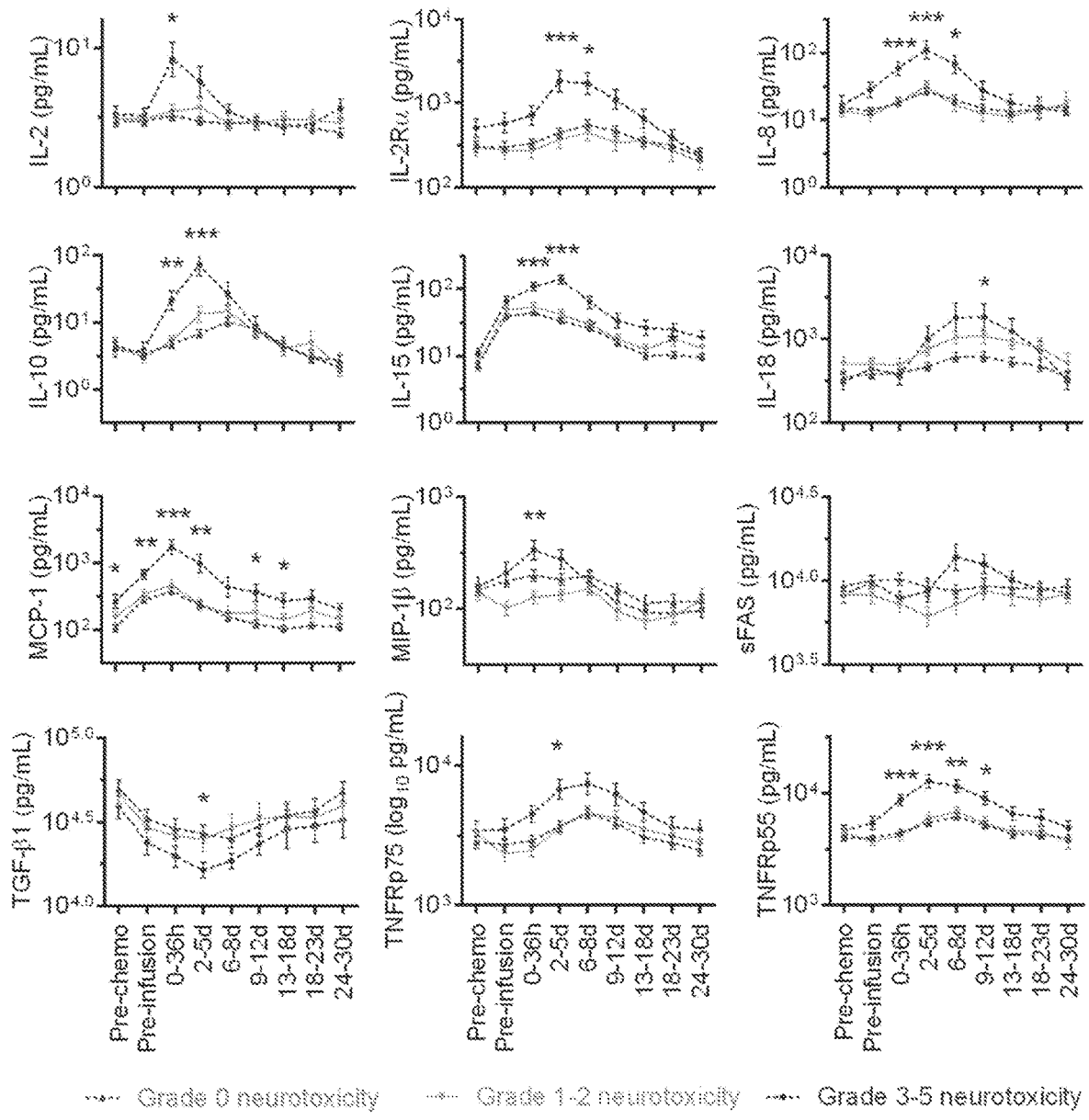
Figure 3F:
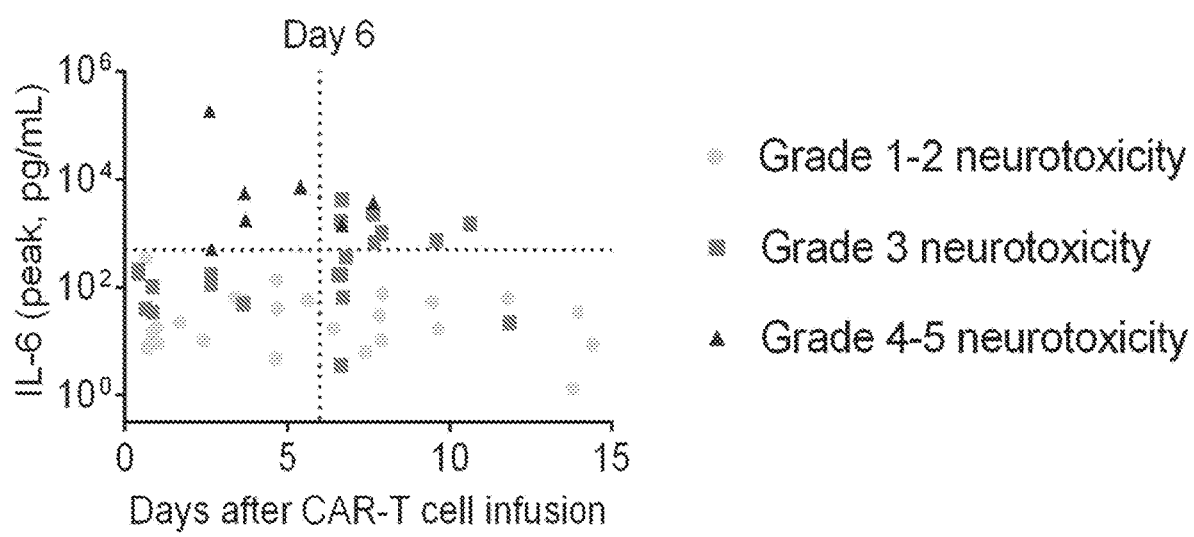

Severe Neurotoxicity Associated with Severe Cytokine Release Syndrome and Systemic Vascular Dysfunction Consistent with the baseline factors that were associated with more severe neurotoxicity, patients who developed grade ≥3 neurotoxicity were found to have more severe CRS (p<0.0001; FIG. 1C), and earlier and greater CD4$^+$ and CD8$^+$ CAR-T cell expansion in blood compared to those with grade ≤2 neurotoxicity (FIG. 3A). Patients with grade ≥3 neurotoxicity also had earlier and higher fever, more severe vascular instability and tachypnea, more severe hypoproteinemia, hypoalbuminemia and weight gain, consistent with loss of vascular integrity and systemic capillary leak (FIG. 3B). Severe neurotoxicity was also accompanied by disseminated intravascular coagulation (DIC), with elevated prothrombin time (PT), activated partial thromboplastin time (aPTT) and d-dimer beginning 2-5 days after CAR-T cell infusion, prolonged thrombocytopenia, and a late reduction in fibrinogen to a nadir approximately 1-2 weeks after CAR-T cell infusion (FIG. 3C). The severity of neurotoxicity correlated with higher peak concentrations of CRP, ferritin, and multiple cytokines, including those that activate endothelial cells, such as IL-6, IFN-γ, and TNF-α (FIGS. 3D and 3E). In line with the association between early onset CRS and later development of severe neurotoxicity (FIG. 1D), an earlier peak of IL-6 serum concentration was associated with a higher risk of grade ≥4 neurotoxicity (FIG. 3F). Within the first 6 days after infusion of CAR-modified T cells, 5 of 5 patients (100%) with an IL-6 concentration ≥501 pg/mL developed grade ≥4 neurotoxicity, whereas only 2 of 11 patients (18%) who reached the same serum IL-6 concentration more than 6 days after CAR-T cell infusion developed grade ≥4 neurotoxicity.

These data indicate that neurotoxicity is associated with early onset of high concentrations of serum cytokines and vascular dysfunction.

Example 6

Figures 4A, 4B, 4C, 4D, 4E, 4F:
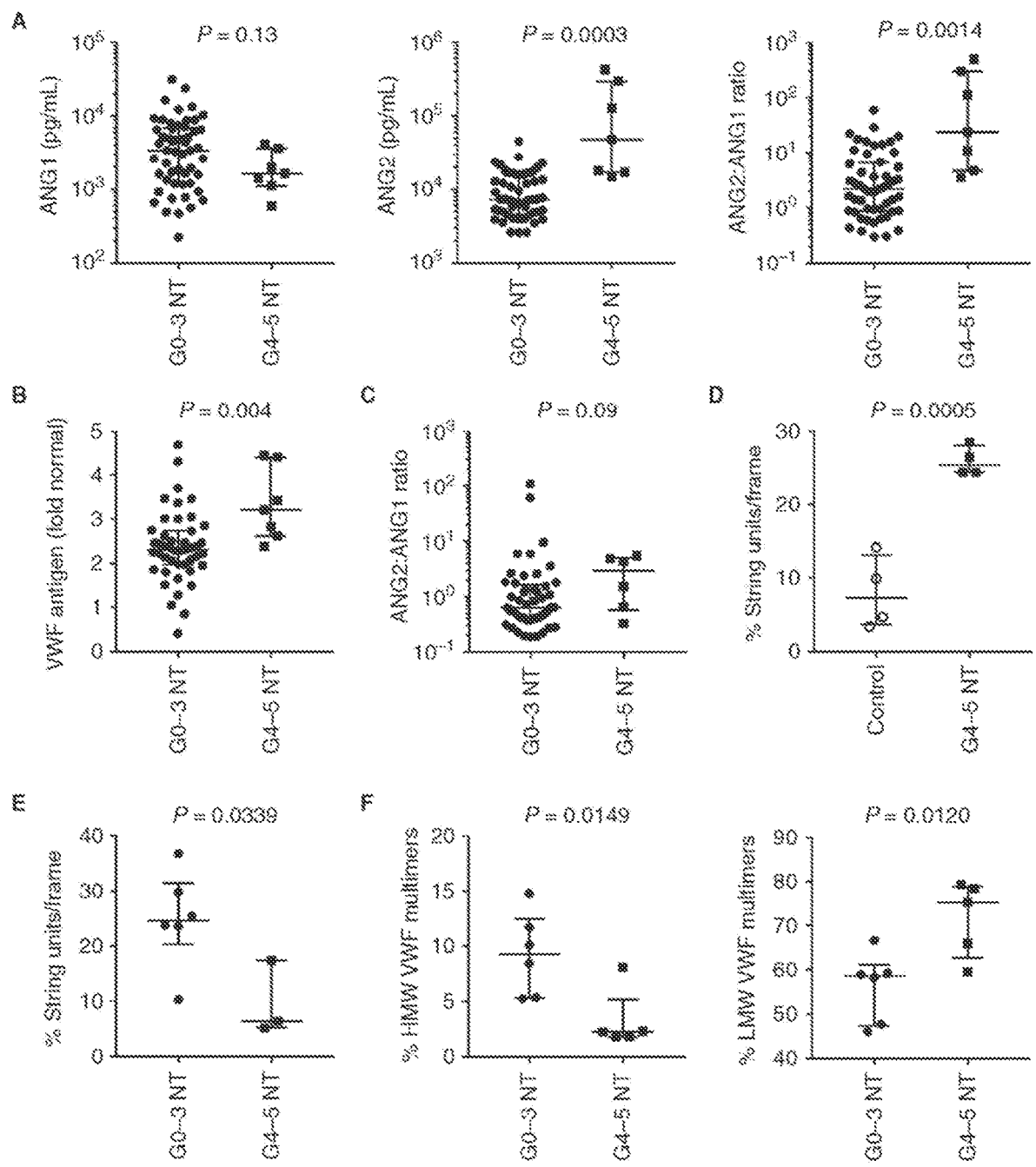
FIGS. 4A-4F. Endothelial activation in neurotoxicity associated with CD19 CAR-T cell immunotherapy. (A) Ang-1 (left) and Ang-2 (center) concentrations and the Ang-2:Ang-1 ratio (right) in serum collected approximately 7 days after CAR-T cell infusion from a subset of patients with grade 0-3 (n=52) or ≥4 (n=7) neurotoxicity. The median (bar) and interquartile range are shown. Each point represents data from one patient. (B) vWF Ag concentration in serum from patients with grade 0-3 (n=45) or grade ≥4 (n=7) neurotoxicity. Serum was collected approximately 1 week after CAR-T cell infusion. Data represent the fold change from the vWF concentration in normal reference plasma (CRYOcheck, Precision Biologic, Dartmouth, NS, Canada; vWFAg 12.2 μg/mL). (C) Ang-2:Ang-1 ratios in serum collected before lymphodepletion chemotherapy from patients who subsequently developed grade 0-3 (n=49) or ≥4 (n=6) neurotoxicity. The median (bar) and interquartile range are shown. (D) vWF string unit formation in HUVECs incubated with serum collected from day 3-5 from patients who received CD19 CAR-T cells and developed grade ≥4 neurotoxicity (n=4) or from healthy donors (n=4). (E) vWF string unit formation in HUVECs incubated with serum collected from patients with grade ≥4 (n=3) or grade 0-3 (n=6) neurotoxicity between day 7 and 14 after CAR-T cell infusion. The mean value of 2 samples collected on days 7 and 10 was used for one patient without neurotoxicity. (F) HMW and LMW vWF multimers in serum from patients with grade ≥4 (n=5) compared to grade 0-3 (n=6) neurotoxicity. The mean+/−SEM are shown in (B)-(E).

Endothelial Activation in Patients with Acute Neurotoxicity Before and after Infusion with CD19-Specific CAR-Modified T Cells The presence of vascular dysfunction and DIC indicated that endothelial activation might be present in patients with severe neurotoxicity. The angiopoietin (Ang)-Tie2 axis regulates the balance between endothelial quiescence and activation (Page and Liles, *Virulence* 4:507-16, 2013). Ang-1 is produced constitutively, primarily by vascular pericytes, and favors endothelial cell quiescence and stabilization when bound to the endothelial Tie2 receptor. Ang-2 is stored in endothelial Weibel-Palade bodies and released upon endothelial cell activation by stimuli including inflammatory cytokines. Ang-2 displaces Ang-1 from Tie2, resulting in activation of pro-thrombotic and pro-inflammatory pathways and increased microvascular permeability. The concentrations of Ang-2 and Ang-1 in serum from patients after CAR-T cell infusion were evaluated, and it was found that the serum Ang-2 concentration (p=0.0003) and the Ang-2:Ang-1 ratio (p=0.0014) were higher in patients with grade ≥4 neurotoxicity compared to those with grade ≤3 neurotoxicity (FIG. 4A). To confirm the presence of in vivo endothelial activation in patients with severe neurotoxicity, the serum concentration of von Willebrand Factor (vWF) antigen (vWF Ag) was evaluated, a glycoprotein in hemostasis that, like Ang-2, is also stored in Weibel-Palade bodies in endothelial cells and released in response to endothelial cell activation (Schwameis et al., *Thromb. Haemost.* 113: 708-18, 2015). Compared to patients without neurotoxicity or with grade 0-3 neurotoxicity after infusion of CAR-modified T cells, those with grade ≥4 neurotoxicity had higher concentrations of vWF Ag in serum (P=0.004), which in some patients was 4-5 fold higher than those observed in pooled serum from healthy donors (FIG. 4B). IL8 was sequestered with vWF in Weibel-Palade bodies and was also elevated during severe neurotoxicity (FIG. 3E). These findings, including marked elevations in both Ang-2 and vWF Ag, indicate profound endothelial activation and Weibel-Palade body release during severe neurotoxicity.

Ang-2 and Ang-1 concentrations in serum from patients prior to commencing lymphodepletion chemotherapy were evaluated to examine whether patients with evidence of endothelial activation before embarking on CAR-T cell immunotherapy might be at higher risk of subsequent cytokine-mediated vascular injury and neurotoxicity. The Ang-2:Ang-1 ratio was higher in patients who subsequently developed grade ≥4 neurotoxicity compared with those with grade ≤3 neurotoxicity (FIG. 4C), indicating that before lymphodepletion, biomarkers of endothelial activation might identify patients at high risk of subsequent neurotoxicity. Furthermore, in paired samples between day 0 and day 1 after CAR-T cell infusion, the magnitude of the change in Ang-2 concentration correlated with increasing severity of subsequent neurotoxicity (grade 0-2, median 80 ng/mL; grade 3, median 394 ng/mL; grade ≥4, median 6,392 ng/mL; P=0.0039), indicating that endothelial activation occurs early after CAR-T cell infusion and precedes the onset of neurotoxicity (FIG. 1D).

To determine whether endothelial cell activation is induced by serum from patients who had received CAR-T cell infusions, serum was collected from normal donors and from patients with neurotoxicity 3-5 days after CAR-T cell infusion and each were examined for their ability to induce endothelial cell activation. Serum from the patients with neurotoxicity was found to induce a higher formation of strings comprising platelets and vWF bound to human vascular endothelial cells (HUVECs) compared to serum from normal donors (FIG. 4D and data not shown). vWF-platelet string unit formation was examined in HUVECs incubated with serum collected at least 7 days after infusion of CAR-modified T cells. Lower vWF string unit formation was observed for serum from patients with grade ≥4 neurotoxicity compared to serum from patients with grade 0-3 neurotoxicity, despite the presence of higher concentrations of IL-6, IFN-γ, Ang-2, and vWF Ag in patients with grade ≥4 neurotoxicity (FIG. 4E). Patients with grade ≥4 neurotoxicity were observed to have a lower fraction of HMW vWF multimers in serum and a higher fraction of LMW vWF multimers compared to those with grade ≤3 neurotoxicity (FIG. 4F), which may be due to consumption of the HMW vWF multimers that occurs during acute presentations of thrombotic thrombocytopenic purpura (TTP).

In this regard, the level and activity of ADAMTS13 was also examined since ADAMTS13 is a protease that cleaves HMW vWF from activated endothelium (Schwameis et al., 2015). When the ADAMTS13 activity was normalized to the vWF Ag serum level (ADAMTS13:vWF Ag ratio), it was discovered that the ADAMTS13:vWF Ag ratio was lower during grade ≥4 neurotoxicity than observed in those with grade ≤3 neurotoxicity (grade ≥4 versus ≤3; 26% vs 36%; p=0.0023), indicating that patients with grade ≥4 neurotoxicity inefficiently remove bound HMW vWF multimers from activated endothelium.

Together, these data indicate that serum from patients with CRS induces activation of endothelial cells, which release and bind vWF, and in severe cases cause sequestration of HMW vWF multimers and contributes to consumptive coagulopathy.

Example 7

Blood-Brain Barrier During Acute Neurotoxicity

Figures 5A, 5B, 5C, 5D, 5E, 5F:
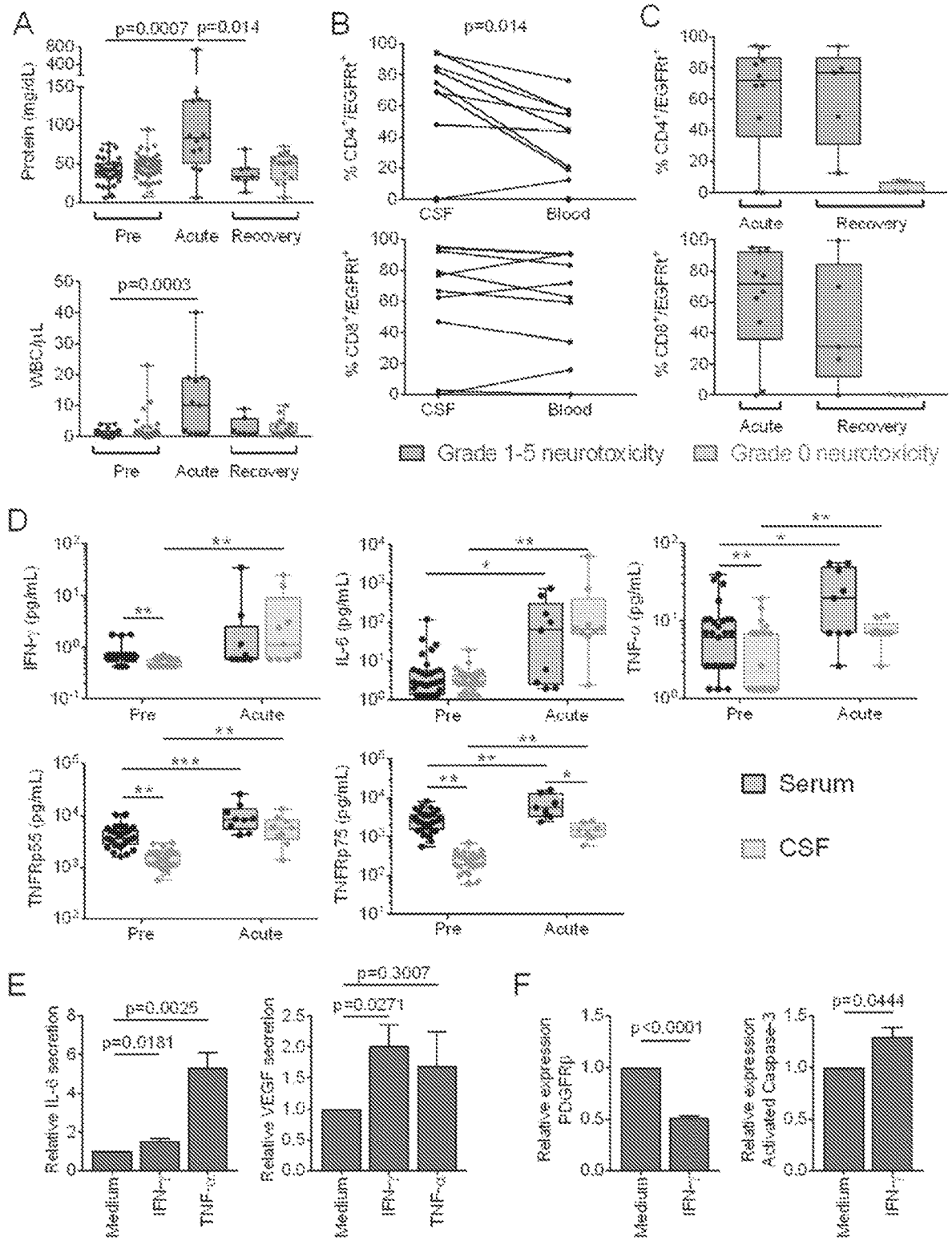
FIGS. 5A-5F. Increased permeability of the BBB during neurotoxicity. CSF was collected from patients before CAR-T cell infusion (Pre), during acute neurotoxicity (Acute), and after recovery from acute neurotoxicity or ≥21 days after CAR-T cell infusion in those without neurotoxicity (Recovery). (A) Protein concentration and WBC counts in CSF in patients who did (red) or did not (grey) develop neurotoxicity. Each point represents data from a single patient. Box and whisker plots show the interquartile range. (B) Paired CSF and blood samples collected on the same day from individual patients with neurotoxicity, showing CD4$^+$ and CD8$^+$ CAR-T cells as a percentage of total CD4$^+$ and CD8$^+$ cells, respectively. Each line represents data from a single patient. (C) CD4$^+$ and CD8$^+$ CAR-T cells as percentages of total CD4$^+$ and CD8$^+$ cells, respectively, in CSF. Each point represents data from a single patient. Box and whisker plots show the interquartile range. (D) Concentrations of cytokines in paired serum and CSF samples obtained from patients who developed neurotoxicity. Box and whisker plots show the median (bar) and interquartile range (box). Each point represents data from one patient. $*p<0.05$, $p<0.01$, $*p<0.001$. Paired tests were used to compare serum and CSF cytokines at a single timepoint. Unpaired tests were used for comparisons between Pre and Acute timepoints. (E) IL-6 and VEGF concentrations in supernatant from pericytes cultured with medium alone (Control), IFN-γ or TNF-α. Data are representative of 6 experiments and are expressed as the fold change (mean+/−SEM) compared to culture in medium alone. (F) PDGFRβ and activated caspase-3 expression by human brain vascular pericytes incubated with IFN-γ. Data are expressed as the fold change (mean+/−SEM) compared to culture in medium alone (Control).

The presence of endothelial activation and systemic capillary leak raised the possibility that severe neurotoxicity was associated with increased permeability of the blood-brain barrier (BBB). No evidence was found on cerebrospinal fluid (CSF) analyses to indicate that neurotoxicity after CD19-specific CAR-modified T cell therapy was associated with central nervous system (CNS) infection, and only one patient had concurrently detected CSF leukemia and neurologic signs. In CSF collected during acute neurotoxicity, a high protein concentration and leukocyte count was observed in comparison to CSF collected before lymphodepletion, consistent with increased permeability of the BBB (FIG. 5A). Both CD4$^+$ and CD8$^+$ CAR-T cells were detected in the CSF by flow cytometry (CD4$^+$/EGFRt$^+$, median 2.6 cells/μL; CD8$^+$/EGFRt$^+$, median 2.1 cells/μL). CAR-modified T cells comprised a higher fraction of the CD4$^+$ T cell subset in CSF compared to their counterparts in blood, indicating that the BBB might be more permeable to CD4$^+$ CAR-T cells (FIG. 5B). CD4$^+$ and CD8$^+$ CAR-T cells persisted in CSF at high frequency in a subset of patients after recovery from and/or stabilization of neurotoxicity, but were infrequent in CSF from patients who had not previously developed neurotoxicity (FIG. 5C).

These CSF results are consistent with increased permeability of the BBB during neurotoxicity, allowing increased transit of protein and CAR-T cells.

Serum cytokines can access the CSF through saturable transporters, circumventricular organs, and during BBB breakdown (Yarlagadda et al., Psychiatry 6:18-22, 2009). To determine whether increased BBB permeability during severe CRS would permit transit of serum cytokines into the CSF, cytokine concentrations were evaluated in paired blood and CSF samples before lymphodepletion and during acute neurotoxicity. Prior to lymphodepletion, there was a detectable cytokine concentration gradient between blood and CSF, with IFN-γ, TNF-α, and TNF-α stabilizing soluble receptors, TNFR p55 and TNFR p75, being higher in blood (FIG. 5D). During acute neurotoxicity, the concentrations of IFN-γ, TNF-α, IL-6, and TNFR p55 had increased and were comparable between serum and CSF, which indicated that either the BBB did not protect the CSF from high serum cytokine concentrations or there was local cytokine production in the CSF (FIG. 5D).

High concentrations of cytokines in the CSF might activate brain vascular pericytes, which together with endothelial cells play an important role in maintenance of the BBB (Armulik et al., Nature 468:557-61, 2010; Rustenhoven et al., Trends Pharmacol. Sci. 38:291-304, 2017). Compared to incubation in medium alone, incubation of primary human brain vascular pericytes with IFN-γ at concentrations observed in patients with severe neurotoxicity resulted in secretion of more IL-6 and vascular endothelial growth factor (VEGF; FIG. 5E), each of which activates endothelial cells and further increases BBB permeability (Page and Liles, 2013). Incubation of pericytes with TNF-α increased production of IL-6, but there was not a significant increase in VEGF (FIG. 5E). IFN-γ also induced downregulation of PDGFRβ and upregulation of cleaved caspase-3 expression, consistent with induction of pericyte stress (FIG. 5F) (Rustenhoven et al., 2017).

Together, these findings show that increased permeability of the BBB allows high concentrations of serum cytokines to transit into the CSF, including IFN-γ and TNF-α, which induces pericyte stress and secretion of cytokines that could further amplify increased BBB permeability.

Example 8

Endothelial Activation and Vascular Disruption in Fatal Neurotoxicity

Autopsy tissue from two patients who developed fatal CRS and neurotoxicity after CD19-specific CAR-modified T cell therapy was examined to determine if endothelial activation and vascular injury occurred in the brain during severe neurotoxicity.

Figures 6A, 6B, 6C, 6D, 6E, 6F:
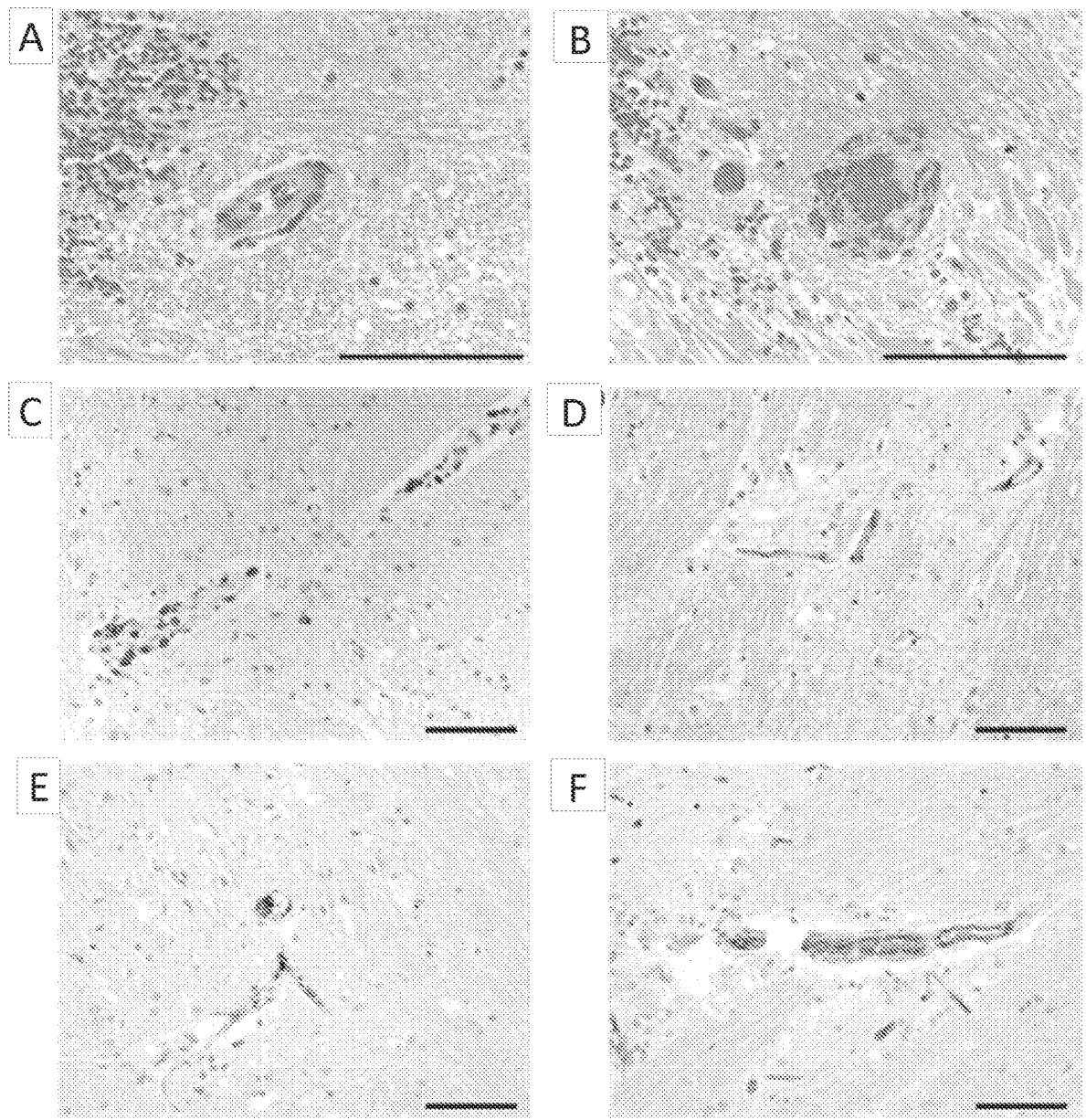
FIGS. 6A-6F. Endothelial activation and vascular disruption in CAR-T cell neurotoxicity. (A) Hematoxylin and eosin staining of medulla showing red blood cell extravasation into the surrounding parenchyma and Virchow-Robin space in the setting of minimal arteriolar wall disruption. (B) Hematoxylin and eosin staining showing fibrinoid vessel wall necrosis and vascular occlusion. (C) Perivascular CD8$^+$ T cell infiltration. (D) Immunohistochemistry (IHC) for vWF showing vWF binding to capillaries. (E) IHC for CD61 demonstrates intravascular microthrombi. (F) IHC for CD31 shows reduplicated and disrupted endothelium. Size bars (100 μm) are shown.

One patient died 13 days after CAR-T cell infusion with CRS and neurotoxicity characterized by brainstem hemorrhage and edema. Examination for neuropathology revealed multifocal microhemorrhages and patchy parenchymal necrosis in the pons, medulla and cervical spinal cord. Red blood cell (RBC) extravasation from multiple affected and non-affected vessels was observed in areas of otherwise normal brain (FIG. 6A). Small areas of infarction were associated with more severe vascular lesions with fibrinoid vessel wall necrosis, RBC extravasation, and perivascular CD8$^+$ T cell infiltration (FIGS. 6B and 6C). Flow cytometry showed that 93% of T cells in the pons were CAR-modified T cells (CD4$^-$/CD8$^+$ CAR-T cells, 51.9%: CD4$^+$/CD8$^-$ CAR-T cells, 48.1%). Of the CD45$^+$ cells in CSF collected at autopsy, 82% were CD3$^+$ T cells and of these 94.9% were CAR-T cells (CD4$^-$/CD8$^+$ CAR-T cells, 48%: CD4$^+$/CD8$^-$ CAR-T cells, 42.5%). We also observed intravascular vWF binding and CD61$^+$ platelet microthrombi (FIG. 6D, E), consistent with endothelial activation and intravascular coagulation. CD31 immunohistochemistry (IHC) demonstrated disrupted endothelium in some vessels (FIG. 6F). Reactive microglia were noted in a perivascular distribution, but marked and diffuse microglial activation was not observed and no CD79a$^+$ tumor cells were detected (data not shown). The brain of a patient who died due to severe CRS with multi-organ failure and grade 4 neurotoxicity (on day 3 after CAR-T cell infusion) showed disrupted endothelium by CD31 immunohistochemistry and endothelial cell activation as confirmed by intravascular vWF binding and CD61$^+$ platelet microthrombi. Further evidence of breach of the BBB included red blood cell extravasation from multiple vessels, vascular lesions with karyorrhexis, perivascular CD8$^+$ T cell infiltration, and fibrinoid vessel wall necrosis. CAR-T cells were detected in the CNS.

Example 9

Identification of Patients at High Risk of Subsequent Neurotoxicity

Figure 7A:
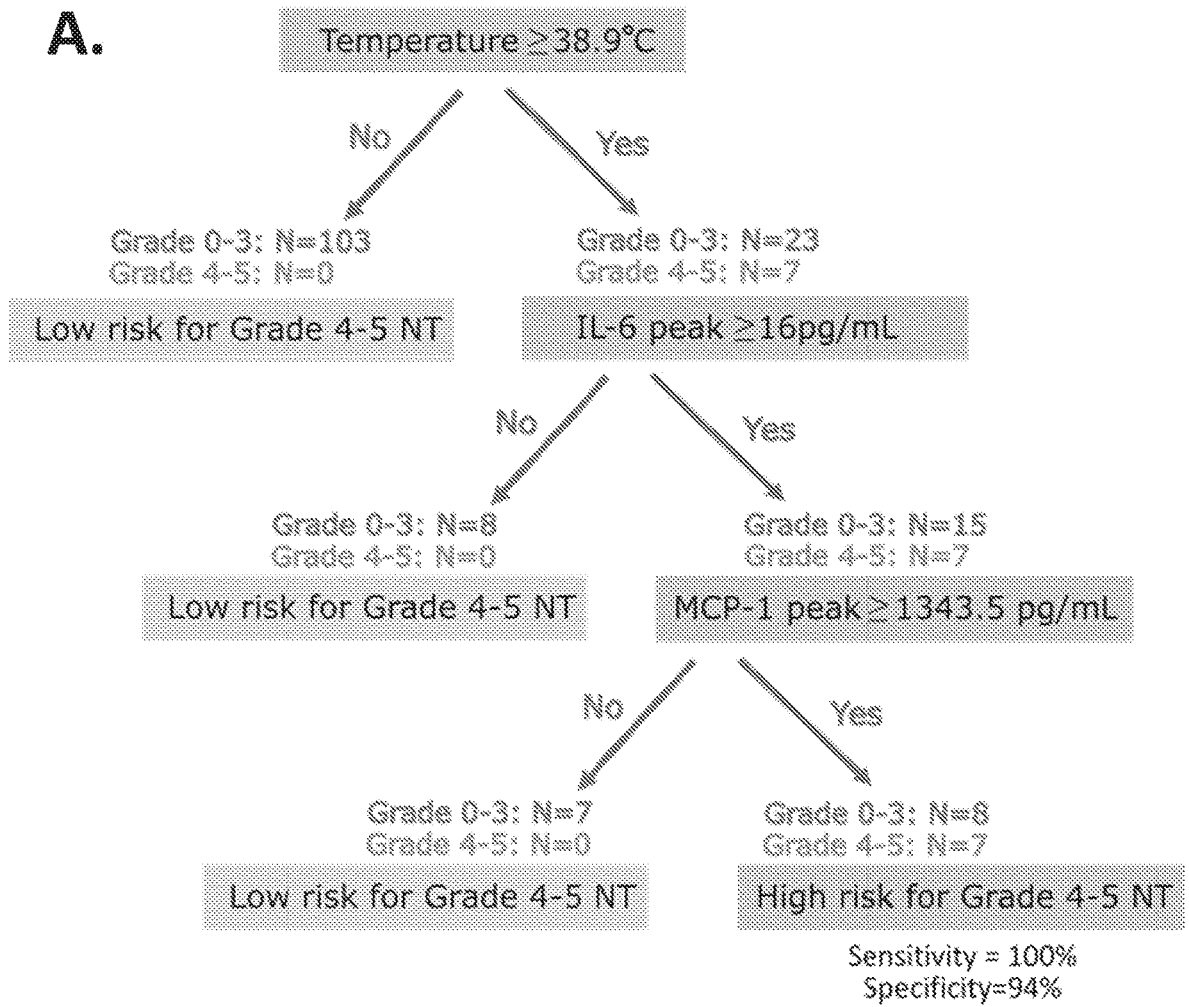
FIGS. 7A and 7B. Biomarkers to predict grade ≥4 neurotoxicity. (A) A classification tree model using temperature and serum IL-6 and/or MCP-1 concentrations within 36 hours of CAR-T cell infusion predicts with high sensitivity and high specificity subsequent grade ≥4 neurotoxicity. (B) Ang-2:Ang-1 ratios in serum collected before lymphodepletion chemotherapy from patients who subsequently developed grade 0-3 (n=49) or ≥4 (n=6) neurotoxicity. Endothelial activation biomarkers can predict patients at risk of neurotoxicity from CAR-T cell immunotherapy. Box and whisker plots show the median and interquartile range. Each point represents data from one patient.

Early identification of patients at risk of developing severe neurotoxicity might allow intervention with tocilizumab and/or corticosteroids, enabling reduction in serum cytokine concentrations that could mitigate or prevent subsequent toxicity. Fever of ≥38.9° C. occurring within 36 hours of CAR-T cell infusion had a 100% sensitivity for subsequent grade ≥4 neurotoxicity; however, the specificity was only 82%, in part due to the risk of fever associated with chemotherapy-induced neutropenia and infection. Because IL-6, IFN-γ, MCP-1, IL-15, IL-10, and IL-2 were higher (p<0.001) within the first 36 hours after CAR-T cell infusion in those who subsequently developed grade ≥4 neurotoxicity, evaluation of serum cytokines was investigated as a way to identify patients at risk of severe neurotoxicity with greater specificity as compared to evaluating temperature alone within 36 hours of CAR-T cell infusion. Classification tree modeling demonstrated that patients with fever ≥38.9° C. and serum IL-6 at ≥16 pg/mL and MCP-1 at ≥1343.5 pg/mL in the first 36 hours after CAR-T cell infusion were at high risk of subsequent grade ≥4 neurotoxicity (sensitivity 100%; specificity 94%; FIG. 7). Only 8 of 133 patients were misclassified in this model, and of those, only one (0.75%) did not subsequently develop moderate or severe grade 2-3 neurotoxicity and/or grade ≥2 CRS, indicating that unnecessary early intervention guided by the classification tree model is rare.

Figure 7B:
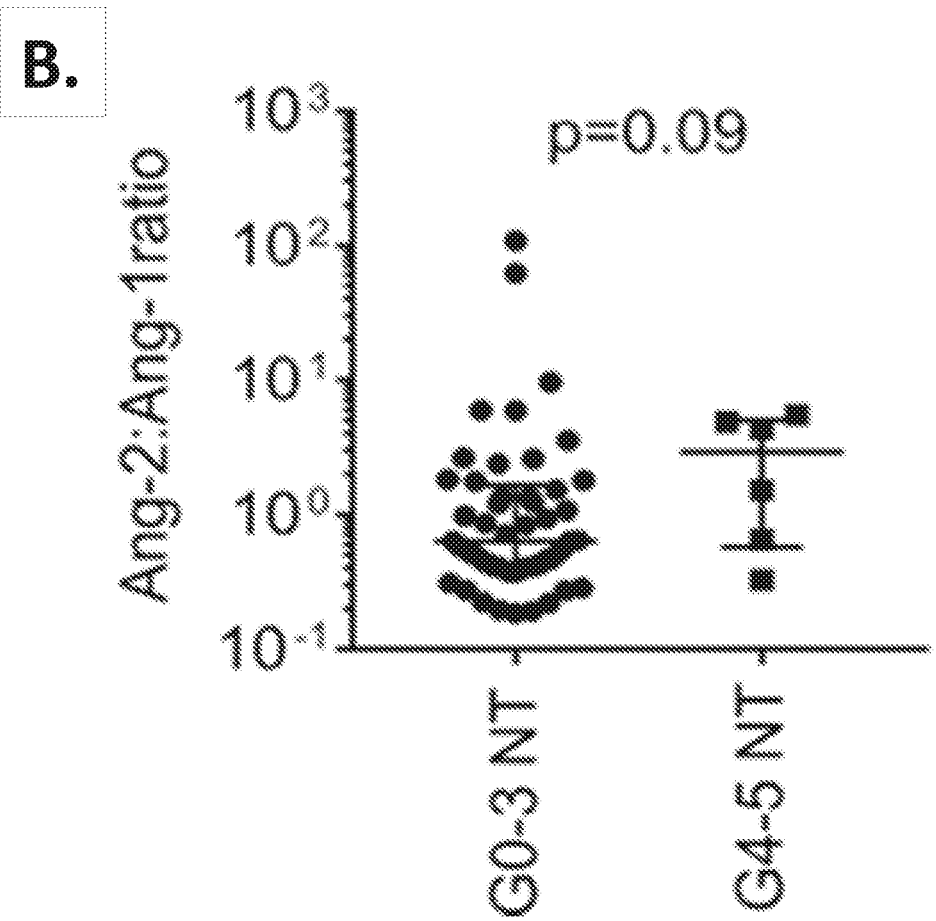

The best approach for prediction of severe toxicity would identify patients at high risk of toxicity before they commence therapy, when the infused CAR-modified T cell dose or treatment plan could be modified. Evidence of endothelial activation before embarking on CAR-T cell immunotherapy could identify patients at high risk of subsequent cytokine-mediated vascular injury and neurotoxicity. Serum Ang-1 and Ang-2 concentrations were evaluated in patients prior to commencing lymphodepletion chemotherapy and the Ang-2:Ang-1 ratio was higher in patients who subsequently developed grade ≥4 neurotoxicity compared to those with grade ≤3 neurotoxicity (FIG. 7B). Similarly, as shown in Example 6 above, an elevated level of vWF Ag, as with both Ang-2, and a reduced ADAMTS13:vWF Ag ratio also indicate profound endothelial activation and Weibel-Palade body release.

These data indicate that prior to commencing lymphodepletion and CAR-modified T cell immunotherapy, biomarkers of endothelial activation and Weibel-Palade body release can identify patients at high risk of CRS and/or neurotoxicity, providing an opportunity to modify therapy and minimize the risk of severe toxicity.

Example 10

Incidence and Kinetics of CRS and Neurotoxicity

One hundred and thirty-three (133) patients with relapsed or refractory B cell malignancies were included in the analyses (B-ALL, n=47; NHL, n=62; CLL, n=24). The median age was 54 years (range 20-73) and the median number of prior therapies was 4 (range 1-11; Table A). Twenty-five patients (19%) had previously undergone allogeneic hematopoietic stem cell transplantation (HCT), 22 (17%) had undergone autologous HCT, and 3 (2%) had undergone both autologous and allogeneic HCT. The lymphodepletion regimens given prior to CAR-T cell infusion are shown in Table 1. A majority of patients (78%) received a regimen containing both Cy and Flu. Thirty-five (26%) patients received CAR-T cells infused at DL1, 86 (65%) received DL2, and 12 (9%) received DL3.

Figure 8:
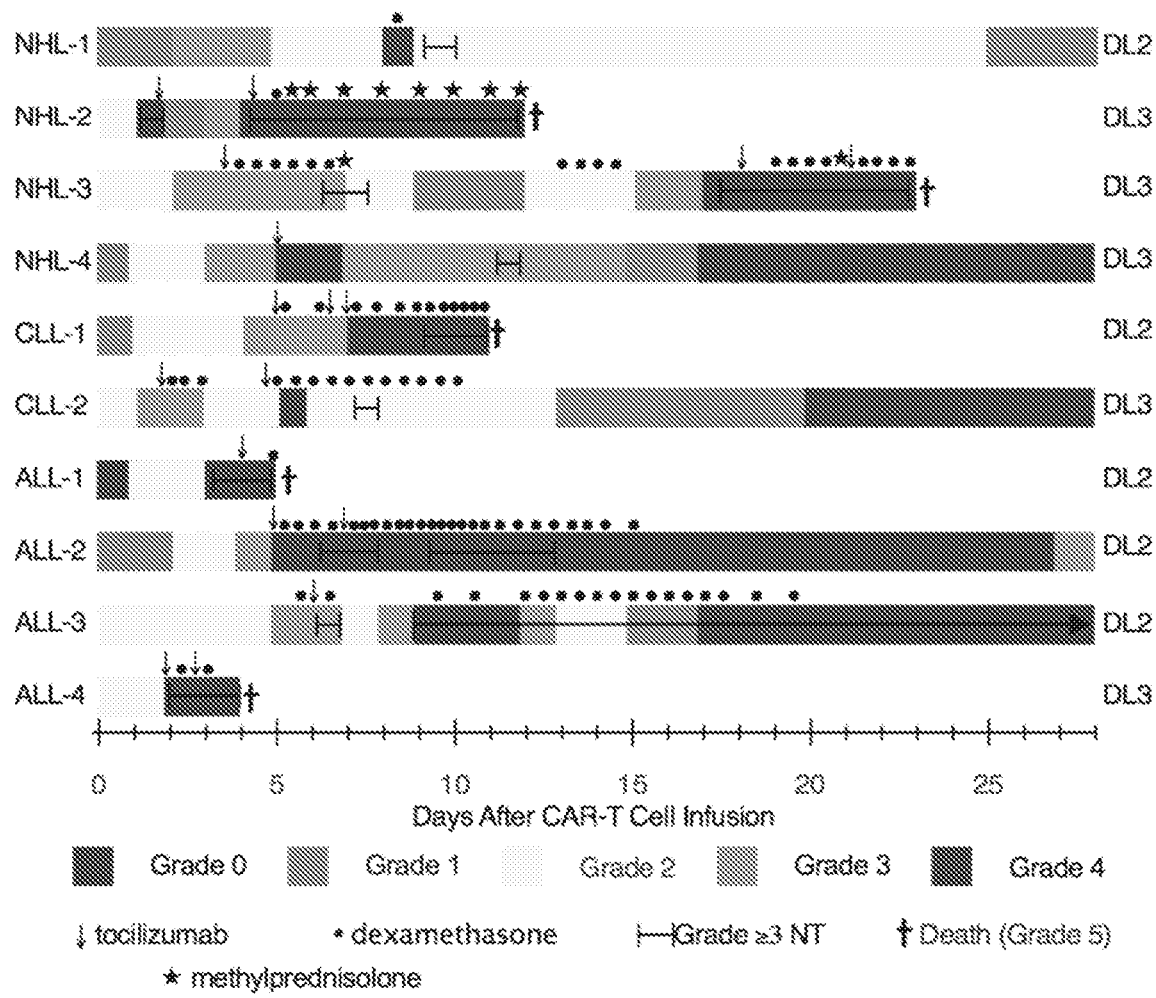
FIG. 8. Presentation, management, and outcomes of patients with grade ≥4 CRS. Colors on the swimmer plot indicate the CRS grade on each day through 28 days after CAR-T cell infusion in all patients who developed grade ≥4 CRS. The duration of grade ≥3 neurotoxicity and interventions with tocilizumab and/or corticosteroids are indicated in the figure. ALL-2 developed dialysis-dependent acute kidney injury (AKI) through day 26 followed by resolution of CRS-associated organ toxicity (grade 0) on day 37. ALL-3 died 4 months after CAR-T cell infusion with irreversible neurotoxicity, despite resolution of fever and hypotension associated with CRS on day 13 after CAR-T cell infusion. NHL-1 had ongoing grade 1 AKI at last available laboratory value on day 83. Doses of medications: dexamethasone 10 mg intravenous (IV) or oral, methylprednisolone 1 g IV, tocilizumab 4-8 mg/kg IV. NT, neurotoxicity.

CRS of any grade developed in 93 of 133 patients (70%; Table A). A majority of patients (123 of 133; 92.5%) had either no CRS (grade 0, 30%) or grade 1-3 CRS (grade 1, 26%; grade 2, 32%; grade 3, 4.5%). Ten patients (7.5%) developed grade ≥4 CRS (grade 4, 3.8%; grade 5, 3.8%) (FIG. 8). Five of these patients died within the first 30 days after CAR-T cell infusion as a result of complications associated with CRS and/or neurotoxicity. One additional patient died 4 months after CAR-T cell immunotherapy due to irreversible neurotoxicity. Of the 10 patients (7.5%) with grade ≥4 CRS, 8 were treated during the dose-escalation phase of the study. After establishing the CAR-T cell maximum tolerated dose (MTD), grade ≥4 CRS was only observed in 2 of 79 patients (2.5%).

TABLE A

Univariate and Multivariable Analysis of Baseline and Therapy-Related Characteristics by Severity of CRS.

| | CRS Grade | | | | Univariate Analysis | Multivariable Analysis |
| --- | --- | --- | --- | --- | --- | --- |
| | 0 | 1-3 | 4-5 | Total | P value[a] | P value[b] |
| Number of Patients, n | 40 | 83 | 10 | 133 | | |
| Age, years | | | | | .55 | — |
| Median [IQR] | 56 [44, 65] | 54 [43, 61] | 53.5 [43, 62] | 54 [43, 62] | | |
| Range | 27, 70 | 20, 73 | 20, 70 | 20, 73 | | |
| Sex, n (%) | | | | | .79 | — |
| Male | 28 (30) | 59 (63) | 6 (7) | 93 (70) | | |
| Female | 12 (30) | 24 (60) | 4 (10) | 40 (30) | | |
| Karnofsky Performance, n (%) | | | | | .30 | — |
| 60-70 | 2 (14) | 10 (71) | 2 (14) | 14 (10) | | |
| 80-90 | 32 (30) | 67 (63) | 7 (7) | 106 (80) | | |
| 100 | 6 (46) | 6 (46) | 1 (8) | 13 (10) | | |
| Disease Type, n (%) | | | | | .30 | — |
| ALL | 12 (25) | 31 (66) | 4 (9) | 47 (35) | | |
| CLL | 4 (17) | 18 (75) | 2 (8) | 24 (18) | | |
| NHL | 24 (39) | 34 (55) | 4 (6) | 62 (47) | | |

TABLE A-continued

Univariate and Multivariable Analysis of Baseline and Therapy-Related Characteristics by Severity of CRS.

| | CRS Grade | | | | Univariate Analysis | Multivariable Analysis |
|---|---|---|---|---|---|---|
| | 0 | 1-3 | 4-5 | Total | P value[a] | P value[b] |
| Prior Lines of Therapy, n | | | | | .13 | — |
| Median [IQR] | 3 [2, 5] | 4 [3, 5] | 5 [3, 7] | 4 [3, 5] | | |
| Range | 1, 11 | 1, 11 | 2, 9 | 1, 11 | | |
| Prior Transplant, n (%) | | | | | .38[c] | — |
| Allogeneic only | 3 (12) | 21 (84) | 1 (4) | 25 (19) | | |
| Autologous only | 9 (41) | 11 (50) | 2 (9) | 22 (17) | | |
| Both | 0 (0) | 3 (100) | 0 (0) | 3 (2) | | |
| Marrow Disease Burden by Flow Cytometry, % | | | | | <.0001 | <.0001 |
| Median [IQR] | 0 [0, 1.3] | 20 [0, 65] | 21 [3.6, 40] | 1.3 [0, 42] | | |
| Range | 0, 79 | 0, 97 | 0, 89.8 | 0, 97 | | |
| Not involved, n (%) | 23 (47) | 25 (51) | 1 (2) | 49 (37) | | |
| CD19+ Cells in Marrow by Flow Cytometry, % | | | | | .0001[d] | — |
| Median [IQR] | 3.6 [1.3, 6.6] | 22 [3.0, 66] | 22 [11, 40] | 8.8 [2.2, 48] | | |
| Range | 0, 79 | 0, 99 | 0.3, 90 | 0, 99 | | |
| Platelet Count, 1000/μl | | | | | .002 | .05 |
| Median [IQR] | 98 [58, 159] | 69 [38, 119] | 32 [19, 85] | 77 [40, 133] | | |
| Range | 11, 265 | 1, 553 | 5, 162 | 1, 553 | | |
| CD8+ Selection Method, n (%) | | | | | .001 | .03 |
| Bulk CD8+ | 9 (15) | 47 (77) | 5 (8) | 61 (46) | | |
| Central Memory Enriched | 31 (43) | 36 (50) | 5 (7) | 72 (54) | | |
| Lymphodepletion, n (%) | | | | | .67 | .02 |
| Cy/Flu based | 30 (29) | 65 (62) | 9 (9) | 104 (78) | | |
| Non-Cy/Flu based | 10 (35) | 18 (62) | 1 (3) | 29 (22) | | |
| CAR-T Cell Dose, n (%) | | | | | .002 | .003 |
| 2 × 10$^5$ EGFRt+ cells/kg | 10 (29) | 25 (71) | 0 (0) | 35 (26) | | |
| 2 × 10$^6$ EGFRt+ cells/kg | 27 (31) | 54 (63) | 5 (6) | 86 (65) | | |
| 2 × 10$^7$ EGFRt+ cells/kg | 3 (25) | 4 (33) | 5 (42) | 12 (9) | | |
| Lymphodepletion/CAR-T Cell Dose Interaction Effect[e] | | | | | .03 | .009 |

[a] Two-sided P-values calculated based on Kruskal-Wallis test for continuous variables, and Fisher's Exact test for categorical variables.
[b] Step-wise multivariable proportional odds models were performed to assess impact of baseline factors on the occurrence of CRS (Grade 0 vs 1-3 vs 4-5), where $log_{10}$ values were used to transform data as appropriate, with 0.001 substituting for values of 0.
[c] Any transplant type versus no transplant.
[d] Since marrow disease burden and total CD19+ cells in marrow have a strong correlation (r = 0.99, P < .0001), only marrow disease was included in the multivariable analysis.
[e] The interaction effect demonstrates that at increasing CAR-T cell dose levels the incorporation of Flu into the lymphodepleting regimen has a greater association with CRS.

Fever ≥38° C. was the first objective sign of CRS with the exception of one patient who presented with hypotension without fever. Fever onset occurred a median of 2.2 days [interquartile range, IQR, 0.9-5.6] after CAR-T cell infusion and lasted for a median [IQR] of 3.0 days [range of 1.2-4.8 days] (see Table 4).

TABLE 4

Characterization of Fever in Patients who Develop CRS

| | CRS Grade | | | |
|---|---|---|---|---|
| | 1-3 | 4-5 | Total | P value[a] |
| Number of Patients, n | 83 | 10 | 92 | |
| Fever Onset (days after CAR-T cell infusion) | | | | <.0001 |
| Median [IQR] | 3.9 [0.8, 5.6] | 0.4 [0.3, 0.9] | 2.2 [0.9, 5.6] | |
| Range | 0.1, 19 | 0.2, 1.0 | 0.1, 19 | |
| Time to Peak Temperature (days after CAR-T cell infusion) | | | | .001 |

TABLE 4-continued

Characterization of Fever in Patients who Develop CRS

| | CRS Grade | | | |
|---|---|---|---|---|
| | 1-3 | 4-5 | Total | P value[a] |
| Median [IQR] | 5.7 [4.3, 7.6] | 2.8 [1.3, 3.2] | 5.3 [3.4, 7.3] | |
| Range | 0.2, 30 | 0.4, 11 | 0.2, 30 | |
| Maximum Temperature (° C.) | | | | <.0001 |
| Median [IQR] | 39.4 [39.2, 30.6] | 40.4 [40.1, 40.6] | 39.5 [39.2, 39.8] | |
| Range | 37.7, 41.3 | 39.9, 40.9 | 37.7, 41.3 | |
| Fever Duration (days after first fever) | | | | .03 |
| Median, [IQR] | 2.5 [1.2, 4.7] | 4.4 [3.6, 5.4] | 3.0 [1.2, 4.8] | |
| Range | 0.02, 15 | 3.1, 6.8 | 0.02, 15 | |

[a]Two-sided P-values calculated based on Wilcoxon test.

Figures 9A, 9B, 9C, 9D:
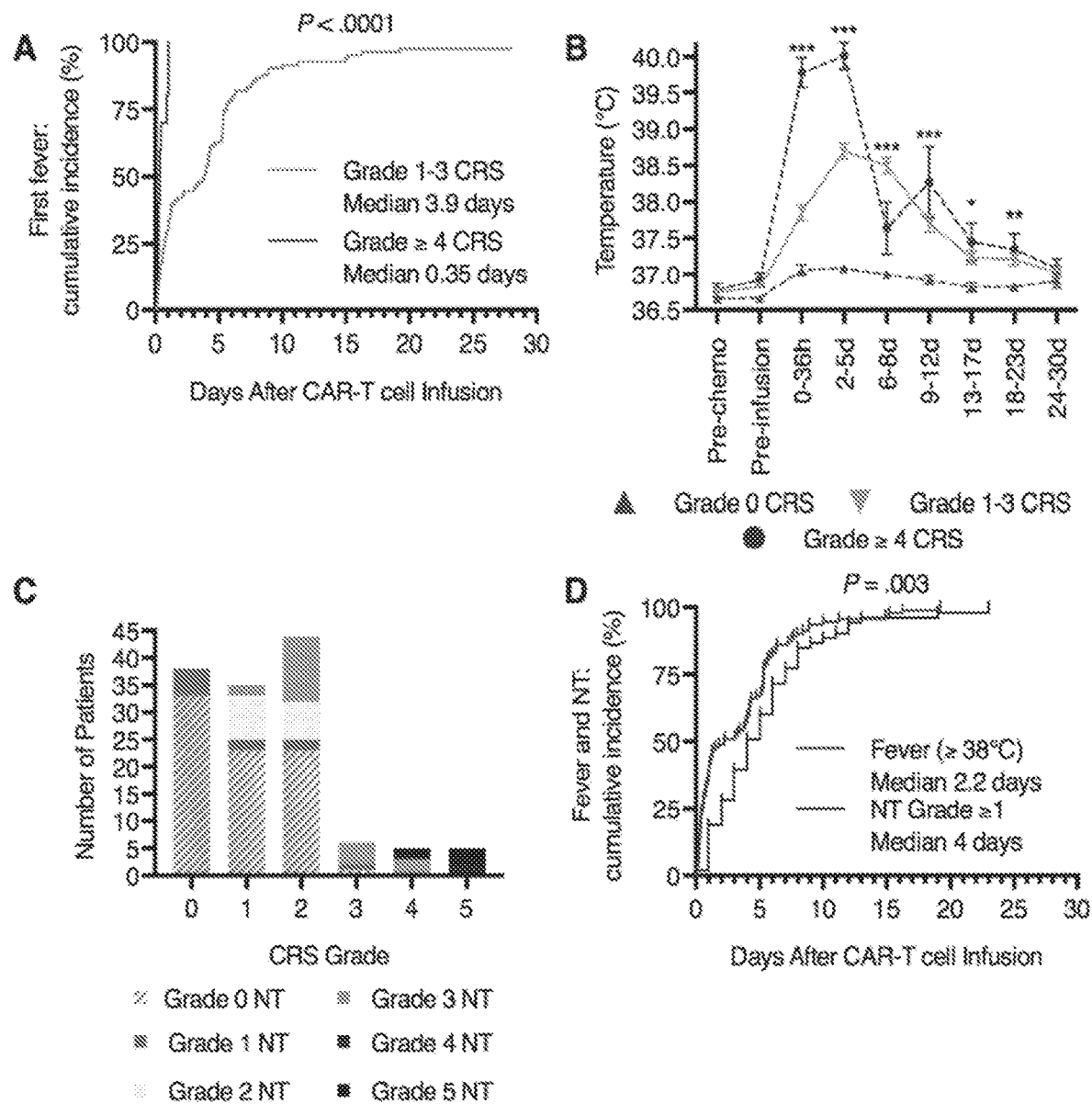
FIGS. 9A-9D. Kinetics of presentation of CRS and neurotoxicity. (A) Cumulative incidence curve for first fever ≥38° C. in patients with grade 1-3 (n=82) or grade ≥4 CRS (n=10). (B) Mean±SEM of the maximum temperature after CAR-T cell infusion. Kruskal-Wallis test, $*P<0.0001$, $0.0001<P<0.001$, $*0.001<P<0.005$. (C) Incidence and grading of neurotoxicity within each CRS grade. (D) The median time of onset of fever ≥38° C. (red, n=92) or neurotoxicity (blue, n=53) after CAR-T cell infusion. One patient with grade 2 CRS who developed hypotension without fever is not included. NT, neurotoxicity; Pre-chemo, prior to the start of lymphodepletion chemotherapy; Pre-infusion, before CAR-T cell infusion; h, hours; d, days after CAR-T cell infusion.
Figures 10A, 10B, 10C, 10D, 10E, 10F, 10G:
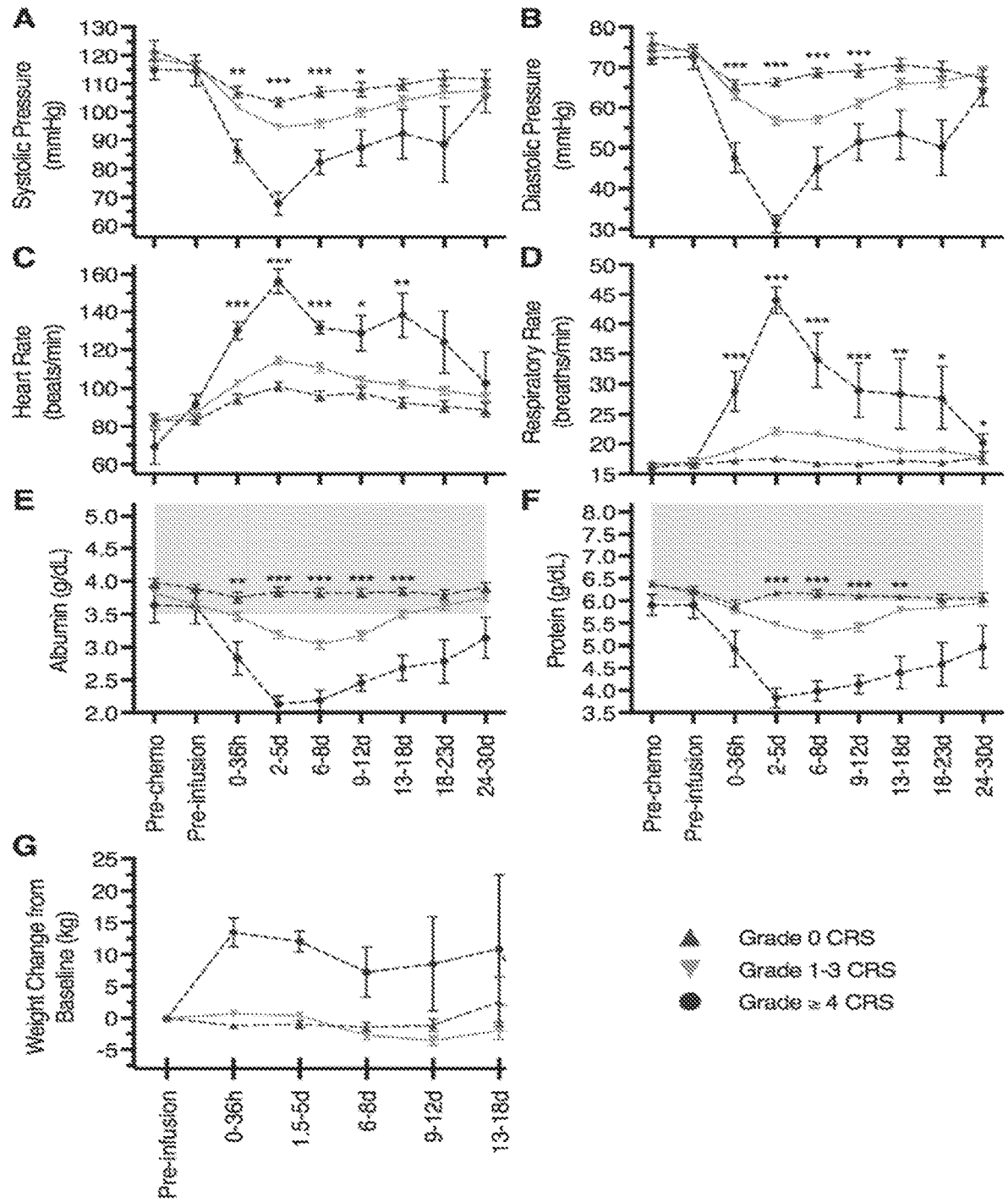
FIGS. 10A-10G. Hemodynamic instability and clinical capillary leak in grade ≥4 CRS. Mean±SEM of the minimum systolic and diastolic blood pressure (A-B), maximum heart and respiratory rates (C-D), minimum serum protein and albumin concentration (E-F), and weight gain from the start of lymphodepletion (G) are shown at the indicated times after CAR-T cell infusion. Kruskal-Wallis test, *P<0.0001, 0.0001<P<0.001, *0.001<P<0.005. Pre-chemo, prior to the start of lymphodepletion chemotherapy; Pre-infusion, before CAR-T cell infusion; h, hours; d, days after CAR-T cell infusion. Grey shading indicates normal range.

Compared to patients with grade 1-3 CRS, fever in patients with grade ≥4 CRS presented earlier after CAR-T cell infusion (P<0.0001), peaked earlier (P=0.001), reached a higher maximum temperature (P<0.0001), and was of longer duration (P=0.03, Table 4, FIGS. 9A and 9B). All patients who ultimately had grade ≥4 CRS were febrile within 25 hours after CAR-T cell infusion, and only 4 patients with grade ≤3 CRS developed their first fever more than 12 days after CAR-T cell infusion (FIG. 9A). Fifty-three of 133 patients (40%) had one or more grade ≥1 neurologic AEs (grade 1-2, 18%; grade ≥3, 21%), and the severity of neurotoxicity was associated with the severity of CRS (P<0.0001; Table 5); all patients with grade ≥4 CRS also developed grade ≥3 neurotoxicity (FIG. 9C). Neurotoxicity typically presented after CRS (P=0.003), with the first neurologic AE of any grade presenting a median [IQR] of 4 [2-7] days after CAR-T cell infusion (FIG. 9D). The first grade ≥3 neurologic AE presented 4.5 days [range of 3.2-6.2 days] after the first fever.

TABLE 5

Hospitalization and Neurotoxicity based on Severity of CRS

| | CRS Grade | | | | |
|---|---|---|---|---|---|
| | 0 | 1-3 | 4-5 | Total | P value[a] |
| Total, n | 40 | 83 | 10 | 133 | |
| Days in Hospital, n | | | | | <.0001 |
| Median [IQR] | 0 [0, 3] | 9 [6, 17] | 18 [7, 43] | 7 [3, 14] | |
| Range | 0, 227 | 0, 96 | 3, 98 | 0, 227 | |
| Neurotoxicity, n (%) | | | | | <.0001 |
| Grade 0 | 33 (41) | 48 (59) | 0 (0) | 81 (61) | |
| Grade 1-2 | 5 (21) | 19 (79) | 0 (0) | 24 (18) | |
| Grade 3-5 | 0 (0) | 18 (64) | 10 (36) | 28 (21) | |
| B cell Acute Lymphoblastic Leukemia, n | 12 | 31 | 4 | 47 | |
| Days in Hospital, n | | | | | .0002 |
| Median [IQR] | 0 [0, 2] | 11 [6, 18] | 24 [4, 71] | 7 [3, 17] | |
| Range | 0, 227 | 3, 96 | 3, 98 | 0, 227 | |
| Neurotoxicity, n (%) | | | | | .001 |
| Grade 0 | 10 (46) | 12 (54) | 0 (0) | 22 (47) | |
| Grade 1-2 | 2 (18) | 9 (82) | 0 (0) | 11 (23) | |
| Grade 3-5 | 0 (0) | 10 (71) | 4 (29) | 14 (30) | |
| Non-Hodgkin's Lymphoma, n | 24 | 34 | 4 | 62 | |
| Days in Hospital, n | | | | | <.0001 |
| Median [IQR] | 0 [0, 3] | 7 [5, 12] | 18 [16, 24] | 6 [1, 10] | |
| Range | 0, 20 | 2, 32 | 13, 30 | 0, 32 | |
| Neurotoxicity, n (%) | | | | | <.0001 |
| Grade 0 | 21 (50) | 21 (50) | 0 (0) | 42 (68) | |
| Grade 1-2 | 3 (25) | 9 (75) | 0 (0) | 12 (19) | |
| Grade 3-5 | 0 (0) | 4 (50) | 4 (50) | 8 (13) | |
| Chronic Lymphocytic Leukemia, n | 4 | 18 | 2 | 24 | |
| Days in Hospital, n | | | | | .007 |
| Median [IQR] | 0 [0, 2] | 12 [7, 19] | 28 [17, 49] | 9 [5, 19] | |
| Range | 0, 3 | 4, 42 | 7, 49 | 0, 49 | |
| Neurotoxicity, n (%) | | | | | .13 |
| Grade 0 | 4 (25) | 12 (75) | 0 (0) | 16 (67) | |
| Grade 1-2 | 0 (0) | 2 (100) | 0 (0) | 2 (8) | |
| Grade 3-5 | 0 (0) | 4 (67) | 2 (33) | 6 (25) | |

[a]Two-sided p-values calculated based on Kruskal-Wallis test.

One hundred and nine patients (82%) received lymphodepletion chemotherapy and CAR-T cell infusion in the outpatient setting. In those who developed grade ≥4 CRS, the severity of CRS did not reach grade ≥3 until a median of 3.4 days (range 1.4-4.7 days) after the onset of fever, which provided sufficient time for hospital admission and therapeutic intervention at the first fever prior to the development of more severe toxicity. The median [IQR] duration of hospitalization for all patients was 7 days [range of 3-14 days] and was associated with the severity of CRS (grade 0, median 0 days; grade 1-3, 9 days; grade ≥4, 18 days; P<0.0001, Table 5). Twenty-six patients (20%) with CRS and/or neurotoxicity received tocilizumab and/or dexamethasone to treat CRS and/or neurotoxicity. Twenty patients received dexamethasone and tocilizumab, 5 received dexamethasone alone, and one received tocilizumab alone. Fever resolved a median [IQR] of 0.4 [0.2-2.0] days following the first dose of tocilizumab or dexamethasone.

Example 11

Vascular Instability and Organ Dysfunction in Patients with Severe CRS

After CAR-T cell infusion, patients with severe CRS exhibited hemodynamic instability and capillary leak with hypotension, tachycardia, tachypnea, hypoalbuminemia, hypoproteinemia and weight gain (FIGS. 10A-10G). Seventeen of 133 patients (13%) were admitted to the intensive care unit (ICU) for management of CRS and/or neurologic AEs and the median [IQR] duration of care in the ICU was 3 days [range of 2-7 days]. Eleven of 133 patients (8%) received vasopressor support. Five patients were intubated and ventilated to manage respiratory failure associated with severe neurotoxicity, 3 were ventilated for management of pulmonary dysfunction, and 2 due to disease progression.

Figures 14A, 14B, 14C, 14D, 14E, 14F, 14G, 14H, 14I:
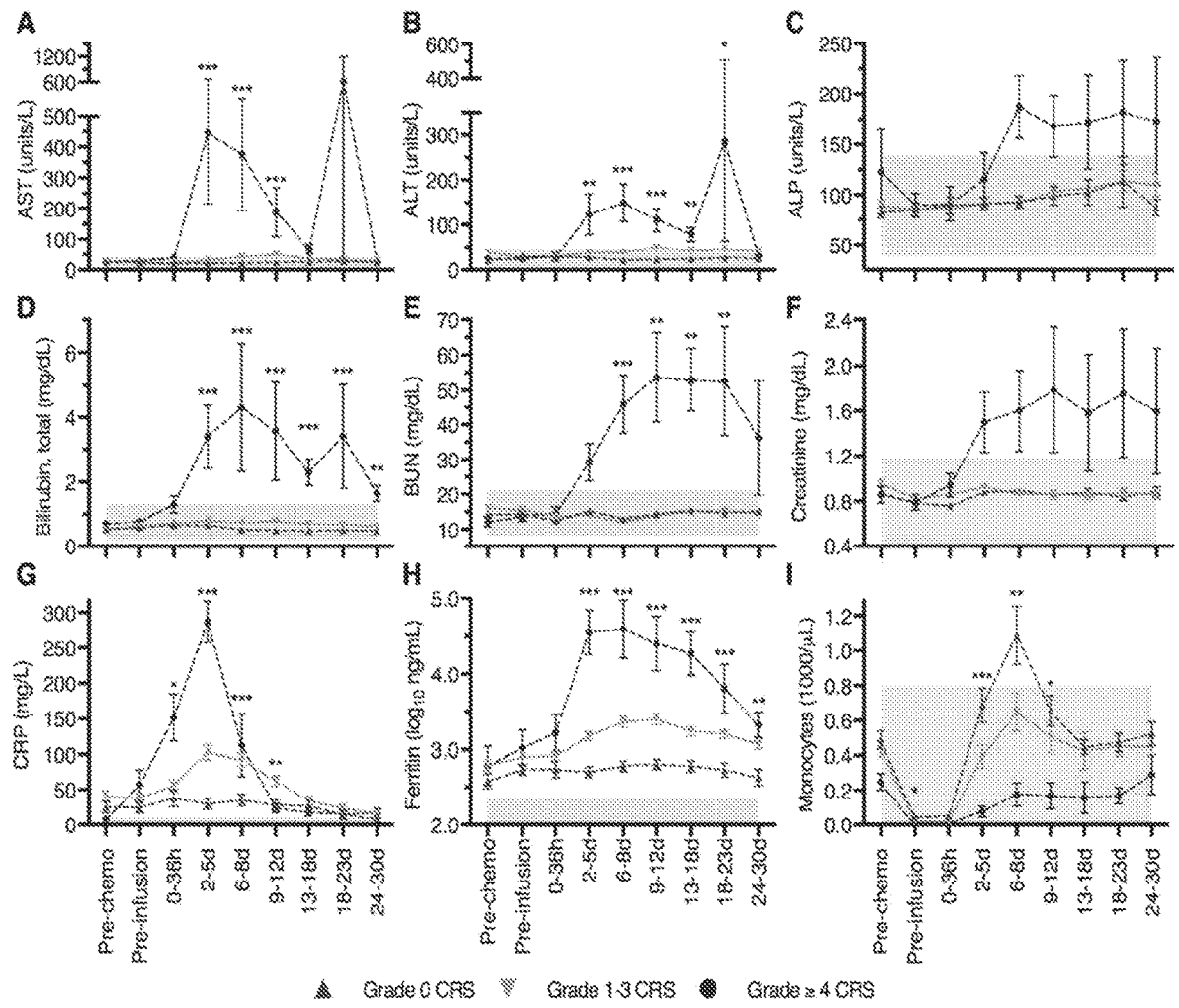
FIGS. 14A-14I. Hepatic and renal function, CRP, ferritin, and blood monocyte counts in CRS. (A-I) Maximum serum AST (A), ALT (B), ALP (C), bilirubin (D), BUN (E), creatinine (F), C-reactive protein (CRP; G), and ferritin (H) concentrations, and blood monocyte counts (I) at the indicated times. Mean±SEM values are shown; P values were determined using the Kruskal-Wallis test, *P<0.0001, 0.0001<P<0.001, *0.001<P<0.005. Pre-chemo, prior to the start of lymphodepletion chemotherapy; Pre-infusion, before CAR-T cell infusion; h, hours; d, days after CAR-T cell infusion. Grey shading represents the normal range.

All patients with grade ≥4 CRS developed grade ≥3 non-neurologic organ toxicity secondary to CRS, which resolved a median of 24 days (range 12-32 days) after resolution of fever. Only 3 patients with grade A CRS developed grade 3 non-neurologic organ toxicity (2 hepatic, 1 cardiac), and these events resolved in 1-2 days. Nine of the 10 patients with grade ≥4 CRS developed hepatic dysfunction, manifest by elevated AST, ALT, ALP, and bilirubin, with 5 patients having grade ≥3 transaminase elevation (FIGS. 14A-14D). The AST peaked between days 2-5, whereas the ALT, ALP and total bilirubin peaked later at day 6-8. One patient developed late hepatic dysfunction on day 20 associated with severe hypotension due to gastrointestinal hemorrhage. Three of the 10 patients with grade ≥4 CRS developed grade ≥3 acute kidney injury, with one patient requiring hemodialysis for 15 days until recovery of renal function (FIGS. 14E and 14F).

Example 12

Delayed Hematopoietic Recovery in Patients with Grade ≥4 CRS

Hematopoietic recovery in patients who had received lymphodepletion chemotherapy and CAR-T cell infusion was evaluated. To ensure observed differences in hematopoietic toxicity in patients with distinct grades of CRS were not due to differences in intensity of the lymphodepletion regimen, only patients who received Cy/Flu lymphodepletion (n=104) were included in the analysis. The absolute neutrophil count (ANC), hematocrit (HCT), hemoglobin concentration (Hb) and platelet count declined after lymphodepletion, reaching nadirs day 2-5 after CAR-T cell infusion (FIGS. 11A-D), which were lower in patients with more severe CRS. Patients with grade ≥4 CRS received more platelet (P=0.002) and red cell (P=0.04) transfusions than those with grade ≤3 CRS (FIG. 11E); 5 of 10 patients with grade ≥4 CRS were refractory to platelet transfusion. The time to hematologic recovery was longer than expected in most patients with grade 4 CRS (Table 6), and was delayed in patients with grade 1-3 CRS (median [IQR] 13.5 days [range of 6.5-18.1 days] compared to those without CRS (median [IQR], 4.1 days [range of 2.9-7.5 days], P=0.0002).

TABLE 6

Hematopoietic Recovery in Patients with Grade 4 CRS

| Patient | Blood and Marrow before Lymphodepletion | Recovery (days after CAR-T cell infusion) | | | Blood and Narrow at Re-staging |
|---|---|---|---|---|---|
| | | ANC[a] | Plts[b] | Erythroid[c] | |
| NHL-1 | Day −14: ANC 1,830/μL, Hb 10.9 g/dL, plts 53,000/μL Marrow: 30-40% cellularity with trilineage hematopoiesis and low level (5%) mantle cell lymphoma involvement | 8 | 18 | 17 | Day 28: ANC 1,420/μL, Hb 9.0 g/dL, plts 65,000/μL Marrow: 40% cellularity with trilineage hematopoiesis; no evidence of lymphoma or hemophagocytosis. |
| NHL-4 | Day −34: ANC 2,370/μL, Hb 9.7 g/dL, plts 72,000/μL Marrow: 75% cellularity with 0.2% abnormal B cells Karyotype: 46,XY,t(10; 13)(p11.2;q34)[2]/46,XY [18] | 20 | —[d] | —[d] | Day 28: ANC 840/μL, Hb 8.5 g/dL, plts 19,000/μL Marrow: 30-40% cellularity with megakaryocytic hypoplasia and relative myeloid hyperplasia; no evidence of lymphoma or hemophagocytosis. Karyotype: 46,Y,t(X;3) (2?4;p23),(inv2)(p13q31), t(4;15)(q12;q21)[8]/46,XY [12] |

TABLE 6-continued

Hematopoietic Recovery in Patients with Grade 4 CRS

| Patient | Blood and Marrow before Lymphodepletion | Recovery (days after CAR-T cell infusion) | | | Blood and Narrow at Re-staging |
|---|---|---|---|---|---|
| | | ANC[a] | Plts[b] | Erythroid[c] | |
| CLL-2 | Day −14: ANC 770/μL, Hb 9.3 g/dL, plts 33,000/μL Marrow: Trilineage hematopoiesis with diffuse involvement (90%) by CLL | 37 | —[e] | —[e] | Day 28: ANC 50/μL, Hb 8.6 g/dL, plts 5,000/μL Marrow: 5% cellularity, predominantly lymphocytes and stromal elements; no evidence of residual CLL. |
| ALL-2 | Day −8: ANC 2,310/μL, Hb 11.4 g/dL, 139,000/μL Marrow: 50% cellularity with trilineage hematopoiesis and 26% involvement with ALL infiltrate | 52 | 467 | 66 | Day 22: ANC 750/μL, Hb 8.9 g/dL, plts 9,000/μL Marrow: 20% cellularity with megakaryocytic aplasia and no evidence of B-ALL or hemophagocytosis. |
| ALL-3 | Day −12: ANC 90/μL Hb 8.1 g/dL, 31,000/μL Marrow: 50-60% cellularity with myeloid hypoplasia, erythroid atypia, and 20-25% ALL blasts Karyotype[f]: 46,XY,del(20)(q11.2q13.3) [4]/46,sl,der(22)t(17; 22)(q11.2;q13)[6]/46,sl, der(15)t(15;17)(q26.1;q11.2) [4]/46,sl,i(17)(q10) [3]/69<3n>,XYY,+1,−3del (3)(q24q27),−4, +add(5)(q11.2),+6,+11, add(11)(q23),−13,−14, add(15)(q15),−16,−17, +20,+21,+22 [cp4] | 29 | 56 | 104 | Day 23: ANC 720/μL, Hb 7.9 g/dL, plts 26,000/μL Marrow: 50% cellularity with relatively increased erythropoiesis, 10% erythroid dysplasia and 0.7% myeloid blasts[f] Karyotype: 46,XY,del(20)(q11.2q13.3) [4]/46,sl,der(22)t(17;22)(q11.2;q13) [5]/46,sl,der(15)t (15;17)(q25;q11.2)[3]/46,sl, i(17)(q10),inc[1]/46,sl,der (6)t(1;6)(q21;p25)[2]/46,sl, der(6)t(6;17)(p23;q11.2)[2]/ 46,sl,dup(17)(q21q23)[2] |

[a]Neutrophil recovery was defined as ANC > 500/μL for three consecutive days.
[b]Platelet recovery was defined as platelets > 50,000/μL and transfusion independence for 7 days.
[c]Erythroid recovery was defined as transfusion independence for 7 days.
[d]NHL-4 had ongoing thrombocytopenia and anemia after CAR-T cell infusion, and was subsequently diagnosed with therapy related myelodysplastic syndrome (MDS). Karyotype interpretation at day −34 states: "since both cells with t(10;13) were seen in the unstimulated culture, it is possible that this clone may represent a therapy-related myeloid disorder", suggesting pre-existing MDS.
[e]CLL-2 died on day 90 from pulmonary aspergillus and had ongoing cytopenias with pRBC and platelet transfusion dependency.
[f]Therapy-related MDS preceded CAR-T cell infusion. Karyotype interpretation at day −12 states: "the presence of two distinct abnormal populations suggests a biclonal disease or the concurrence of two malignancies. The population with 20q- and the evolving clones with 17q gain may suggest the possibility of a myeloid neoplasm." Karyotype interpretation at day 23 states: "these results suggest myeloid disease persistence and progression."
ANC—absolute neutrophil count;
Hb—hemoglobin;
plts—platelets CRS has been associated with macrophage activation syndrome (Lee et al., *Blood* 124:188, 2014; Teachey et al., *Cancer Dis.* 6:664, 2016).[16,17] Consistent with this, we observed higher ferritin and CRP levels, and more prolonged monocytopenia in blood of patients with grade ≥4 CRS compared to those with grade ≤3 CRS (FIGS. 14G-14I). However, examination of bone marrow biopsies from patients with grade ≥4 CRS showed no evidence that increased hemophagocytosis contributed to delayed hematopoietic recovery. Rather, in 5 of 7 patients with grade ≥4 CRS and available marrow pathologic examination, the bone marrow was hypocellular without evidence of residual tumor (see Table 6).

Consumptive Coagulopathy in Grade ≥4 CRS

Figures 11A, 11B, 11C, 11D, 11E, 11F, 11G, 11H, 11I, 11J, 11K:
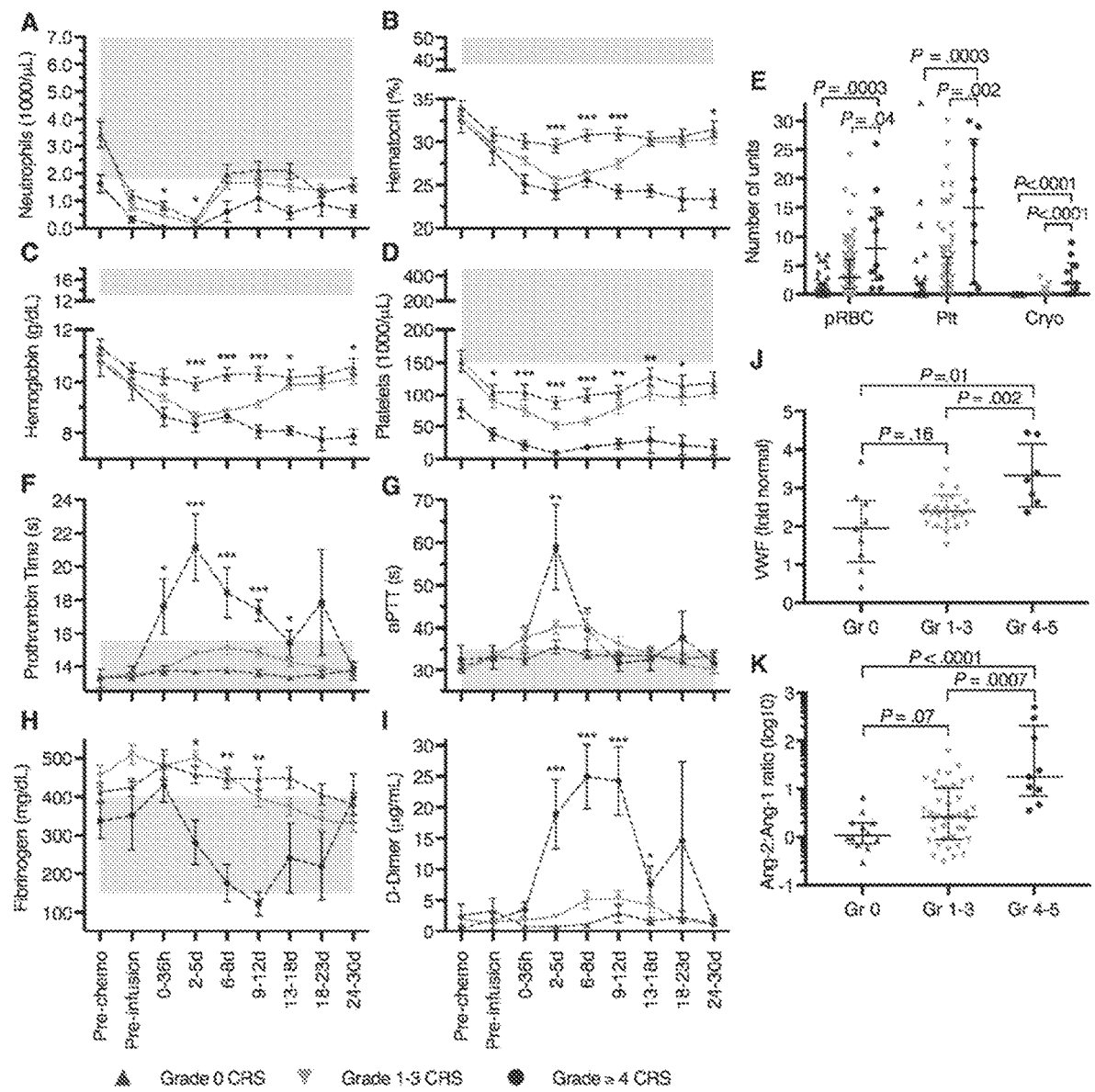
FIGS. 11A-11K. Hematopoietic toxicity, laboratory coagulopathy, and endothelial injury in grade ≥4 CRS. The minimum ANC (A), hematocrit (B), hemoglobin (C) and platelet count (D) are shown for patients receiving Cy/Flu lymphodepletion at the indicated times after CAR-T cell infusion (n=104). (E) Total transfused units of packed red blood cells (pRBC), platelets (Plt), and cryoprecipitate (Cryo) in the first 28 days after CAR-T cell infusion. The maximum PT (F) and aPTT (G), minimum fibrinogen (H), and maximum d-dimer (I) concentrations are shown at the indicated times after CAR-T cell infusion. (J) The fold change in VWF concentration in serum from a subset of patients at the peak of CAR-T cell expansion (n=60; grade 0, n=12; grade 1-3, n=39; grade ≥4 CRS, n=9) compared to the VWF concentration in pooled normal plasma (12.2 µg/mL; CRYOcheck, Precision Biologic, Dartmouth, NS, Canada). (K) The Ang-2:Ang-1 ratio at the peak of CAR-T cell expansion (n=60; grade 0, n=12; grade 1-3, n=39; grade ≥4 CRS, n=9). For (A-D) and (F-I): Data represent the mean+/−SEM. P values were determined using the Kruskal-Wallis test, *P<0.0001, 0.0001<P<0.001, *0.001< P<0.005. Pre-chemo, prior to the start of lymphodepletion chemotherapy; Pre-infusion, before CAR-T cell infusion; h, hours; d, days after CAR-T cell infusion. Grey shading indicates normal range. For (E, J, K): Each point represents data from one patient. The median and interquartile range [IQR] are shown. P values were determined using the Wilcoxon test, Gr, grade.
Figures 12A, 12B, 12C, 12D, 12E, 12F, 12G, 12H:
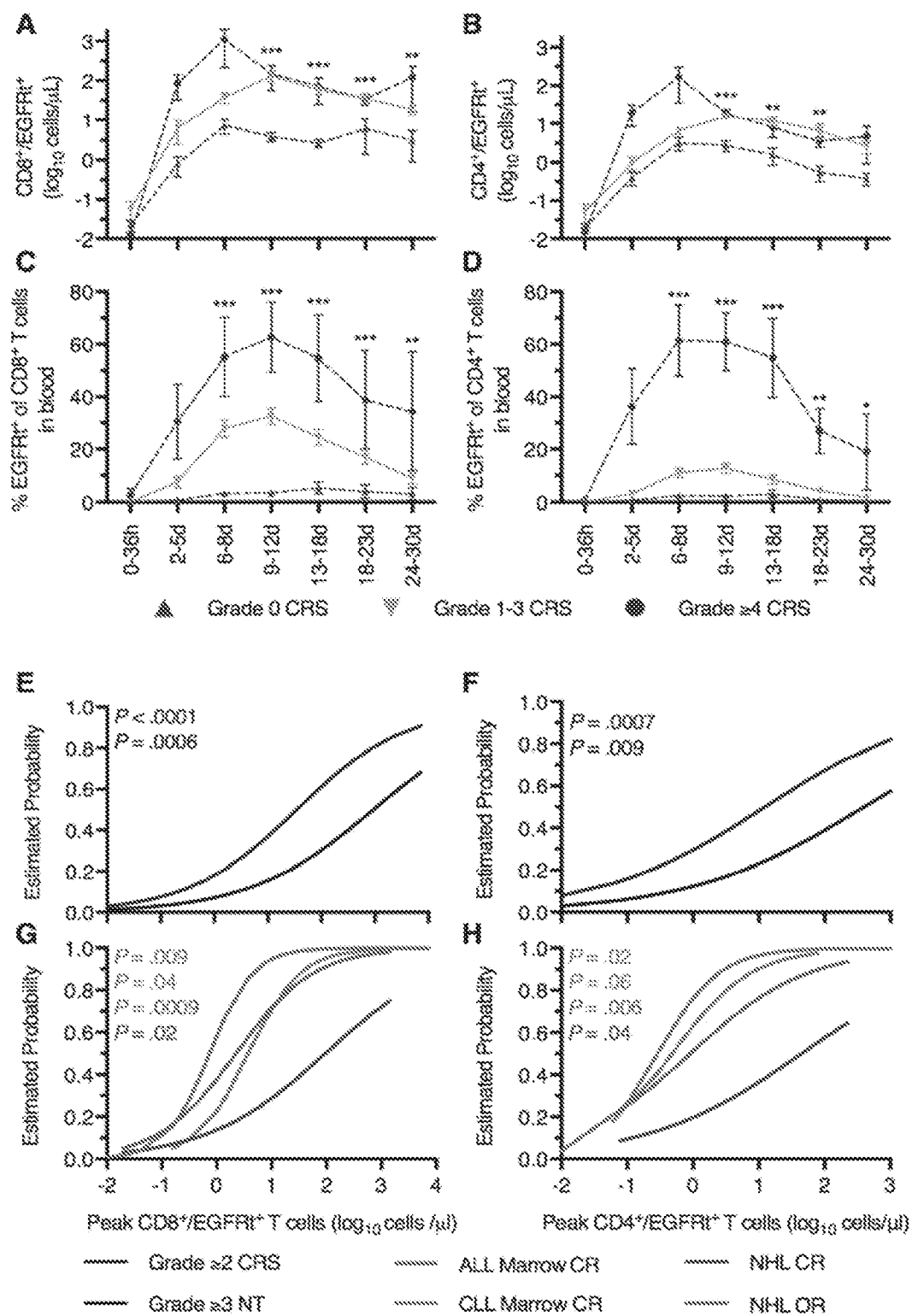
FIGS. 12A-12H. CAR-T cell counts in blood and estimated probabilities of response or toxicity. The absolute number (A-B) and percentage (C-D) of $CD8^+$ (left) and $CD4^+$ (right) CAR-T cells in blood. The mean±SEM of the maximum values are shown; P values were determined using the Kruskal-Wallis test, *P<0.0001, 0.0001<P< 0.001, *0.001<P<0.005. h, hours; d, days after CAR-T cell infusion. Estimated probabilities by logistic regression of grade ≥2 CRS and grade ≥3 neurotoxicity (NT) at peak $CD8^+$ (E) and $CD4^+$ (F) CAR-T cell counts in blood. Estimated probabilities by logistic regression of bone marrow complete response (CR) in ALL and CLL patients by flow cytometry, and CR or overall response (OR) in NHL patients according to Cheson imaging criteria (2014) at peak $CD8^+$ (G) and $CD4^+$ (H) CAR-T cell counts in blood. Lymph node CR in CLL patients is not depicted due to the limited cohort size available for analysis. P values are color-coded to indicate the association between the CAR-T cell peak counts and outcomes.

The prothrombin time (PT), activated partial thromboplastin time (aPTT), D-dimer, and fibrinogen was examined in patients at intervals after CAR-T cell infusion. Patients receiving therapeutic anticoagulation were excluded from the analyses (n=9). In the first week after CAR-T cell infusion, patients with grade ≤3 CRS had normal or mildly elevated prothrombin time (PT), activated partial thromboplastin time (aPTT), D-dimer, and fibrinogen. In contrast, those with grade ≥4 CRS developed early prolongation of the PT and aPTT, which peaked approximately 2-5 days after CAR-T cell infusion (FIGS. 11F and 11G). Increasing D-dimer and falling fibrinogen concentrations started at day 2-5, with hypofibrinogenemia occurring from days 9-12, consistent with disseminated intravascular coagulation (DIC; FIGS. 11H and 11I). Compared to their counterparts with grade 1-3 CRS, those with grade ≥4 CRS received more cryoprecipitate transfusions (P<0.0001, FIG. 11E) and had more severe and prolonged thrombocytopenia (FIG. 11D). Grade ≥3 hemorrhage occurred in only 3 patients (2%), all of whom had grade ≥4 CRS. Red cell fragmentation was not a prominent feature on blood film morphology analysis. The findings were consistent with a consumptive coagulopathy in patients with severe CRS.

Biomarkers of Endothelial Activation in Severe CRS

The presentation of vascular instability, capillary leak, and consumptive coagulopathy suggested that endothelial activation or dysfunction might be present in patients with severe CRS. This was confirmed by demonstrating that severe CRS was accompanied by high serum concentrations of VWF and Ang-2, which are released from Weibel-Palade bodies on endothelial activation. The mechanisms that lead to endothelial activation in CRS have not been characterized; however, the high serum concentrations of endothelium activating cytokines, such as IL-6 and IFN-γ observed in patients with severe CRS suggest that these cytokines may contribute. The serum VWF and the Ang-2:Ang-1 ratio were also found to be higher prior to commencing CAR-T cell immunotherapy in patients who subsequently developed more severe CRS, indicating that pre-existing endothelial activation might be a previously unrecognized risk factor for severe CRS. It is noteworthy that thrombocytopenia before lymphodepletion chemotherapy was associated with subsequent severe CRS.

Figures 15A, 15B, 15C:
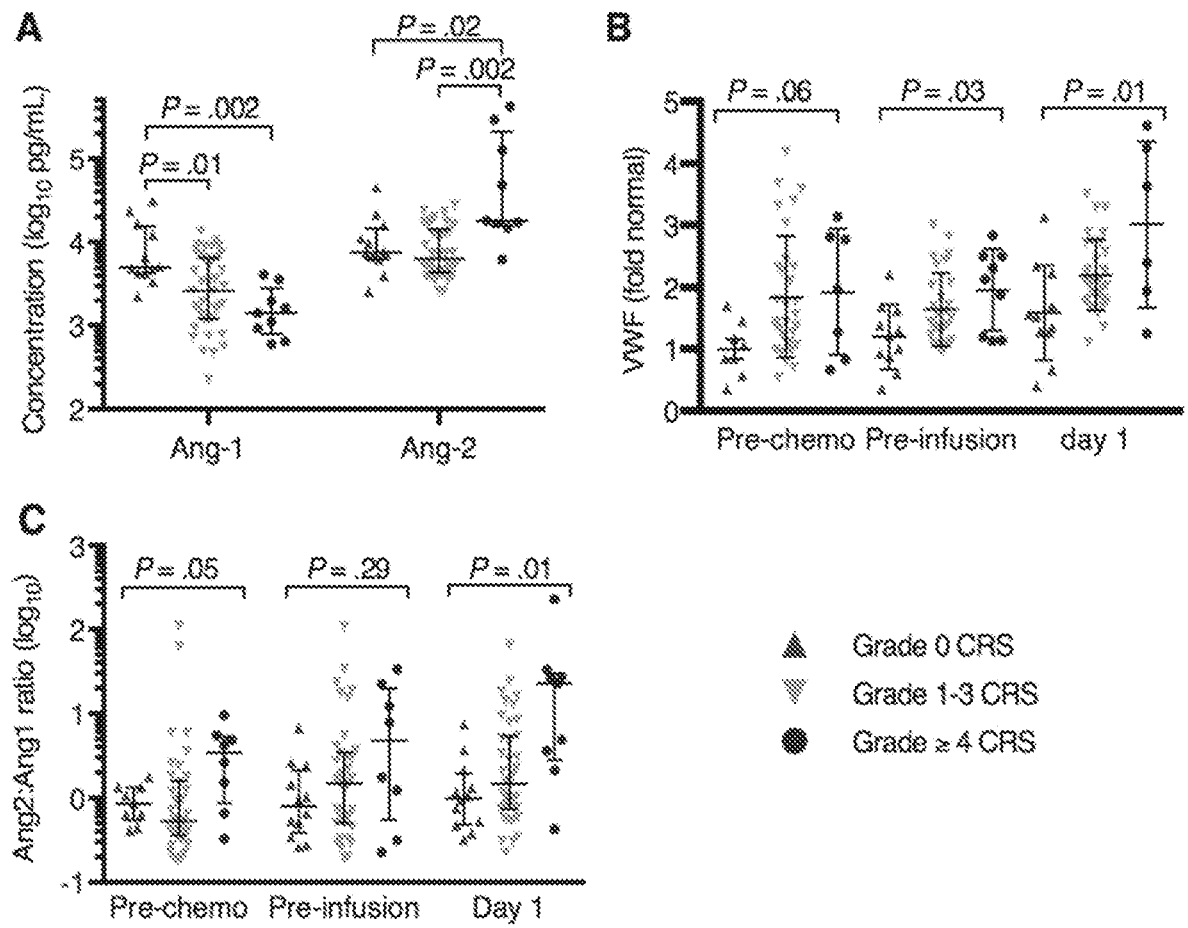
FIGS. 15A-15C. Biomarkers of endothelial activation in CRS. (A) Serum angiopoietin (Ang)-1 and Ang-2 concentrations at the peak of expansion of CAR-T cells (Mann-Whitney test). Von Willebrand Factor (VWF) concentration in patient serum expressed as the fold change over pooled normal serum (B) and the Ang-2:Ang-1 ratio (C) at the following times: prior to the start of lymphodepletion chemotherapy (Pre-chemo); before CAR-T cell infusion (Pre-infusion), and on day 1 after CAR-T cell infusion (Kruskal-Wallis test, Grade 0 vs 1-3 vs 4-5). For (A-C), n=60 (grade 0, n=12; grade 1-3, n=39; grade ≥4 CRS, n=9).
Figures 16A, 16B, 16C, 16D, 16E, 16F:
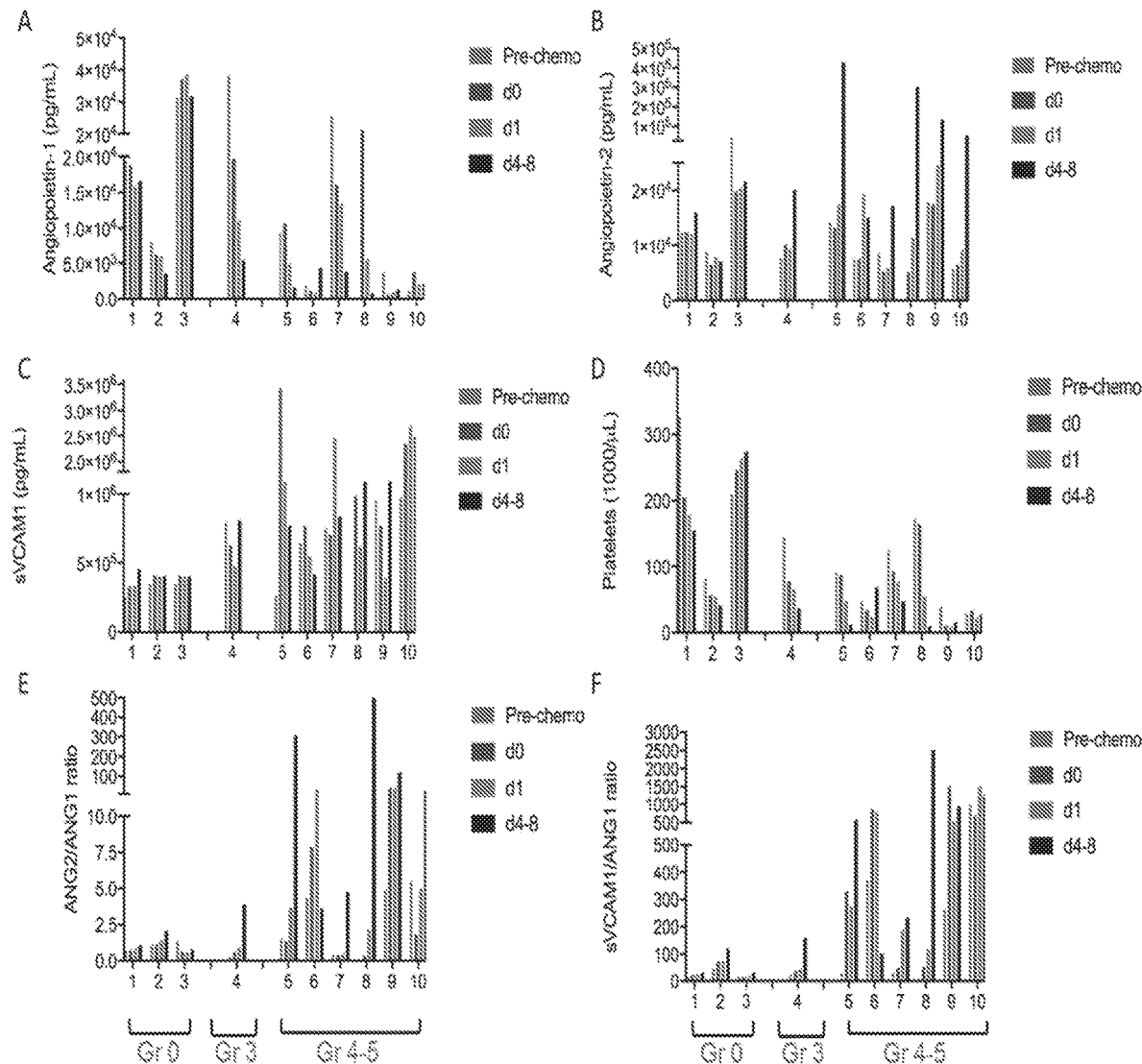
FIGS. 16A-16G. Angiopoietin-1, angiopoietin-2 and sVCAM-1 concentrations were assessed in serum from patients with ALL, NHL or CLL treated with lymphodepletion chemotherapy and CD19-targeted chimeric antigen receptor (CAR)-modified T cells. Samples were collected from 10 patients before lymphodepletion chemotherapy (Pre-chemo), on the day of CAR-T cell infusion prior to commencing the infusion (d=0), the day after CAR-T cell infusion (d=1), and during acute clinical toxicity 4-8 days after CAR-T cell infusion (d4-8). (A) Ang-1, (B) Ang-2, (C) sVCAM-1, and (D) platelet counts were measured for each patient and grouped by severity of neurotoxicity (patients 1-3, grade 0; patient 4, grade 3; patients 5-10, grade 4-5). Patients with grade 4-5 neurotoxicity had (E) high Ang-2: Ang-1 ratios, (F) high sVCAM-1:Ang-1 ratios during acute toxicity (black) and on the first day after CAR-T cell infusion (blue), providing an opportunity for early intervention with treatment with corticosteroids, anti-cytokine antibodies or agents that modify the angiopoietin-Tie-VCAM1 pathway. In addition, some patients who developed grade 4-5 neurotoxicity (6, 9, 10) had high Ang-2:Ang-1 or sVCAM-1:Ang-1 ratios before chemotherapy (green) or before CAR-T cell infusion (red), providing an opportunity to modify chemotherapy or CAR-T cell dosing and re-evaluating risk before starting therapy. (G) Ang-1 vs platelets: a correlation study of Ang-1 vs platelets (the source of Ang-1) in all samples from this experiment is provided.
Figure 16G:
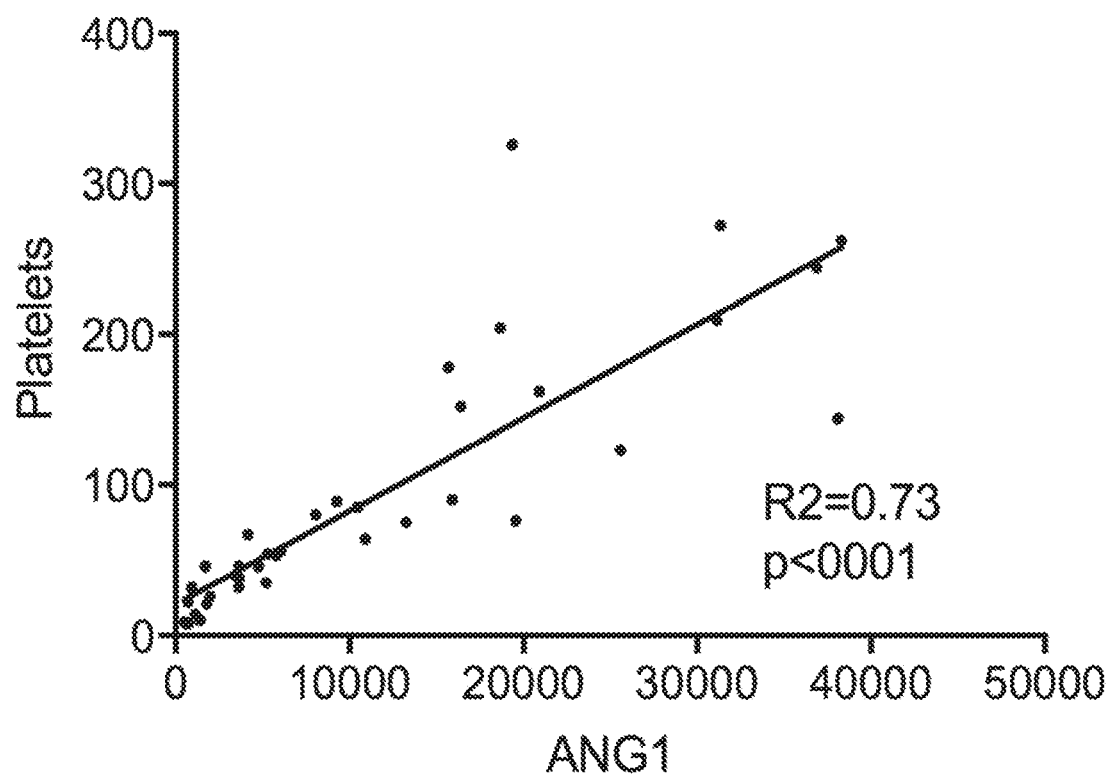

The presence of vascular instability, capillary leak and a consumptive coagulopathy raised the possibility that endothelial activation might contribute to the clinical findings in patients with severe CRS. Von Willebrand Factor (VWF) is released from Weibel-Palade bodies on endothelial activation, and plays a key role in the initiation of coagulation. To determine whether in vivo endothelial activation was present in patients with severe CRS, serum concentrations of VWF at the peak of CAR-T cell expansion in blood was evaluated in a subset of patients (n=60; grade 0 CRS, n=12; grade 1-3 CRS, n=39; grade ≥4 CRS, n=9), which showed that patients with grade ≥4 CRS had higher VWF concentrations compared to those with grade ≤3 CRS (FIG. 11J). The serum concentrations of Ang-2 was also evaluated, which is also released from Weibel-Palade bodies on endothelial activation and promotes capillary leak, which showed that, like VWF, Ang-2 concentrations were higher in patients with grade ≥4 CRS (FIG. 15A). Ang-1 promotes endothelial stability and an increase in the Ang-2:Ang-1 ratio has been associated with morbidity and mortality in sepsis and cerebral malaria (Mikacenic et al., *PLoS One* 10:1-13, 2015; Page and Liles, *Virulence* 4:507, 2014; Page et al., *J. Infect. Dis.* 208:929, 2013; Page et al., *Clin. Infect. Dis.* 52:e157, 2011; Ricciuto et al., *Crit. Care Med.* 39:1, 2011; Lovegrove et al., *PLoS One* 4:e4912, 2009). At the peak of CAR-T cell expansion in blood, increasing severity of CRS was associated with lower Ang-1, higher Ang-2, and an increased Ang-2:Ang-1 ratio (FIG. 11K; FIG. 15A). Of note, before both lymphodepletion and CAR-T cell infusion, and on day 1 after CAR-T cell infusion, increasing serum VWF concentration was associated with increased severity of subsequent CRS (FIG. 15B). Furthermore, before lymphodepletion and on day 1 after CAR-T cell infusion an increased Ang-2:Ang-1 ratio was associated with a higher risk of developing grade ≥4 CRS (FIG. 15C).

In an initial study of 10 patients, similar results were observed for Ang-2, Ang-1, Ang-2:Ang-1 ratio, platelet counts, sVCAM1 and sVCAM1:Ang-1 ratio (see FIGS. 16A-16G). Angiopoietin-1, angiopoietin-2 and soluble vascular cell adhesion molecule 1 (sVCAM-1) concentrations were assessed in serum from patients with acute lymphoblastic leukemia (ALL), non-Hodgkin's lymphoma (NHL) or chronic lymphocytic leukemia (CLL treated) with cyclophosphamide (Cy)-based lymphodepletion chemotherapy with or without fludarabine (Flu) and CD19-targeted chimeric antigen receptor (CAR)-modified T cells. Samples were collected before lymphodepletion chemotherapy (Prechemo), on the day of CAR-T cell infusion prior to commencing the infusion (d0), the day after CAR-T cell infusion (d1), and during acute clinical toxicity 4-8 days after CAR-T cell infusion (d4-8). Ang-1 (FIG. 16A), Ang-2 (FIG. 16B), sVCAM-1 (FIG. 16C), and platelet counts (FIG. 16D) are shown for each patient grouped by severity of neurotoxicity (patients 1-3, grade 0; patient 4, grade 3; patients 5-10, grade 4-5). Patients with grade 4-5 neurotoxicity had high Ang-2:Ang-1 ratios (FIG. 16E) and high sVCAM-1:Ang-1 ratios (FIG. 16F) during acute toxicity (black) and on the first day after CAR-T cell infusion (blue), providing an opportunity for early intervention with treatment with corticosteroids, anti-cytokine antibodies or agents that modify the angiopoietin-Tie-VCAM1 pathway. In addition, some patients who developed grade 4-5 neurotoxicity (6, 9, 10) had high Ang-2:Ang-1 or sVCAM-1:Ang-1 ratios before chemotherapy (green) or before CAR-T cell infusion (red), providing an opportunity to modify chemotherapy or CAR-T cell dosing and re-evaluate risk before starting therapy.

Together, these data indicate that biomarkers of endothelial activation are elevated during severe CRS, and that even prior to commencing lymphodepletion and CAR-T cell therapy endothelial activation might increase the risk of subsequent development of severe CRS.

Patient and Treatment Characteristics Associated with Development and Severe CRS To identify patients at risk of developing CRS, univariate analyses of the impact of baseline characteristics on the development of any grade of CRS were performed.

These analyses showed that patients with higher marrow tumor burden (P<0.0001), a higher percentage of CD19$^+$ cells in the marrow (P=0.0001), and more severe thrombocytopenia (P=0.002) were at higher risk of developing CRS (Table A). Manufacturing of CAR-T cells using bulk CD8$^+$ T cells without selection of the central memory subset (P=0.001) and the infused CAR-T cell dose (P=0.002) were associated with increased risk of CRS. Despite our previous observation that addition of Flu to Cy in lymphodepletion enhanced in vivo CAR-T cell expansion (Turtle I and II, 2016), this was not associated with increased occurrence of CRS in univariate analysis. However, analysis of the interaction between CAR-T cell dose and Cy/Flu lymphodepletion showed that addition of Flu at any given CAR-T cell dose increased the risk of CRS (P=0.03). Stepwise multivariable analysis showed that higher bone marrow CD19$^+$ tumor burden (P<0.0001), more severe thrombocytopenia (P=0.05), bulk CD8$^+$ T cell selection (P=0.03), Cy/Flu lymphodepletion (P=0.02), higher CAR-T cell dose (P=0.003), and the interaction effect of CAR-T cell dose and Cy/Flu lymphodepletion (P=0.009) were independently associated with development of CRS (Table A). Risk factors for CRS within each disease cohort are presented in Tables 7A-C.

TABLE 7A

Baseline Characteristics in B cell-ALL Patients CRS Severity

| | CRS Grade | | | | Univariate Analysis | Multivariable Analysis |
|---|---|---|---|---|---|---|
| | 0 | 1-3 | 4-5 | Total | P value[a] | P value[b] |
| Number of Patients, n | 12 | 31 | 4 | 47 | | |
| Age, years | | | | | .94 | |
| Median, [IQR] | 39 [33, 54] | 40 [26, 58] | 44 [30, 50] | 40 [29, 54] | | |
| Range | 27, 67 | 20, 73 | 20, 52 | 20, 73 | | |
| Sex, n (%) | | | | | .81 | |
| Male | 8 (30) | 17 (63) | 2 (7) | 27 (57) | | |
| Female | 4 (20) | 14 (70) | 2 (10) | 20 (43) | | |
| Karnofsky Performance, n (%) | | | | | .39 | |
| 60-70 | 1 (17) | 4 (66) | 1 (17) | 6 (13) | | |
| 80-90 | 9 (24)) | 26 (68) | 3 (8) | 38 (81) | | |
| 100 | 2 (67) | 1 (33) | 0 (0) | 3 (6) | | |
| Prior Lines of Therapy, n | | | | | .08 | |
| Median [IQR] | 3 [1, 3] | 3 [2, 4] | 3 [2, 4] | 3 [2, 4] | | |
| Range | 1, 5 | 1, 11 | 2, 5 | 1, 11 | | |
| Prior Transplant, n (%) | | | | | .04[c] | .02 |
| Allogeneic | 1 (6) | 15 (88) | 1 (6) | 17 (36) | | |
| Marrow Disease Burden by Flow Cytometry, % | | | | | .01 | .02 |
| Median [IQR] | 1.5 [0.03, 5.6] | 30 [10, 80] | 30 [20, 41] | 21 [1.1, 58] | | |
| Range | 0, 79 | 0, 97 | 12, 50 | 0, 97 | | |
| Not involved, n (%) | 1 (50) | 1 (50) | 0 (0) | 2 (4) | | |
| CD19+ Cells in Marrow by Flow Cytometry, % | | | | | .01[d] | |
| Median [IQR] | 8.3 [3.6, 14] | 31 [13, 80] | 31 [20, 42] | 26 [8.2, 61] | | |
| Range | 0, 79 | 0.6, 99 | 13, 50 | 0, 99 | | |
| Platelet Count, 1000/μl | | | | | .44 | |
| Median [IQR] | 79 [57, 184] | 66 [39, 104] | 88 [47, 126] | 75 [45, 125] | | |
| Range | 19, 244 | 2, 191 | 9, 162 | 2, 244 | | |
| CD8+ Selection Method, n (%) | | | | | .05 | .02 |
| Bulk CD8+ | 2 (10) | 16 (76) | 3 (14) | 21 (45) | | |
| Central Memory Enriched | 10 (38) | 15 (58) | 1 (4) | 26 (55) | | |
| Lymphodepletion, n (%) | | | | | 1 | |
| Cy/Flu based | 9 (26) | 22 (65)) | 3 (9) | 34 (72) | | |
| Non-Cy/Flu based | 3 (23) | 9 (69) | 1 (8) | 13 (28) | | |
| CAR-T Cell Dose, n (%) | | | | | .08 | .009 |
| 2 × 10⁵ EGFRt+ cells/kg | 7 (27) | 19 (73) | 0 (0) | 26 (55) | | |
| 2 × 10⁶ EGFRt+ cells/kg | 5 (26) | 11 (58) | 3 (16) | 19 (41) | | |
| 2 × 10⁷ EGFRt+ cells/kg | 0 (0) | 1 (50) | 1 (50) | 2 (4) | | |

[a]Two-sided P-values calculated based on Kruskal-Wallis test for continuous variables, and Fisher's Exact test for categorical variables.
[b]Step-wise multivariable proportional odds models were performed to assess impact of baseline factors on the occurrence of CRS (Grade 0 vs 1-3 vs 4-5), where $\log_{10}$ values were used to transform data as appropriate, with 0.001 substituting for values of 0.
[c]Any transplant type versus no transplant.
[d]Since marrow disease burden and total CD19+ cells in marrow have a strong correlation (r = 0.99, P < .0001), only marrow disease was included in the multivariable analysis.

TABLE 7B

Baseline Characteristics in NHL Patients by CRS Severity

| | CRS Grade | | | | Univariate Analysis | Multi-variable Analysis |
|---|---|---|---|---|---|---|
| | 0 | 1-3 | 4-5 | Total | P value[a] | P value[b] |
| Number of Patients, n | 24 | 34 | 4 | 62 | | |
| Age, years | | | | | .46 | |
| Median, [IQR] | 60 [52, 64] | 56 [52, 61] | 63 [52, 67] | 58 [52, 63] | | |
| Range | 36, 67 | 28, 70 | 43, 70 | 28, 70 | | |
| Sex, n (%) | | | | | .36 | |
| Male | 17 (35) | 29 (59) | 3 (6) | 49 (79) | | |
| Female | 7 (54) | 5 (38) | 1 (8) | 13 (21) | | |
| Karnofsky Performance, n (%) | | | | | .10 | |

TABLE 7B-continued

Baseline Characteristics in NHL Patients by CRS Severity

| | CRS Grade | | | | Univariate Analysis | Multi-variable Analysis |
| --- | --- | --- | --- | --- | --- | --- |
| | 0 | 1-3 | 4-5 | Total | P value[a] | P value[b] |
| 60-70 | 0 (0) | 5 (83) | 1 (17) | 6 (10) | | |
| 80-90 | 20 (42) | 26 (54) | 2 (4) | 48 (77) | | |
| 100 | 4 (50) | 3 (37) | 1 (13) | 8 (13) | | |
| Prior Lines of Therapy, n | | | | | .34 | |
| Median [IQR] | 4 [2, 6] | 4 [3, 5] | 5 [4, 8] | 4 [3, 5] | | |
| Range | 1, 11 | 1, 10 | 4, 9 | 1, 11 | | |
| Prior Transplant, n (%) | | | | | .85 | |
| Allogeneic | 1 (25) | 3 (75) | 0 (0) | 4 (6) | | |
| Autologous | 9 (41) | 11 (50) | 2 (9) | 22 (35) | | |
| Both | 0 (0) | 3 (100) | 0 (0) | 3 (5) | | |
| NHL Subtype, n (%) | | | | | .15 | |
| Aggressive | 17 (39) | 26 (59) | 1 (2) | 44 (71) | | |
| Follicular | 4 (44) | 3 (33) | 2 (22) | 9 (14) | | |
| Mantle Cell | 3 (33) | 5 (56) | 1 (11) | 9 (14) | | |
| Imaging Tumor Bulk, mm$^2$ | | | | | .72 | |
| Median [IQR] | 3019 [2005, 5586] | 3133 [1908, 5794] | 1752 [1579, 5352] | 3000 [1773, 5627] | | |
| Range | 0, 8792 | 124, 17907 | 1425, 8929 | 0, 17907 | | |
| Marrow Disease Burden by Flow Cytometry, % | | | | | .06 | .008 |
| Median [IQR] | 0 [0, 0] | 0 [0, 0.2] | 1.9 [0.1, 9] | 0 [0, 0.2] | | |
| Range | 0, 1.5 | 0, 88 | 0, 14 | 0, 88 | | |
| Not involved, n (%) | 20 (45) | 24 (53) | 1 (2) | 45 (73) | | |
| CD19$^+$ Cells in Marrow by Flow Cytometry, % | | | | | .67 | |
| Median [IQR] | 3.4 [1.3, 4.7] | 3.7 [0.3, 10] | 6.6 [1.4, 13] | 3.6 [0.6, 5.6] | | |
| Range | 0, 8.2 | 0, 88 | 0.32, 15 | 0, 88 | | |
| Platelet Count, 1000/μl | | | | | .02 | |
| Median [IQR] | 97 [56, 158] | 87 [44, 140] | 32 [18, 37] | 87 [44, 151] | | |
| Range | 11, 265 | 1, 553 | 5, 42 | 1, 553 | | |
| CD8$^+$ Selection Method, n (%) | | | | | .06 | |
| Bulk CD8$^+$ | 5 (21) | 17 (71) | 2 (8) | 24 (39) | | |
| Central Memory Enriched | 19 (50) | 17 (45) | 2 (5) | 38 (61) | | |
| Lymphodepletion, n (%) | | | | | .46 | .04 |
| Cy/Flu based | 17 (35) | 28 (57) | 4 (8) | 49 (79) | | |
| Non-Cy/Flu based | 7 (54) | 6 (46) | 0 (0) | 13 (21) | | |
| CAR-T Cell Dose, n (%) | | | | | .05 | |
| 2 × 10$^5$ EGFRt$^+$ cells/kg | 2 (40) | 3 (60) | 0 (0) | 5 (8) | | |
| 2 × 10$^6$ EGFRt$^+$ cells/kg | 19 (40) | 28 (58) | 1 (2) | 48 (77) | | |
| 2 × 10$^7$ EGFRt$^+$ cells/kg | 3 (33) | 3 (33) | 3 (33) | 9 (15) | | |

[a] Two-sided P-values calculated based on Kruskal-Wallis test for continuous variables, and Fisher's Exact test for categorical variables.
[b] Step-wise multivariable proportional odds models were performed to assess impact of baseline factors on the occurrence of CRS (Grade 0 vs 1-3 vs 4-5), where $\log_{10}$ values were used to transform data as appropriate, with 0.001 substituting for values of 0.
[c] Any transplant type versus no transplant.
[d] Since marrow disease burden and total CD19$^+$ cells in marrow have a strong correlation (r = 0.99, P < .0001), only marrow disease was included in the multivariable analysis.

TABLE 7C

Baseline Characteristics in CLL Patients by CRS Severity

| | CRS Grade | | | Total | Univariate Analysis P value[a] | Multivariable Analysis P value[b] |
|---|---|---|---|---|---|---|
| | 0 | 1-3 | 4-5 | | | |
| Number of Patients, n | 4 | 18 | 2 | 24 | | |
| Age, years | | | | | .15 | |
| Median, [IQR] | 67 [63, 69] | 59 [53, 64] | 59 [55, 62] | 61 [54, 65] | | |
| Range | 61, 70 | 40, 73 | 55, 62 | 40, 73 | | |
| Sex, n (%) | | | | | .79 | |
| Male | 3 (18) | 13 (76) | 1 (6) | 17 (71) | | |
| Female | 1 (14) | 5 (71) | 1 (14) | 7 (29) | | |
| Karnofsky Performance, n (%) | | | | | .71 | |
| 60-70 | 1 (50) | 1 (50) | 0 (0) | 2 (8) | | |
| 80-90 | 3 (15) | 15 (75) | 2 (10) | 20 (83) | | |
| 100 | 0 (0) | 2 (100) | 0 (0) | 2 (8) | | |
| Prior Lines of Therapy, n | | | | | .21 | |
| Median [IQR] | 6 [5, 8] | 5 [4, 7] | 7 [7, 7] | 5 [4, 7] | | |
| Range | 4, 9 | 3, 9 | 7, 7 | 3, 9 | | |
| Prior Transplant, n (%) | | | | | 1 | |
| Allogeneic | 1 (25) | 3 (75) | 0 (0) | 4 (17) | | |
| Marrow Disease Burden by Flow Cytometry, % | | | | | .11 | .11 |
| Median [IQR] | 1.8 [0.2, 41] | 66 [32, 79] | 65 [40, 90] | 62 [27, 79] | | |
| Range | 0, 78 | 0.4, 96 | 40, 90 | 0, 96 | | |
| Not involved, n (%) | 2 (100) | 0 (0.0) | 0 (0.0) | 2 (8) | | |
| CD19$^+$ Cells in Marrow by Flow Cytometry, % | | | | | .09 | |
| Median [IQR] | 2 [0.2, 41] | 66 [33, 79] | 65 [40, 90] | 62 [28, 79] | | |
| Range | 0.06, 78 | 6.7, 96 | 40, 90 | 0.06, 96 | | |
| Imaging Tumor Bulk, mm | | | | | .12 | |
| Median [IQR] | 1115 [546, 1683] | 3226 [2016, 4753] | 11750 [3093, 20406] | 3158 [1683, 4753] | | |
| Range | 546, 1683 | 1140, 11057 | 3093, 20406 | 546, 20406 | | |
| Platelet Count, 1000/μl | | | | | .04 | |
| Median [IQR] | 133 [110, 136] | 44 [26, 88] | 26 [19, 32] | 51 [28, 96] | | |
| Range | 87, 139 | 7, 170 | 19, 32 | 7, 170 | | |
| CD8$^+$ Selection Method, n (%) | | | | | .06 | |
| Bulk CD8$^+$ | 5 (21) | 17 (71) | 2 (8) | 24 (39) | | |
| Central Memory Enriched | 19 (50) | 17 (45) | 2 (5) | 38 (61) | | |
| Lymphodepletion, n (%) | | | | | 1 | |
| Cy/Flu based | 4 (19) | 15 (71) | 2 (10) | 21 (88) | | |
| Non-Cy/Flu based | 0 (0) | 3 (100) | 0 (0) | 3 (12) | | |
| CAR-T Cell Dose, n (%) | | | | | .19 | |
| $2 \times 10^5$ EGFRt$^+$ cells/kg | 1 (25) | 3 (75) | 0 (0) | 4 (17) | | |
| $2 \times 10^6$ EGFRt$^+$ cells/kg | 3 (16) | 15 (79) | 1 (5) | 19 (79) | | |
| $2 \times 10^7$ EGFRt$^+$ cells/kg | 0 (0) | 0 (0) | 1 (100) | 1 (4) | | |

[a]Two-sided P-values calculated based on Kruskal-Wallis test for continuous variables, and Fisher's Exact test for categorical variables.
[b]Step-wise multivariable proportional odds models were performed to assess impact of baseline factors on the occurrence of CRS (Grade 0 vs 1-3 vs 4-5), where $\log_{10}$ values were used to transform data as appropriate, with 0.001 substituting for values of 0.
[c]Any transplant type versus no transplant.
[d]Since marrow disease burden and total CD19$^+$ cells in marrow have a strong correlation (r = 0.99, P < .0001), only marrow disease was included in the multivariable analysis.

Risk factors for the occurrence of any grade of CRS that were identified in the multivariable model were examined to determine whether these factors also impacted the severity of CRS (Table 8). Univariate pairwise analysis showed that only Cy/Flu lymphodepletion (P=0.03) and higher CAR-T cell dose (P=0.0003) were associated with the development of grade ≥4 compared to grade 1-3 CRS.

TABLE 8

Univariate Pairwise Analysis of Significant Factors from Multivariable Proportional Odds Model

| | Univariate Pairwise P-Values | | |
|---|---|---|---|
| CRS Grade | 0 vs. 1-3 | 0 vs. 4-5 | 1-3 vs. 4-5 |
| % Marrow Burden of disease | <.0001 | 0.0001 | 0.8 |
| Platelet Count | 0.01 | 0.005 | 0.06 |
| CAR-T cell Dose Level | 0.7 | 0.005 | 0.0003 |
| Bulk CD8+ T cell Selection | 0.0005 | 0.12 | 0.7 |
| Flu/Cy Stratified by Dose Level | 0.8 | 0.4 | 0.03 |

Toxicity Mitigation and Effect on Response Rates by Reduction in Peak CAR-T Cell Counts in Blood Will be Associated with Reduced Response Rates The effect on the risk of severe CRS through the use of a reduced CAR-T cell dose in patients with high tumor burden was examined since CD19 antigen drives in vivo CAR-T cell expansion. This strategy was effective in mitigating toxicity in B-ALL patients without impairing efficacy (see Turtle et al. I, 2016). However, logistic regression studies indicated that the therapeutic window was narrow and that a reduction in CAR-T cell dose that results in peak $CD8^+$ CAR-T cells <10 cells/μL and $CD4^+$ CAR-T cells <5/μL was likely to result in reduced efficacy. This is particularly true in NHL, in which the probabilities of CR in grade ≥2 CRS and grade ≥3 neurotoxicity were similar at any given peak CAR-T cell count.

Consistent with the observation that Cy/Flu lymphodepletion and a high CAR-T cell dose were associated with severity of CRS, earlier and higher peaks in blood CAR-T cell counts in patients with grade ≥4 CRS compared to grade 1-3 or no CRS (FIGS. 12A-12D). To identify in each disease a therapeutic window of CAR-T cell counts that would minimize the risk of CRS and neurotoxicity while retaining a high probability of anti-tumor activity, logistic regression was used to examine the relationship between peak CAR-T cell counts in blood and the occurrence of toxicity or disease response (FIGS. 12E-12H). In B-ALL patients achieving a peak of 10 $CD8^+$ CAR-T cells/μL, the probability of $MRD^-$ CR was 95%, and the probabilities of grade ≥2 CRS and grade ≥3 neurotoxicity were 37% and 15%, respectively. Similar findings were noted for patients with 5 $CD4^+$ CAR-T cells/μL (MRD-CR, 94%; grade ≥2 CRS, 42%; grade ≥3 neurotoxicity, 19%). Reduction of the infused CAR-T cell dose in B-ALL patients with high marrow tumor burden were improved within in a narrow therapeutic window and were consistent targeting of peak CAR-T cell counts that were associated with high efficacy without undue toxicity (see Table 9).

TABLE 9

Peak CAR-T Cell Level in Blood from B-ALL Patients Stratified by Dose Level (DL) and Percentage of Blasts in Bone Marrow

| | Dose level | | | |
|---|---|---|---|---|
| | DL2 ($2 \times 10^6$ cells/kg) | | DL1 ($2 \times 10^5$ cells/kg) | |
| | % Marrow Blasts (n) | | | |
| | ≤5% (7) | >5% (6) | ≤5% (5) | >5% (14) |
| Peak CAR-T cells/μL | | | | |
| $CD8^+$ Median [IQR] | 25 [7.4, 260] | 315 [109, 825] | 10 [1.3, 15] | 35 [15, 170] |
| $CD4^+$ Median [IQR] | 7.7 [4.4, 22] | 16 [3.8, 27] | 5.4 [1.3, 9] | 5.3 [1.3, 15] |

The probabilities of marrow response and toxicity in CLL patients were similar to those in B-ALL. In NHL patients, a therapeutic window with high efficacy and low toxicity could not be established. These data indicate that CAR-T cell dose reduction as a sole strategy to mitigate toxicity will lead to reduced efficacy in B-ALL, CLL, and NHL patients, and that early intervention approaches should be taken that do not involve reduction in the CAR-T cell dose and peak counts in blood.

Early Identification of Patients at High Risk for Severe CRS

The risk of impaired efficacy with CAR-T cell dose reduction indicates that an optimal strategy would enable delivery of an adequate CAR-T cell dose, followed by early intervention in those at high risk of subsequent toxicity. Early onset of fever ≥38.9° C. after CAR-T cell infusion was a sensitive predictor of subsequent grade ≥4 CRS; however, the specificity of fever alone as an indicator for early intervention was low. Classification-tree modeling was used to design a simple two-step algorithm to predict grade ≥4 CRS, in which serum MCP-1 concentrations were measured only in patients with fever within 36 hours of infusion.

We investigated whether patients who would subsequently develop life-threatening CRS could be identified early after CAR-T cell infusion when early intervention strategies might be instituted. All patients who developed grade ≥4 CRS had fever ≥38.9° C. within the first 36 hours after CAR-T cell infusion; however, using fever ≥38.9° C. within 36 hours as an indication for intervention would have resulted in unnecessary treatment of 20 patients with grade ≤3 CRS (sensitivity 1.00, specificity 0.84). Within 36 hours after CAR-T cell infusion IFN-γ, IL-6, IL-8, IL-10, IL-15, MCP-1, TNFRp55, and MIP-1β concentrations were higher in serum from patients who developed grade ≥4 CRS compared to grade ≤3 CRS (P<0.0001), which were further possible predictive biomarkers for grade ≥4 CRS (FIGS. 13A-13H). Classification tree modeling was performed, which showed that in patients with fever ≥38.9° C. within 36 hours of CAR-T cell infusion, a serum IL-6 concentration ≥16 pg/mL, a serum MCP-1 concentration ≥1343.5 pg/mL enhanced identification of patients who developed grade ≥4 CRS (sensitivity 1.00, specificity 0.95) (FIG. 13I). Using this approach, only 4.5% of patients (6/133) were misclassified as at high risk of grade ≥4 CRS, 4 of whom developed grade ≥2 CRS and/or neurotoxicity, indicating that the combination of fever with IL-6 and/or MCP-1 level would sensitively and specifically identify patients at risk of developing CRS and/or neurotoxicity (i.e., unnecessary intervention would be uncommon in patients who were less likely to develop moderate or severe CRS and/or neurotoxicity). We also investigated whether patients with pre-existing endothelial activation were at higher risk for neurotoxicity. Before lymphodepletion, patients who developed gr ≥4 NT had higher Ang-2:Ang-1 ratios than those with gr ≤3 NT, indicating that endothelial activation before lymphodepletion or CAR-T cell infusion can be used as a risk factor for neurotoxicity that identifies patients who would benefit from a modified treatment regimen.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including but not limited to U.S. Provisional Patent Application No. 62/456,798 and U.S. Provisional Patent Application No. 62/544,709, are incorporated herein by reference, in their entirety. Aspects of the embodiments can be modified, if necessary to employ concepts of the various patents, applications and publications to provide yet further embodiments.

In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. A method for reducing the risk of an adverse event associated with a T cell immunotherapy, the method comprising:
   (i) measuring, in a biological sample from a mammalian subject having a hematologic malignancy and (1) prior to administration of the T cell immunotherapy to the subject or (2) within 0 to 8 days following administration of the T cell immunotherapy to the subject,
      (a) the level of a biomarker of endothelial activation selected from Angiopoietin-2, VCAM-1, von Willebrand factor antigen (vWF Ag), asymmetric dimethyl arginine (ADMA), CCL26, endothelin-1, osteoprotegerin, CD142 tissue factor, E-selectin, P-selectin, P-selectin cofactor CD63/LAMP3, PAI-1, α-fucosyltransferase VI, circulating endothelial cells, endothelial microparticles, or any combination thereof,
      (b) the ratio of Angiopoietin-2:Angiopoietin-1,
      (c) the ratio of VCAM-1:Angiopoietin-1,
      (d) the level of Angiopoietin-1, or
      (e) the ratio of ADAMTS13:vWF Ag,
   (ii) identifying the subject as at risk of developing an adverse event associated with the T cell immunotherapy when (a), (b), or (c) measured in (i) is increased, or when (d) or (e) measured in (i) is reduced, as compared to a normal sample, wherein the adverse event comprises cytokine release syndrome (CRS), neurotoxicity, or both; and
   (iii) administering to the at risk subject pre-emptive treatment for the adverse event, administering the T cell immunotherapy at a reduced dose, or both.

2. The method of claim 1, wherein the measuring in (i) comprises measuring
   (a) the level of a biomarker of endothelial activation selected from Angiopoietin-2, VCAM-1, von Willebrand factor antigen (vWF Ag), or any combination thereof,
   (b) the ratio of Angiopoietin-2:Angiopoietin-1,
   (c) the ratio of VCAM-1:Angiopoietin-1,
   (d) the level of Angiopoietin-1, or
   (e) the ratio of ADAMTS13:vWF Ag.

3. The method of claim 1, wherein the measuring in (ii) comprises measuring
   the ratio of Angiopoietin-2:Angiopoietin-1.

4. The method of claim 1, wherein the adverse event comprises neurotoxicity.

5. The method of claim 1, wherein the T cell immunotherapy comprises T cells modified to express on their cell surface a chimeric antigen-receptor (CAR).

6. The method of claim 5, wherein the CAR comprises (i) a 4-1BB costimulatory domain, (ii) a CD3ζ signaling domain, (iii) a binding domain specific for CD19, CD20, CD22, or CD37, or (iv) any combination of (i)-(iii).

7. The method of claim 1, wherein the hematologic malignancy to be treated by the T cell immunotherapy is relapsed, refractory, indolent, or a combination thereof.

8. The method of claim 1, wherein the hematologic malignancy is selected from Hodgkin's lymphoma, non-Hodgkin's lymphoma (NHL), primary central nervous system lymphomas, T cell lymphomas, small lymphocytic lymphoma (SLL), B-cell prolymphocytic leukemia, lymphoplasmacytic lymphoma, splenic marginal zone lymphoma, plasma cell myeloma, solitary plasmacytoma of bone, extraosseous plasmacytoma, extra-nodal marginal zone B-cell lymphoma (mucosa-associated lymphoid tissue (MALT) lymphoma), nodal marginal zone B-cell lymphoma, follicular lymphoma, mantle cell lymphoma, diffuse large B-cell lymphoma (DLBCL), mediastinal (thymic) large B-cell lymphoma, intravascular large B-cell lymphoma, primary effusion lymphoma, acute lymphoblastic leukemia (ALL), acute myeloid leukemia (AML), chronic lymphocytic leukemia (CLL), chronic myoblastic leukemia (CML), Hairy cell leukemia (HCL), chronic myelomonocytic leukemia (CMML), juvenile myelomonocytic leukemia (JMML), large granular lymphocytic leukemia (LGL), blastic plasmacytoid dendritic cell neoplasm (BPDCN), Burkitt lymphoma/leukemia, multiple myeloma, Bence-Jones myeloma, non-secretory myeloma, plasmacytoma, amyloidosis, monoclonal gammopathy of unknown significance (MGUS), and Waldenstrom's macroglobulinemia.

9. The method of claim 8, wherein the hematologic malignancy is selected from diffuse large B-cell lymphoma (DLBCL), mediastinal (thymic) large B-cell lymphoma, acute lymphoblastic leukemia (ALL), acute myeloid leukemia (AML), chronic lymphocytic leukemia (CLL), Hodgkin's lymphoma, and non-Hodgkin's lymphoma (NHL).

10. The method of claim 1, wherein the measuring comprises measuring the level of two, three, four or five biomarkers of endothelial activation.

11. The method of claim 1, wherein the pre-emptive treatment for the adverse event comprises a corticosteroid, an inflammatory cytokine antagonist, an endothelial cell stabilizing agent, or any combination thereof.

12. The method of claim 1, wherein the biological sample comprises blood, serum, plasma, cerebrospinal fluid (CSF), or any combination thereof.

13. The method of claim 1, wherein the T cell immunotherapy comprises CD4+ T cells and CD8+ T cells formulated in a 1:1 ratio.

14. The method of claim 1, wherein:
   (1) the biological sample comprises serum; and
   (2) the measuring in (ii) comprises measuring the ratio of Angiopoietin-2:Angiopoietin-2.

15. The method of claim 1, wherein:
(1) the biological sample comprises serum;
(2) the measuring in (ii) comprises measuring the ratio of Angiopoietin-2:Angiopoietin-2; and
(3) the T cell immunotherapy comprises T cells modified to express on their cell surface a chimeric antigen-receptor (CAR).

16. The method of claim 15, wherein the CAR comprises (i) a 4-1BB costimulatory domain, (ii) a CD3ζ signaling domain, (iii) a binding domain specific for CD19, CD20, CD22, or CD37, or (iv) any combination of (i)-(iii).

17. The method of claim 14, wherein the hematologic malignancy comprises non-Hodgkin's lymphoma (NHL), chronic lymphocytic leukemia (CLL), or acute lymphoblastic leukemia (ALL).

18. The method of claim 15, wherein the hematologic malignancy comprises non-Hodgkin's lymphoma (NHL), chronic lymphocytic leukemia (CLL), or acute lymphoblastic leukemia (ALL).

19. The method of claim 16, wherein the hematologic malignancy comprises non-Hodgkin's lymphoma (NHL), chronic lymphocytic leukemia (CLL), or acute lymphoblastic leukemia (ALL).

20. The method of claim 11, wherein the inflammatory cytokine antagonist comprises an anti-IL-6R antibody, an anti IL-6 antibody, or both.

21. The method of claim 20, wherein the inflammatory cytokine antagonist comprises tocilizumab, siltuximab, or both.

* * * * *